(12) United States Patent
Castro et al.

(10) Patent No.: US 12,295,962 B2
(45) Date of Patent: May 13, 2025

(54) POLYMORPHIC COMPOUNDS AND USES THEREOF

(71) Applicant: AskAt Inc., Nagoya (JP)

(72) Inventors: Alfredo C. Castro, Somerville, MA (US); David T. Jonaitis, Brookston, IN (US)

(73) Assignee: AskAt Inc., Nagoya (JP)

( * ) Notice: Subject to any disclaimer, the term of this patent is extended or adjusted under 35 U.S.C. 154(b) by 0 days.

(21) Appl. No.: 18/624,982

(22) Filed: Apr. 2, 2024

(65) Prior Publication Data

US 2024/0358723 A1 Oct. 31, 2024

Related U.S. Application Data

(63) Continuation of application No. 17/258,534, filed as application No. PCT/US2019/041378 on Jul. 11, 2019, now abandoned.

(60) Provisional application No. 62/834,539, filed on Apr. 16, 2019, provisional application No. 62/737,273, filed on Sep. 27, 2018, provisional application No. 62/696,463, filed on Jul. 11, 2018.

(51) Int. Cl.
| | |
|---|---|
| C07D 471/04 | (2006.01) |
| A61K 31/44 | (2006.01) |
| A61K 31/64 | (2006.01) |
| A61K 39/395 | (2006.01) |
| A61P 35/00 | (2006.01) |
| C07D 213/82 | (2006.01) |

(52) U.S. Cl.
CPC .............. *A61K 31/64* (2013.01); *A61K 31/44* (2013.01); *A61K 39/3955* (2013.01); *A61P 35/00* (2018.01); *C07D 213/82* (2013.01); *C07D 471/04* (2013.01); *C07B 2200/13* (2013.01)

(58) Field of Classification Search
CPC .......................... C07D 471/04; C07D 213/82
See application file for complete search history.

(56) References Cited

U.S. PATENT DOCUMENTS

| | | |
|---|---|---|
| 6,710,054 B2 | 3/2004 | Nakao et al. |
| 6,864,265 B2 | 3/2005 | Bridger et al. |
| 7,141,580 B2 | 11/2006 | Nakao et al. |
| 7,238,714 B2 | 7/2007 | Nakao et al. |
| 7,354,934 B2 | 4/2008 | Bridger et al. |
| 7,479,564 B2 | 1/2009 | Nakao et al. |
| 7,960,407 B2 | 6/2011 | Haruta et al. |
| 7,998,505 B2 | 8/2011 | Thoorens et al. |
| 8,921,391 B2 | 12/2014 | Take et al. |
| 9,265,756 B2 | 2/2016 | Newbold et al. |
| 9,457,084 B2 | 10/2016 | Kanazawa et al. |
| 9,688,674 B2 | 6/2017 | Take et al. |
| 9,708,258 B2 | 7/2017 | Modi et al. |
| 10,342,785 B2 | 7/2019 | Ohtani et al. |
| 10,391,086 B2 | 8/2019 | Okumura |
| 10,583,129 B2 | 3/2020 | Ohtani et al. |
| 10,611,761 B2 | 4/2020 | Take et al. |
| 10,947,235 B2 | 3/2021 | Take et al. |
| 10,973,834 B2 | 4/2021 | Manfredi et al. |
| 11,065,226 B2 | 7/2021 | Yoshida et al. |
| 2009/0018158 A1 | 1/2009 | Haruta et al. |
| 2009/0036495 A1 | 2/2009 | Audoly |
| 2012/0088723 A1 | 4/2012 | Take et al. |
| 2015/0004175 A1 | 1/2015 | Kaech et al. |
| 2015/0250773 A1 | 9/2015 | Rausch-Derra et al. |
| 2017/0253595 A1 | 9/2017 | Take et al. |
| 2017/0360764 A1 | 12/2017 | Okumura |
| 2019/0269663 A1 | 9/2019 | Ohtani et al. |
| 2019/0365680 A1 | 12/2019 | Ohtani et al. |
| 2022/0073510 A1 | 3/2022 | Take et al. |

FOREIGN PATENT DOCUMENTS

| | | |
|---|---|---|
| CA | 3029611 A1 | 1/2018 |
| EP | 2422779 A1 | 2/2012 |
| WO | WO-2000056729 A1 | 9/2000 |
| WO | WO-200232422 A2 | 4/2002 |
| WO | WO-2002032900 A2 | 4/2002 |
| WO | WO-2003086371 A2 | 10/2003 |
| WO | WO-2005021508 A1 | 3/2005 |
| WO | WO-2006095268 A1 | 9/2006 |
| WO | WO-2011102149 A1 | 8/2011 |
| WO | WO-2013090552 A1 | 6/2013 |
| WO | WO-2014148053 A1 | 9/2014 |
| WO | WO-2015134792 A1 | 9/2015 |
| WO | WO-2015134797 A1 | 9/2015 |
| WO | WO-2015179615 A1 | 11/2015 |
| WO | WO-2018008711 A1 | 1/2018 |
| WO | WO-2018039197 A1 | 3/2018 |

(Continued)

OTHER PUBLICATIONS

"Grapiprant and Pembrolizumab in Patients with Advanced or Progressive MSS Colorectal Cancer," https://clinicaltrials.gov/ct2/show/NCT03658772. Accessed May 18, 2022.

Adams et al., "Big opportunities for small molecules in immuno-oncology," Nat Rev Drug Discov, 2015; 14(9):603-22.

Albu et al., "EP4 Antagonism by E7046 diminishes Myeloid immunosuppression and synergizes with Treg reducing IL-2-Diphtheria toxin fusion protein in restoring anti-tumor immunity", Oncoimmunology. Jun. 28, 2017;6(8):e1338239.

(Continued)

*Primary Examiner* — Shawquia Jackson

(74) *Attorney, Agent, or Firm* — Dechert LLP; Andrea L. C. Reid; Gang Wang

(57) ABSTRACT

The present invention provides co-crystal and salt forms, and compositions and methods thereof, useful for treating various diseases, disorders or conditions in which EP4 prostaglandin receptors are implicated in the mediation of a proliferative disorder, by the administration of small molecule therapeutics acting as inhibitors of prostaglandin EP4 receptor activity.

12 Claims, 28 Drawing Sheets

(56) References Cited

FOREIGN PATENT DOCUMENTS

| WO | WO-2018084230 A1 | 5/2018 |
| WO | WO-2019204257 A1 | 10/2019 |
| WO | WO-2020014445 A1 | 1/2020 |
| WO | WO-2020014465 A1 | 1/2020 |
| WO | WO-2006009288 A1 | 4/2020 |
| WO | WO-2020069288 A1 | 4/2020 |
| WO | WO-2021205367 A1 | 10/2021 |

OTHER PUBLICATIONS

An et al., "Solution phase combinatorial chemistry. Discovery of 13- and 15-membered polyazapyridinocyclophane libraries with antibacterial activity," Tetrahedron. 1998;54(16):3999-4012.
Arndt and Kleinebudde, "Influence of binder properties on dry granules and tablets", Powder Technology, 2018;337:68-77.
Bao et al., "Combination of EP4 antagonist and checkpoint inhibitors promotes anti-tumor effector T cells in preclinical tumor models", J Immunother Cancer. Nov. 2015;3(Suppl2):p. 350.
Berge et al., "Pharmaceutical Salts," J Pharm Sci, 1977;66(1):1-19.
Caira, "Crystalline Polymorphism of Organic Compounds," Topics in Current Chemistry. 1998;198:163-208.
Golub et al., "Molecular classification of cancer: class discovery and class prediction by gene expression monitoring," Science. Oct. 15, 1999;286(5439):531-7.
Hilfiker et al., "Relevance of Solid-state Properties for Pharmaceutical Products", Polymorphism in the Pharmaceutical Industry; 2006; Chapter 1, pp. 1-19.
Hua et al., "Topical Loperamide-Encapsulated Liposomal Gel Increases the Severity of Inflammation and Accelerates Disease Progression in the Adjuvant-Induced Model of Experimental Rheumatoid Arthritis," Front Pharmacol. 2017; 8: 503.
Ji et al., "Modified toxicity probability interval design: a safer and more reliable method than the 3+3 design for practical phase I trials," J Clin Oncol 2013; 31(14):1785-91.
Knych et al., "Detection and pharmacokinetics of grapiprant following oral administration to exercised Thoroughbred horses," Drug Test Anal. 2018; 10(8):1237-1243.
Lala and Orucevic, "Role of nitric oxide in tumor progression: lessons from experimental tumors," Cancer Metastasis Rev. Mar. 1998;17(1):91-106.
Majumder et al., "EP4 as a Therapeutic Target for Aggressive Human Breast Cancer", Int J Mol Sci. Mar. 29, 2018;19(4):1019.
Medlineplus, "Cancer", National Library of Medicine, last updated May 18, 2017, www.nlm.nih.gov/medlineplus/cancer.html.
Mohen et al., "Propionic Acid—an Overview, Process Design and Optimization for Platform Chemical Biorefinery", Platform Chemical Biorefinery, 2016, Section 25.2.1.
Nagahisa et al., "Pharmacology of Grapiprant, a Novel EP4 Antagonist: Receptor Binding, Efficacy in a Rodent Postoperative Pain Model, and a Dose Estimation for Controlling Pain in Dogs," J Vet Pharmacol Ther. 2016; 40(3):285-292.
Nair and Jacob, "A simple practice guide for dose conversation between animals and human", J Basic Clin Pharm, 2016;7(2):27-31.
Okumura et al., "Discovery of AAT-008, a novel, potent, and selective prostaglandin EP4 receptor antagonist", Bioorg Med Chem Lett. Mar. 1, 2017;27(5):1186-1192.
Partial International Search Report and Provisional Opinion of the International Searching Authority in PCT/US2019/027603, dated Aug. 14, 2019 (15 pages).
PCT International Search Report for PCT Application No. PCT/US19/41378, mailed by the U.S. Patent and Trademark Office on Nov. 14, 2019, 4 Pages.
PCT International Search Report for PCT Application No. PCT/US19/53413, mailed Dec. 2, 2019 by the ISA/US; 3 Pages.
PCT International Search Report for PCT Appllication No. PCT/US2019/041351, mailed by the ISA/US on Oct. 1, 2019, 3 Pages.
PubChem-CID-11677589, Create Date: Oct. 26, 2006; entire document, especially p. 2 Figure, p. 6: 3.2.1 Melting Point, Grapiprant Hydrochloride; p. 10: 6.1 Drug Indication.
Rausch-Derra et al., "Pharmacokinetic comparison of oral tablet and suspension formulations of grapiprant, a novel therapeutic for the pain and inflammation of osteoarthritis in dogs," J Vet Pharamacol Ther. 2016;39(6):566-571.
Rojas et al., "Functional assessment of four types of disintegrants and their effect on the spironolactone release properties", AAPS PharmSciTech, 2012;13(4):1054-62.
Saal and Becker, "Pharmaceutical salts: a summary on doses of salt formers from the Orange Book", Eur J Pharm Sci. Jul. 16, 2013;49(4):614-23.
Shaw et al., "Grapiprant: an EP4 prostaglandin receptor antagonist and novel therapy for pain and inflammation", Vet Med Sci . Dec. 21, 2015;2(1):3-9.
Toogood, "Small molecule immuno-oncology therapeutic agents," Bioorg Med Chem Lett, 2018;28(3):319-329.
Watson, "Are We Close to a Cure for Chronic Lymphocytic Leukemia?", Healthline, last updated Jan. 12, 2023, https://www.healthline.com/health/cll/cll-cure-are-we-close.
Yurdakul et al., "Axial Spondyloarthritis and Autosomal Dominant Polycystic Kidney Disease in Two Siblings: a Rare Cooccurrence." Case Rep Rheumatol. 2018; 6150875.
Lee et al., Differential expression of E prostanoid receptors in murine and human non-melanoma skin cancer, J Invest Dermatol. Oct. 2005;125(4):818-25.
Piazuelo et al., "Effects of selective PGE2 receptor antagonists in esophageal adenocarcinoma cells derived from Barrett's esophagus", Prostaglandins Other Lipid Mediat. Dec. 2006;81(3-4): 150-61, Abstract.
Sapienza et al. "EP4-mediated prostanoid signalling promotes oral cancer progression", BMC Proc. Sep. 24, 2010;4 (Suppl 2):p. 35.
Chell et al., "Increased EP4 Receptor Expression in Colorectal Cancer Progression Promotes Cell Growth and Anchorage Independence", Cancer Res. Mar. 15, 2006;66(6):3106-13.
Xia et al., "Prostaglandin E2 promotes the cell growth and invasive ability of hepatocellular carcinoma cells by upregulating c-Myc expression via EP4 receptor and the PKA signaling pathway", Oncol Rep. Oct. 2014;32(4):1521-30.
Kashiwagi et al., "Prostaglandin receptors induce urothelial tumourigenesis as well as bladder cancer progression and cisplatin resistance presumably via modulating PTEN expression" Br J Cancer. 2018; 118(2):213-223.
Charo et al., "Prostaglandin E2 regulates pancreatic stellate cell activity via the EP4 receptor", Pancreas. Apr. 2013;42(3):467-74.
Obermajer et al., "PGE2-Induced CXCL12 Production and CXCR4 Expression Controls the Accumulation of Human MDSCs in Ovarian Cancer Environment", Cancer Res. Dec. 15, 2011;71(24):7463-70.
Sales et al., "Cyclooxygenase-2 Expression and Prostaglandin E2 Synthesis Are Up-Regulated in Carcinomas of the Cervix: A Possible Autocrine/Paracrine Regulation of Neoplastic Cell Function via EP2/EP4 Receptors", J Clin Endocrinol Metab. May 2001;86(5):2243-9.
Sung et al., "Lack of Expression of the EP2 but not EP3 Receptor for Prostaglandin E2 Results in Suppression of Skin Tumor Development", Cancer Res. Oct. 15, 2005;65(20):9304-11.
Simper et al., "The tumor promoting activity of the EP4 receptor forprostaglandin E2 in murine skin", Mol Oncol. Dec. 2014;8(8):1626-39.
Wu et al., "Prostaglandin E2 regulates renal cell carcinoma invasion through the EP4 receptor-Rap GTPase signal transduction pathway", J Biol Chem. Sep. 30, 2011;286(39):33954-62.

POLYMORPHIC COMPOUNDS AND USES THEREOF

CROSS-REFERENCE TO RELATED APPLICATIONS

This application is a Continuation of U.S. patent application Ser. No. 17/258,534 filed on Jan. 7, 2021, which is a U.S. national stage filing under 35 U.S.C. § 371 of PCT/US2019/041378, filed Jul. 11, 2019, which claims the benefit of U.S. Provisional Application No. 62/696,463 filed on Jul. 11, 2018, U.S. Provisional Application No. 62/737,273 filed on Sep. 27, 2018, and U.S. Provisional Application No. 62/834,539 filed on Apr. 16, 2019. The entire contents of these applications are incorporated by reference herein to their entireties.

FIELD OF THE INVENTION

This application relates to various forms and compositions, and methods, useful for treating various diseases, disorders or conditions in which EP4 prostaglandin receptors are implicated in the mediation of a proliferative disorder, by the administration of small molecule therapeutics acting as inhibitors of prostaglandin EP4 receptor activity.

BACKGROUND OF THE INVENTION

Prostaglandins are mediators of pain, fever and other symptoms associated with inflammation. Prostaglandin $E_2$ ($PGE_2$) is the predominant eicosanoid detected in inflammation conditions. In addition, it is also involved in various physiological and/or pathological conditions such as hyperalgesia, uterine contraction, digestive peristalsis, awakeness, suppression of gastric acid secretion, blood pressure, platelet function, bone metabolism, angiogenesis or the like.

Four $PGE_2$ receptor subtypes (EP1, EP2, EP3 and EP4) displaying different pharmacological properties exist. The EP4 subtype, a Gs-coupled receptor, stimulates cAMP production as well as PI3K and GSK3β signaling, and is distributed in a wide variety of tissue suggesting a major role in $PGE_2$-mediated biological events. Various EP4 inhibitors have been described previously, for example, in WO 2002/032900, WO 2005/021508, U.S. Pat. Nos. 6,710,054, and 7,238,714, the contents of which are incorporated herein by reference in their entireties.

Accordingly, there is a need for treating, preventing, and/or reducing severity of a proliferative disorder associated with prostaglandin EP4 receptor activity. The present invention addresses such a need.

SUMMARY OF THE INVENTION

It has now been found that compounds of the present invention, and compositions thereof, are useful for treating, preventing, and/or reducing severity of a proliferative disorder associated with prostaglandin EP4 receptor activity. In general, salt forms and co-crystal forms, and pharmaceutically acceptable compositions thereof, are useful for treating or lessening the severity of proliferative disorders associated with prostaglandin EP4 receptor activity, as described in detail herein. Such compounds are represented by the chemical structure below, denoted as compound A (also known as grapiprant):

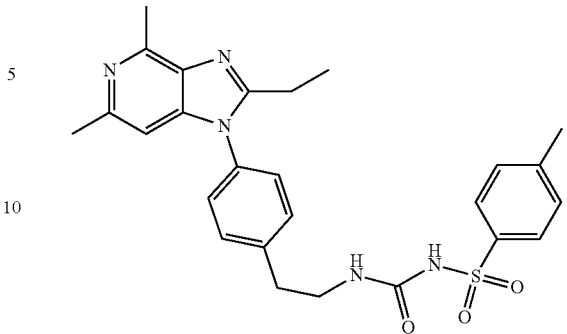

or a pharmaceutically acceptable salt thereof.

Compounds of the present invention, and pharmaceutically acceptable compositions thereof, are useful for treating a variety of diseases, disorders or conditions, associated with prostaglandin EP4 receptor activity. Such diseases, disorders, or conditions include those described herein.

Compounds provided by this invention are also useful for the study of certain prostaglandin EP4 inhibitors in biology and pathological phenomena.

DETAILED DESCRIPTION OF THE INVENTION

Figure 1:
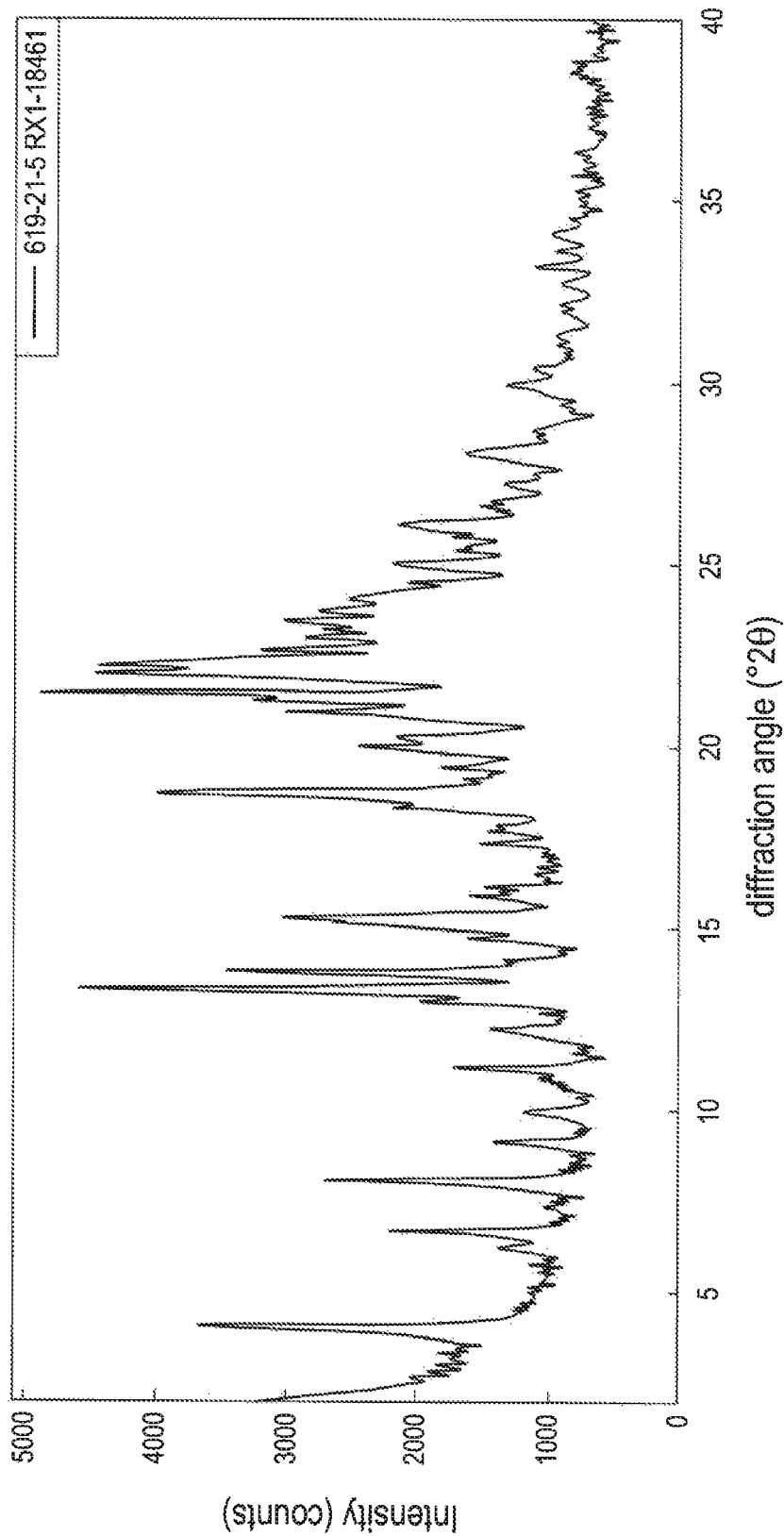
FIG. 1 depicts the XRPD pattern of Compound 1, Form A.

General Description of Certain Aspects of the Invention

U.S. Pat. No. 7,960,407, filed Mar. 1, 2006 and issued Jun. 14, 2011 ("the '407 patent," the entirety of which is hereby incorporated herein by reference), describes certain EP4 inhibitor compounds. Such compounds include compound A:

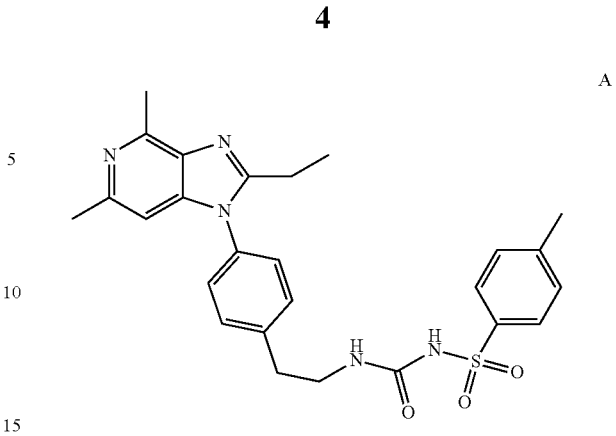

or a pharmaceutically acceptable salt thereof.

Compound A, N-[({2-[4-(2-Ethyl-4,6-dimethyl-1H-imidazo[4,5-c]pyridin-1-yl) phenyl]ethyl}amino) carbonyl]-4-methylbenzenesulfonamide, is described in detail in the '407 patent, including its synthetic route. The '407 patent also discloses a variety of physical forms of compound A.

It would be desirable to provide a solid form of compound A (e.g., as a co-crystal thereof or salt thereof) that imparts characteristics such as improved aqueous solubility, stability and ease of formulation. Accordingly, the present invention provides both co-crystal forms and salt forms of compound A:

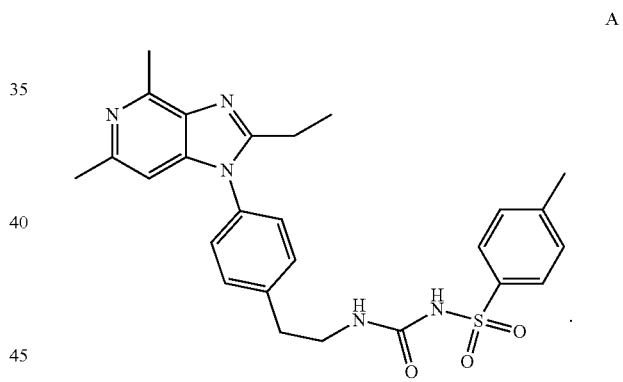

Salt and Co-Crystal Forms of Compound A

In some embodiments, compound A forms a salt via ionic bonds, or a cocrystal via van der waals and pi-pi interactions, among others, to form one of compounds 1 through 11, described below. It is contemplated that compounds 1 through 11 can exist in a variety of physical forms. For example, compounds 1 through 11 can be in solution, suspension, or in solid form. In certain embodiments, compounds 1 through 11 are in solid form. When compounds 1 through 11 are in solid form, said compounds may be amorphous, crystalline, or a mixture thereof. Exemplary such solid forms of compounds 1 through 11 are described in more detail below.

Compound 1 (Edisylate Salts of Compound A)

According to one embodiment, the present invention provides an edisylate salt of compound A, represented by compound 1:

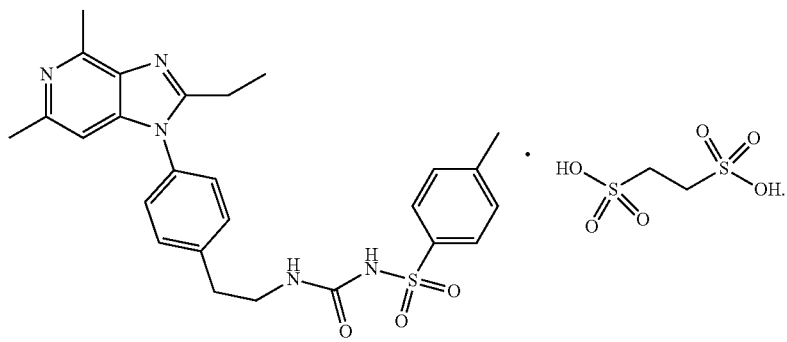

It will be appreciated by one of ordinary skill in the art that the 1,2-ethanedisulfonic acid and compound A are ionically bonded to form compound 1. It is contemplated that compound 1 can exist in a variety of physical forms. For example, compound 1 can be in solution, suspension, or in solid form. In certain embodiments, compound 1 is in solid form. When compound 1 is in solid form, said compound may be amorphous, crystalline, or a mixture thereof. Exemplary solid forms are described in more detail below.

In some embodiments, the present invention provides compound 1 substantially free of impurities. As used herein, the term "substantially free of impurities" means that the compound contains no significant amount of extraneous matter. Such extraneous matter may include excess 1,2-ethanedisulfonic acid, excess compound A, residual solvents, or any other impurities that may result from the preparation of, and/or isolation of, compound 1. In certain embodiments, at least about 95% by weight of compound 1 is present. In still other embodiments of the invention, at least about 99% by weight of compound 1 is present.

According to one embodiment, compound 1 is present in an amount of at least about 97, 97.5, 98.0, 98.5, 99, 99.5, 99.8 weight percent where the percentages are based on the total weight of the composition. According to another embodiment, compound 1 contains no more than about 3.0 area percent HPLC of total organic impurities and, in certain embodiments, no more than about 1.5 area percent HPLC total organic impurities relative to the total area of the HPLC chromatogram. In other embodiments, compound 1 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 1 is also meant to include all tautomeric forms of compound 1. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 1 can exist in a variety of solid forms. Exemplary such forms include polymorphs such as those described herein.

In certain embodiments, compound 1 is a crystalline solid. In other embodiments, compound 2 is a crystalline solid substantially free of amorphous compound 1. As used herein, the term "substantially free of amorphous compound 1" means that the compound contains no significant amount of amorphous compound 1. In certain embodiments, at least about 95% by weight of crystalline compound 1 is present. In still other embodiments of the invention, at least about 99% by weight of crystalline compound 1 is present.

It has been found that compound 1 can exist in at least one distinct polymorphic form. In some embodiments, the present invention provides a polymorphic form of Compound 1 referred to herein as Form A.

In some embodiments, compound 1 is amorphous. In some embodiments, compound 1 is amorphous, and is substantially free of crystalline compound 1.

Form A of Compound 1

In some embodiments, Form A of compound 1 has at least 1, 2, 3, 4 or 5 spectral peak(s) selected from the peaks listed in Table 1 below.

TABLE 1

XRPD Peak Positions for Form A of Compound 1

| Position [°2θ][1] | Intensity [%] |
|---|---|
| 4.0 | 71.6 |
| 6.2 | 15.98 |
| 6.7 | 39.98 |
| 7.3 | 3.08 |
| 8.1 | 50.62 |
| 9.1 | 12.66 |
| 9.9 | 8.31 |
| 11.2 | 27.74 |
| 12.2 | 22.36 |
| 13.0 | 100 |
| 13.3 | 42.29 |
| 13.8 | 38.6 |
| 14.7 | 17.47 |
| 15.2 | 70.22 |
| 15.3 | 12.2 |
| 15.9 | 24.11 |
| 17.3 | 4.53 |
| 17.7 | 3.19 |
| 18.3 | 44.39 |
| 18.7 | 43.29 |
| 20.0 | 17.3 |
| 20.2 | 5.08 |
| 21.0 | 54.75 |
| 21.5 | 53.97 |
| 22.0 | 74.63 |
| 22.2 | 62.86 |
| 22.6 | 16.25 |
| 22.9 | 42.78 |
| 23.5 | 17.78 |
| 23.7 | 15.33 |
| 24.1 | 21.44 |
| 26.1 | 17 |
| 28.0 | 26.35 |
| 28.7 | 7.07 |

TABLE 1-continued

XRPD Peak Positions for Form A of Compound 1

| Position [°2θ][1] | Intensity [%] |
|---|---|
| 29.9 | 42.03 |
| 33.2 | 4.02 |
| 34.1 | 8.13 |

[1]In this and all subsequent tables, the position 2θ is within ±0.2.

In some embodiments, Form A of compound 1 is characterized in that it has one or more peaks in its X-ray powder diffraction pattern selected from those at about 13.0, about 15.2 and about 22.0 degrees 2-theta. In some embodiments, Form A of compound 1 is characterized in that it has two or more peaks in its X-ray powder diffraction pattern selected from those at about 13.0, about 15.2 and about 22.0 degrees 2-theta. In some embodiments, Form A of compound 1 is characterized in that it has all three peaks in its X-ray powder diffraction pattern selected from those at about 13.0, about 15.2 and about 22.0 degrees 2-theta.

In certain embodiments, the X-ray powder diffraction pattern is substantially similar to the XRPD provided in FIG. 1.

Methods for preparing Form A of compound 1 are described infra.

In some embodiments, the present invention provides compound 1:

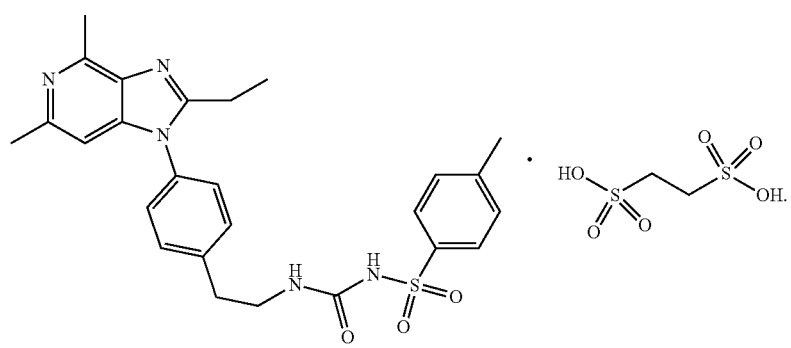

1

In some embodiments, the present invention provides compound 1, wherein said compound is crystalline.

In some embodiments, the present invention provides compound 1, wherein said compound is a crystalline solid substantially free of amorphous compound 1.

In some embodiments, the present invention provides compound 1, wherein said compound is substantially free of impurities.

In some embodiments, the present invention provides compound 1, wherein said compound has one or more peaks in its XRPD selected from those at about 13.0, about 15.2 and about 22.0 degrees 2-theta. In some such embodiments, the present invention provides compound 1, wherein said compound has at least two peaks in its XRPD selected from those at about 13.0, about 15.2 and about 22.0 degrees 2-theta. In some such embodiments, the present invention provides compound 1, wherein said compound is of Form A.

In some embodiments, the present invention provides compound 1, wherein said compound has an XRPD substantially similar to that depicted in FIG. 1.

In some embodiments, the present invention provides a composition comprising compound 1 and a pharmaceutically acceptable carrier or excipient.

In some embodiments, the present invention provides a method of inhibiting, preventing and/or reducing severity of a proliferative disorder associated with prostaglandin EP4 receptor activity in a patient comprising administering to said patient compound 1 or composition thereof.

In some embodiments, the present invention provides a method of treating various conditions in a patient in which prostaglandin EP4 receptor activity is implicated in the pathogenesis, comprising administering to said patient compound 1 or composition thereof. In some such embodiments, the various conditions in a patient in which prostaglandin EP4 receptor activity is implicated in the pathogenesis may include cancer, such as, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

Compound 2 (Ethanesulfonic Salts of Compound A)

According to one embodiment, the present invention provides an esylate salt of compound A, represented by compound 2:

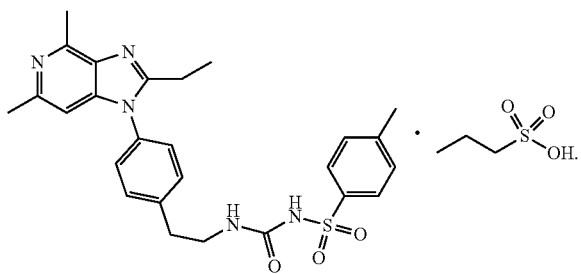

It will be appreciated by one of ordinary skill in the art that the ethanesulfonic acid and compound A are ionically bonded to form compound 2. It is contemplated that compound 2 can exist in a variety of physical forms. For example, compound 2 can be in solution, suspension, or in solid form. In certain embodiments, compound 2 is in solid form. When compound 2 is in solid form, said compound may be amorphous, crystalline, or a mixture thereof. Exemplary solid forms are described in more detail below.

In some embodiments, the present invention provides compound 2 substantially free of impurities. As used herein, the term "substantially free of impurities" means that the compound contains no significant amount of extraneous matter. Such extraneous matter may include excess ethanesulfonic acid, excess compound A, residual solvents, or any other impurities that may result from the preparation of, and/or isolation of, compound 2. In certain embodiments, at least about 95% by weight of compound 2 is present. In still other embodiments of the invention, at least about 99% by weight of compound 2 is present.

According to one embodiment, compound 2 is present in an amount of at least about weight of the composition. According to another embodiment, compound 2 contains no more than about 3.0 area percent HPLC of total organic impurities and, in certain embodiments, no more than about 1.5 area percent HPLC total organic impurities relative to the total area of the HPLC chromatogram. In other embodiments, compound 2 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 2 is also meant to include all tautomeric forms of compound 2. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 2 can exist in a variety of solid forms. Exemplary such forms include polymorphs such as those described herein.

In certain embodiments, compound 2 is a crystalline solid. In other embodiments, compound 2 is a crystalline solid substantially free of amorphous compound 2. As used herein, the term "substantially free of amorphous compound 2" means that the compound contains no significant amount of amorphous compound 2. In certain embodiments, at least about 95% by weight of crystalline compound 2 is present. In still other embodiments of the invention, at least about 99% by weight of crystalline compound 2 is present.

In some embodiments, compound 2 is amorphous. In some embodiments, compound 2 is amorphous, and is substantially free of crystalline compound 2.

Form A of Compound 2

In some embodiments, Form A of compound 2 has at least 1, 2, 3, 4 or 5 spectral peak(s) selected from the peaks listed in Table 2 below.

TABLE 2

XRPD Peak Positions for Form A of Compound 2

| Position [°2θ][1] | Intensity [%] |
|---|---|
| 7.0 | 25.33 |
| 7.7 | 1.4 |
| 9.8 | 2.85 |
| 10.1 | 8.06 |
| 10.6 | 33.26 |
| 13.9 | 25.89 |
| 14.3 | 7.97 |
| 14.9 | 1.44 |
| 15.4 | 13.75 |
| 15.6 | 12.5 |
| 16.1 | 12.27 |
| 17.1 | 6.92 |
| 17.7 | 12.48 |
| 18.7 | 28.32 |
| 19.0 | 2.48 |
| 19.4 | 100 |
| 19.7 | 7.42 |
| 20.3 | 3.79 |
| 20.6 | 16.86 |
| 21.2 | 10.92 |
| 22.0 | 5.4 |
| 22.4 | 44.45 |
| 22.6 | 19.97 |
| 22.9 | 22.43 |
| 23.4 | 6.39 |
| 23.6 | 8.31 |
| 23.8 | 14.16 |
| 24.4 | 1.95 |
| 25.8 | 21.26 |
| 26.3 | 0.5 |
| 26.5 | 6.39 |
| 26.7 | 5.16 |
| 27.1 | 4.54 |
| 27.3 | 9.29 |
| 27.6 | 6.69 |
| 27.8 | 3 |
| 28.0 | 2.21 |
| 28.5 | 4.18 |
| 28.8 | 1.88 |
| 29.2 | 4.7 |
| 29.4 | 2.06 |
| 30.6 | 4.12 |
| 31.0 | 2 |
| 31.1 | 0.88 |
| 31.4 | 1.02 |
| 31.9 | 3.47 |
| 32.6 | 2.62 |
| 33.3 | 1.68 |
| 33.5 | 0.61 |
| 33.8 | 0.5 |
| 34.4 | 0.63 |
| 35.1 | 1.09 |
| 35.8 | 2.84 |
| 36.4 | 0.7 |
| 36.6 | 2.1 |
| 36.8 | 4.7 |
| 37.6 | 3.53 |
| 37.8 | 0.69 |
| 39.1 | 0.83 |
| 39.4 | 0.45 |
| 39.5 | 0.54 |

[1]In this and all subsequent tables, the position 2θ is within ±0.2.

In some embodiments, Form A of compound 2 is characterized in that it has one or more peaks in its X-ray powder diffraction pattern selected from those at about 10.6, about 19.4 and about 22.4 degrees 2-theta. In some embodiments, Form A of compound 2 is characterized in that it has two or more peaks in its X-ray powder diffraction pattern selected from those at about 10.6, about 19.4 and about 22.4 degrees 2-theta. In some embodiments, Form A of compound 2 is characterized in that it has all three peaks in its X-ray powder diffraction pattern selected from those at about 10.6, about 19.4 and about 22.4 degrees 2-theta.

Figure 3:
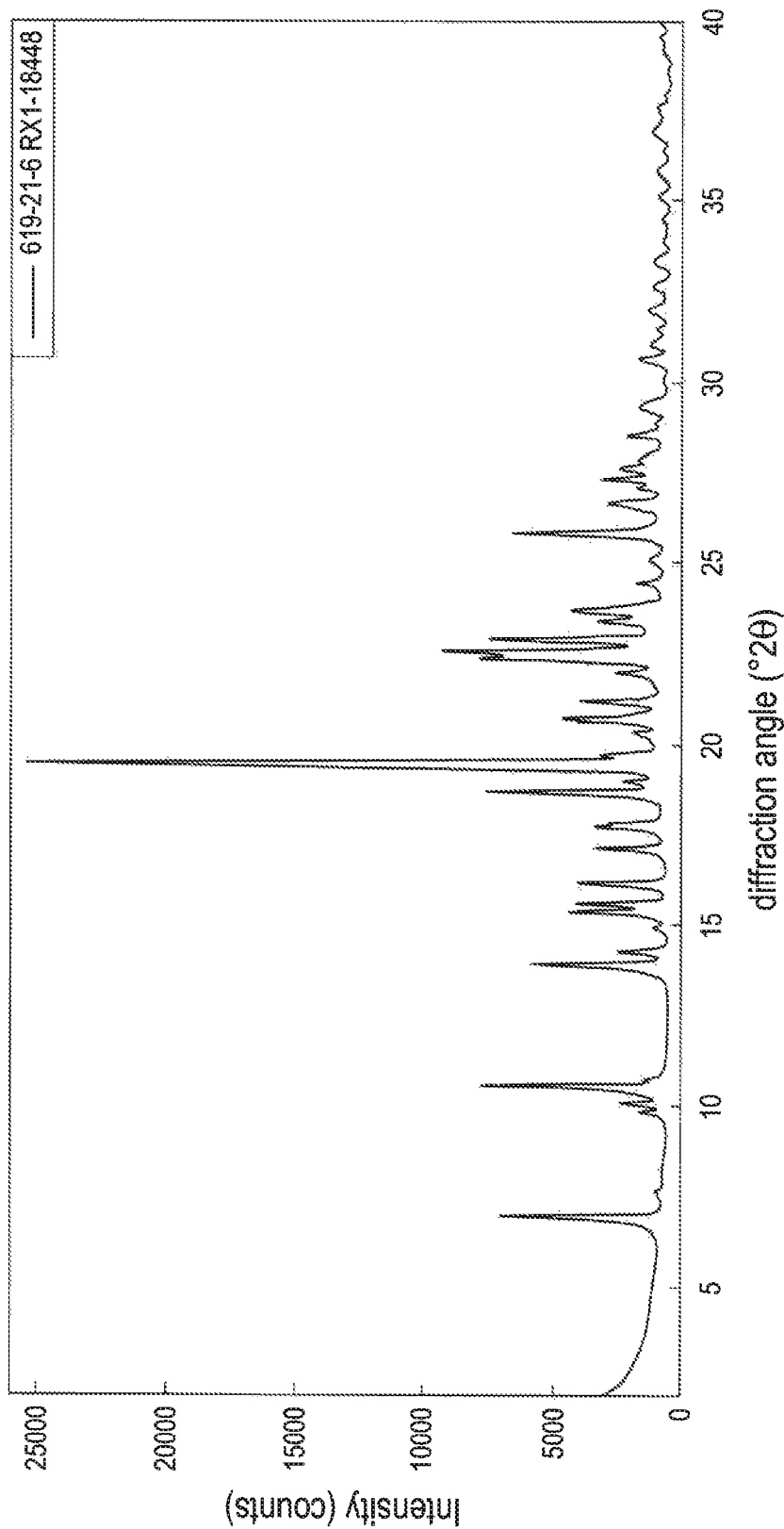
FIG. 3 depicts the XRPD pattern of Compound 2, Form A.

In certain embodiments, the X-ray powder diffraction pattern is substantially similar to the XRPD provided in FIG. 3.

Methods for preparing Form A of compound 2 are described infra.

In some embodiments, the present invention provides compound 2:

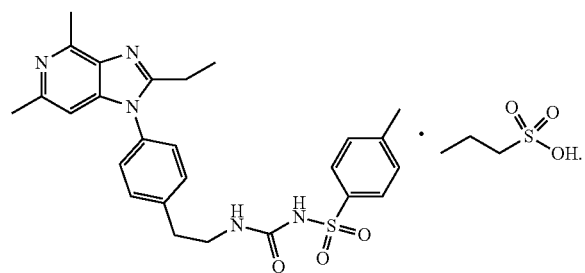

2

In some embodiments, the present invention provides compound 2, wherein said compound is crystalline.

In some embodiments, the present invention provides compound 2, wherein said compound is a crystalline solid substantially free of amorphous compound 2.

In some embodiments, the present invention provides compound 2, wherein said compound is substantially free of impurities.

In some embodiments, the present invention provides compound 2, wherein said compound has one or more peaks in its XRPD selected from those at about 10.6, about 19.4 and about 22.4 degrees 2-theta. In some such embodiments, the present invention provides compound 2, wherein said compound has at least two peaks in its XRPD selected from those at about 10.6, about 19.4 and about 22.4 degrees 2-theta. In some such embodiments, the present invention provides compound 2, wherein said compound is of Form A.

In some embodiments, the present invention provides compound 2, wherein said compound has an XRPD substantially similar to that depicted in FIG. 3.

In some embodiments, the present invention provides a composition comprising compound 2 and a pharmaceutically acceptable carrier or excipient.

In some embodiments, the present invention provides a method of inhibiting, preventing and/or reducing severity of a proliferative disorder associated with prostaglandin EP4 receptor activity in a patient comprising administering to said patient compound 2 or composition thereof.

In some embodiments, the present invention provides a method of treating various conditions in a patient in which prostaglandin EP4 receptor activity is implicated in the pathogenesis, comprising administering to said patient compound 2 or composition thereof. In some such embodiments, the various conditions in a patient in which prostaglandin EP4 receptor activity is implicated in the pathogenesis may include cancer, such as, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

Compound 3 (Gentisate Salts of Compound A)

According to one embodiment, the present invention provides a gentisate salt of compound A, represented by compound 3:

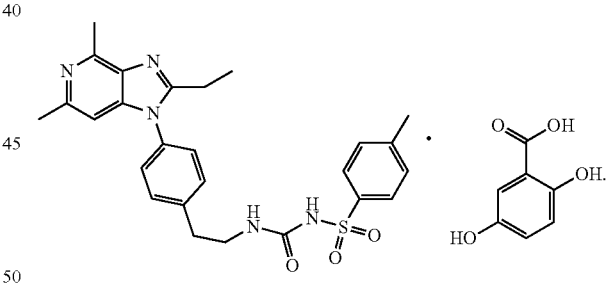

3

It will be appreciated by one of ordinary skill in the art that the gentisic acid and compound A are ionically bonded to form compound 3. It is contemplated that compound 3 can exist in a variety of physical forms. For example, compound 3 can be in solution, suspension, or in solid form. In certain embodiments, compound 3 is in solid form. When compound 3 is in solid form, said compound may be amorphous, crystalline, or a mixture thereof. Exemplary solid forms are described in more detail below.

In some embodiments, the present invention provides compound 3 substantially free of impurities. As used herein, the term "substantially free of impurities" means that the compound contains no significant amount of extraneous matter. Such extraneous matter may include excess gentisic acid, excess compound A, residual solvents, or any other impurities that may result from the preparation of, and/or isolation of, compound 3. In certain embodiments, at least about 95% by weight of compound 3 is present. In still other embodiments of the invention, at least about 99% by weight of compound 3 is present.

According to one embodiment, compound 3 is present in an amount of at least about 97, 97.5, 98.0, 98.5, 99, 99.5, 99.8 weight percent where the percentages are based on the total weight of the composition. According to another embodiment, compound 3 contains no more than about 3.0 area percent HPLC of total organic impurities and, in certain embodiments, no more than about 1.5 area percent HPLC total organic impurities relative to the total area of the HPLC chromatogram. In other embodiments, compound 3 contains no more than about 1.0% area percent HPLC of any single impurity; no more than about 0.6 area percent HPLC of any single impurity, The structure depicted for compound 3 is also meant to include all tautomeric forms of compound 3. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

It has been found that compound 3 can exist in a variety of solid forms. Exemplary such forms include polymorphs such as those described herein.

In certain embodiments, compound 3 is a crystalline solid. In other embodiments, compound 3 is a crystalline solid substantially free of amorphous compound 3. As used herein, the term "substantially free of amorphous compound 3" means that the compound contains no significant amount of amorphous compound 3. In certain embodiments, at least about 95% by weight of crystalline compound 3 is present. In still other embodiments of the invention, at least about 99% by weight of crystalline compound 3 is present.

In some embodiments, compound 3 is amorphous. In some embodiments, compound 3 is amorphous, and is substantially free of crystalline compound 3.

Form A of Compound 3

In some embodiments, Form A of compound 3 has at least 1, 2, 3, 4 or 5 spectral peak(s) selected from the peaks listed in Table 3 below.

TABLE 3

XRPD Peak Positions for Form A of Compound 3

| Position [°2θ][1] | Intensity [%] |
|---|---|
| 8.2 | 64.33 |
| 9.5 | 100 |
| 9.9 | 20.01 |
| 12.4 | 34.52 |
| 13.0 | 25.53 |
| 15.0 | 2.18 |
| 15.4 | 8.24 |
| 15.7 | 21.79 |
| 16.2 | 2.41 |
| 16.9 | 17.35 |
| 17.1 | 7.65 |
| 17.4 | 9.75 |
| 18.5 | 21.22 |
| 19.0 | 2.17 |
| 20.3 | 9.43 |
| 20.6 | 18.62 |
| 21.7 | 8.26 |
| 22.8 | 26.07 |
| 23.2 | 16.5 |
| 23.6 | 17.27 |

TABLE 3-continued

XRPD Peak Positions for Form A of Compound 3

| Position [°2θ][1] | Intensity [%] |
|---|---|
| 24.8 | 11.08 |
| 25.0 | 6.16 |
| 25.2 | 2.9 |
| 25.8 | 24.55 |
| 26.4 | 5.5 |
| 27.4 | 2.95 |
| 27.6 | 4.51 |
| 27.8 | 1.5 |
| 29.0 | 15.21 |
| 29.2 | 5.54 |
| 30.2 | 2.86 |
| 30.7 | 3.56 |
| 31.7 | 3.3 |
| 32.1 | 2.77 |
| 32.4 | 2.42 |
| 32.9 | 4.46 |
| 33.2 | 5.34 |
| 33.8 | 1.01 |
| 34.4 | 0.79 |
| 36.0 | 2.24 |
| 36.5 | 0.93 |
| 37.3 | 0.58 |
| 37.6 | 0.74 |
| 39.0 | 2.68 |

[1]In this and all subsequent tables, the position 2θ is within ±0.2.

In some embodiments, Form A of compound 3 is characterized in that it has one or more peaks in its X-ray powder diffraction pattern selected from those at about 8.2, about 9.5 and about 12.4 degrees 2-theta. In some embodiments, Form A of compound 3 is characterized in that it has two or more peaks in its X-ray powder diffraction pattern selected from those at about 8.2, about 9.5 and about 12.4 degrees 2-theta. In some embodiments, Form A of compound 3 is characterized in that it has all three peaks in its X-ray powder diffraction pattern selected from those at about 8.2, about 9.5 and about 12.4 degrees 2-theta.

Figure 5:
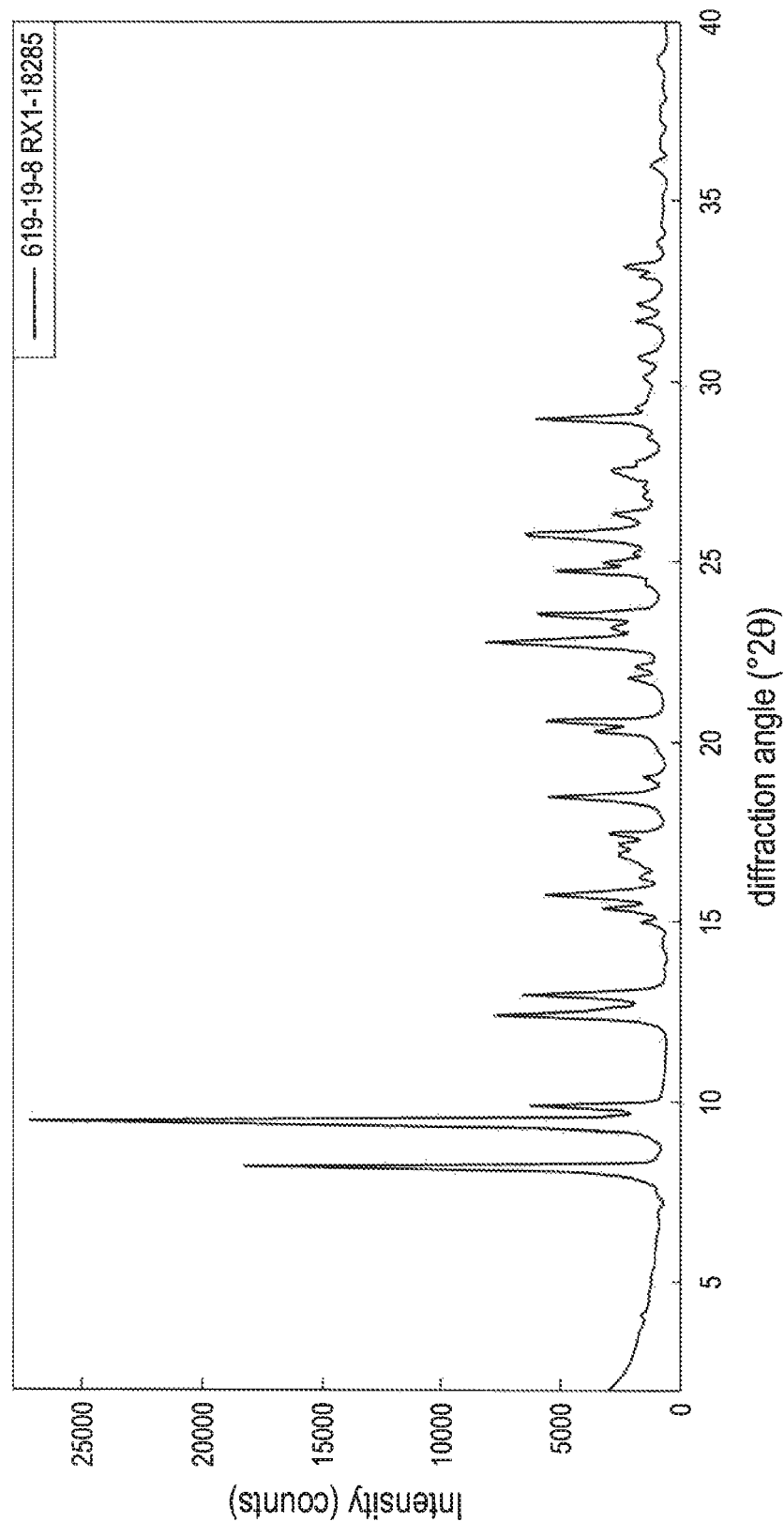
FIG. 5 depicts the XRPD pattern of Compound 3, Form A.

In certain embodiments, the X-ray powder diffraction pattern is substantially similar to the XRPD provided in FIG. 5.

Methods for preparing Form A of compound 3 are described infra.

In some embodiments, the present invention provides compound 3:

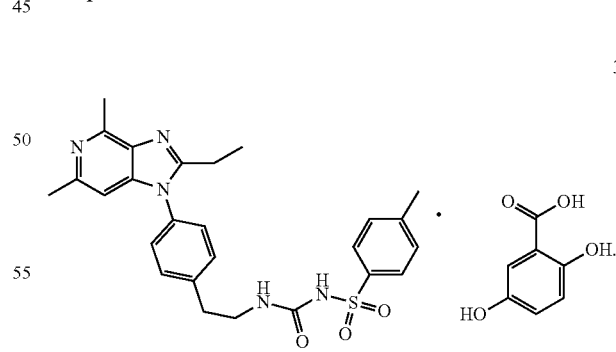

In some embodiments, the present invention provides compound 3, wherein said compound is crystalline.

In some embodiments, the present invention provides compound 3, wherein said compound is a crystalline solid substantially free of amorphous compound 3.

In some embodiments, the present invention provides compound 3, wherein said compound is substantially free of impurities.

In some embodiments, the present invention provides compound 3, wherein said compound has one or more peaks in its XRPD selected from those at about 8.2, about 9.5 and about 12.4 degrees 2-theta. In some such embodiments, the present invention provides compound 3, wherein said compound has at least two peaks in its XRPD selected from those at about 8.2, about 9.5 and about 12.4 degrees 2-theta. In some such embodiments, the present invention provides compound 3, wherein said compound is of Form A.

In some embodiments, the present invention provides compound 3, wherein said compound has an XRPD substantially similar to that depicted in FIG. 5.

In some embodiments, the present invention provides a composition comprising compound 3 and a pharmaceutically acceptable carrier or excipient.

In some embodiments, the present invention provides a method of inhibiting, preventing and/or reducing severity of a proliferative disorder associated with prostaglandin EP4 receptor activity in a patient comprising administering to said patient compound 3 or composition thereof.

In some embodiments, the present invention provides a method of treating various conditions in a patient in which prostaglandin EP4 receptor activity is implicated in the pathogenesis, comprising administering to said patient compound 3 or composition thereof. In some such embodiments, the various conditions in a patient in which prostaglandin EP4 receptor activity is implicated in the pathogenesis may include cancer, such as, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

Compound 4 (Hydrochloride Salts of Compound A)

According to one embodiment, the present invention provides a hydrochloride salt of compound A, represented by compound 4:

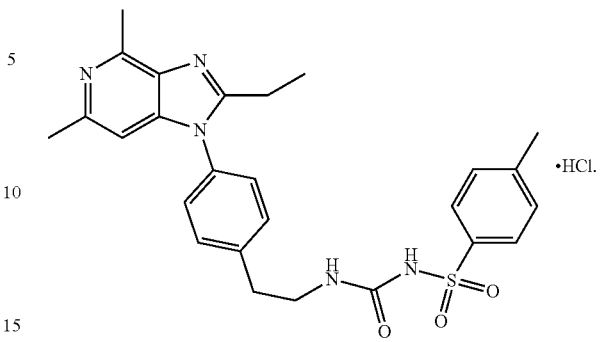

4

It will be appreciated by one of ordinary skill in the art that the hydrochloric acid and compound A are ionically bonded to form compound 4. It is contemplated that compound 4 can exist in a variety of physical forms. For example, compound 4 can be in solution, suspension, or in solid form. In certain embodiments, compound 4 is in solid form. When compound 4 is in solid form, said compound may be amorphous, crystalline, or a mixture thereof. Exemplary solid forms are described in more detail below.

In some embodiments, the present invention provides compound 4 substantially free of impurities. As used herein, the term "substantially free of impurities" means that the compound contains no significant amount of extraneous matter. Such extraneous matter may include excess hydrochloric acid, excess compound A, residual solvents, or any other impurities that may result from the preparation of, and/or isolation of, compound 4. In certain embodiments, at least about 95% by weight of compound 4 is present. In still other embodiments of the invention, at least about 99% by weight of compound 4 is present.

According to one embodiment, compound 4 is present in an amount of at least about weight of the composition. According to another embodiment, compound 4 contains no more than about 3.0 area percent HPLC of total organic impurities and, in certain embodiments, no more than about 1.5 area percent HPLC total organic impurities relative to the total area of the HPLC chromatogram. In other embodiments, compound 4 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 4 is also meant to include all tautomeric forms of compound 4. Additionally, structures depicted here are also meant to include compounds that differ only in the presence of one or more isotopically enriched atoms. For example, compounds having the present structure except for the replacement of hydrogen by deuterium or tritium, or the replacement of a carbon by a 13C- or 14C-enriched carbon are within the scope of this invention.

It has been found that compound 4 can exist in a variety of solid forms. Exemplary such forms include polymorphs such as those described herein.

In certain embodiments, compound 4 is a crystalline solid. In other embodiments, compound 4 is a crystalline solid substantially free of amorphous compound 4. As used herein, the term "substantially free of amorphous compound 4" means that the compound contains no significant amount of amorphous compound 4. In certain embodiments, at least about 95% by weight of crystalline compound 4 is present. In still other embodiments of the invention, at least about 99% by weight of crystalline compound 4 is present.

In some embodiments, compound 4 is amorphous. In some embodiments, compound 4 is amorphous, and is substantially free of crystalline compound 4.

Form A of Compound 4

In some embodiments, Form A of compound 4 has at least 1, 2, 3, 4 or 5 spectral peak(s) selected from the peaks listed in Table 4 below.

TABLE 4

XRPD Peak Positions for Form A of Compound 4

| Position [°2θ][1] | Intensity [%] |
|---|---|
| 7.2 | 5.47 |
| 9.4 | 14.04 |
| 10.5 | 3.06 |
| 10.8 | 5.09 |
| 11.7 | 19.4 |
| 12.2 | 2.52 |
| 13.2 | 39.12 |
| 14.3 | 13.74 |
| 14.9 | 75.47 |
| 15.0 | 10.98 |
| 15.4 | 4.1 |
| 15.9 | 3.33 |
| 16.1 | 62.43 |
| 16.8 | 69.56 |
| 17.4 | 0.71 |
| 17.7 | 0.71 |
| 18.7 | 21.13 |
| 18.8 | 12.61 |
| 19.3 | 1.29 |
| 19.6 | 4.15 |
| 20.4 | 2.34 |
| 21.1 | 6.39 |
| 21.5 | 39.57 |
| 21.7 | 46.52 |
| 22.1 | 20.67 |
| 22.7 | 10.05 |
| 22.7 | 14.69 |
| 23.1 | 11.29 |
| 23.4 | 13.77 |
| 23.5 | 18.22 |
| 23.7 | 33.49 |
| 24.0 | 6.21 |
| 24.2 | 18.86 |
| 24.5 | 100 |
| 25.2 | 7.38 |
| 25.8 | 6.2 |
| 26.1 | 15.98 |
| 26.3 | 7.76 |
| 26.5 | 2.8 |
| 27.1 | 4.13 |
| 27.2 | 4.66 |
| 27.5 | 5.44 |
| 28.7 | 54.32 |
| 29.0 | 37.48 |
| 29.5 | 2.79 |
| 29.8 | 1.24 |
| 30.2 | 3.8 |
| 30.6 | 1.44 |
| 31.0 | 4.32 |
| 31.5 | 9.48 |
| 31.7 | 7.69 |
| 32.0 | 3.05 |
| 32.3 | 11.21 |
| 32.5 | 15.93 |
| 32.9 | 2.31 |
| 33.7 | 0.83 |
| 34.0 | 1.63 |
| 34.4 | 3.62 |
| 34.8 | 0.58 |
| 35.0 | 2.54 |
| 35.6 | 8.89 |
| 36.2 | 1.61 |
| 36.7 | 7.12 |
| 37.2 | 2.36 |
| 38.2 | 3.13 |
| 38.6 | 3.02 |
| 39.0 | 0.44 |
| 39.7 | 3.2 |
| 39.9 | 4.42 |

[1]In this and all subsequent tables, the position 2θ is within ±0.2.

In some embodiments, Form A of compound 4 is characterized in that it has one or more peaks in its X-ray powder diffraction pattern selected from those at about 14.9, about 16.8 and about 24.5 degrees 2-theta. In some embodiments, Form A of compound 4 is characterized in that it has two or more peaks in its X-ray powder diffraction pattern selected from those at about 14.9, about 16.8 and about 24.5 degrees 2-theta. In some embodiments, Form A of compound 4 is characterized in that it has all three peaks in its X-ray powder diffraction pattern selected from those at about 14.9, about 16.8 and about 24.5 degrees 2-theta.

Figure 7:
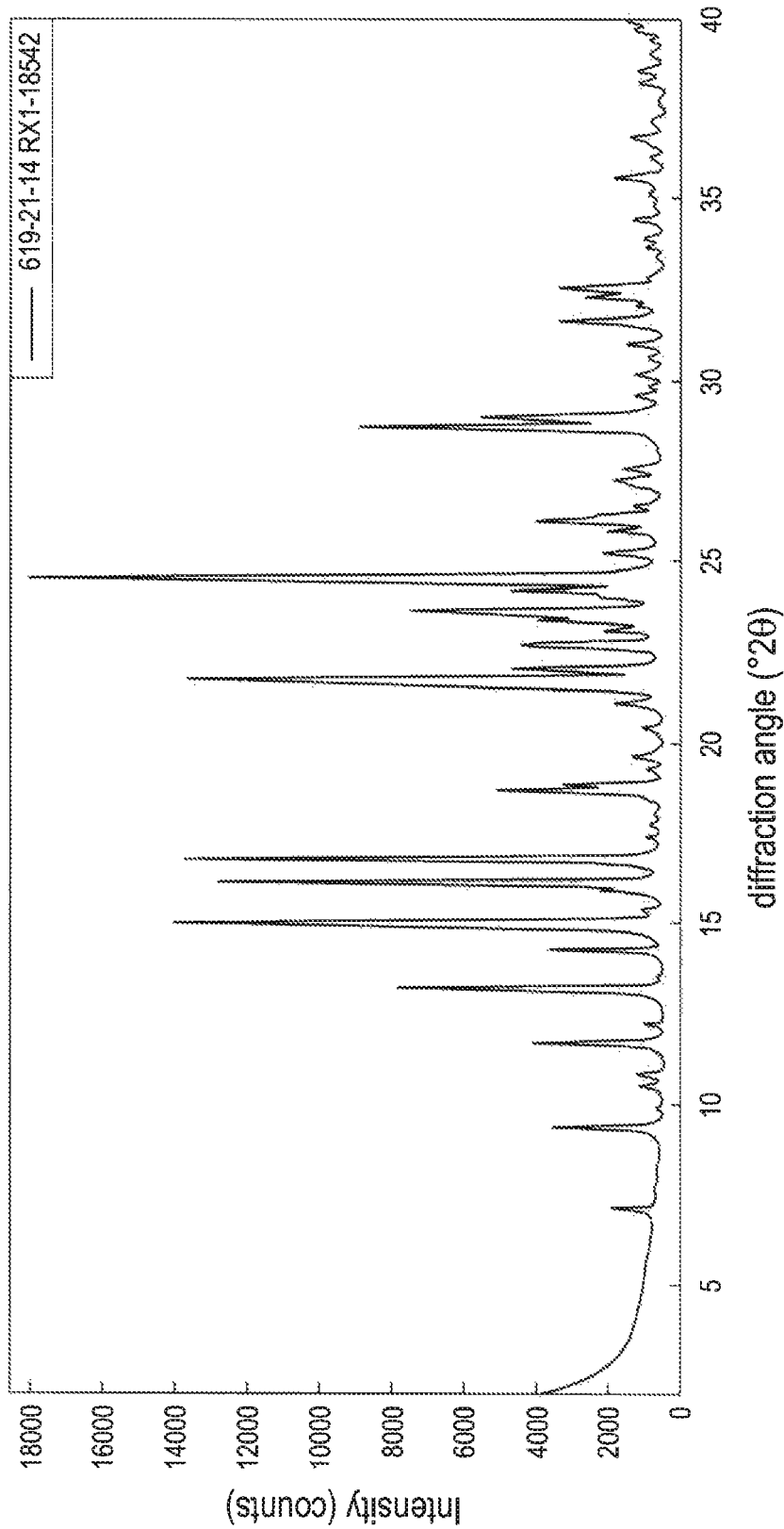
FIG. 7 depicts the XRPD pattern of Compound 4, Form A.

In certain embodiments, the X-ray powder diffraction pattern is substantially similar to the XRPD provided in FIG. 7.

Methods for preparing Form A of compound 4 are described infra.

In some embodiments, the present invention provides compound 4:

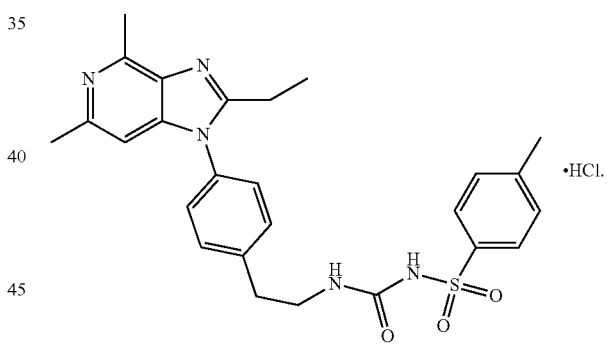

4

In some embodiments, the present invention provides compound 4, wherein said compound is crystalline.

In some embodiments, the present invention provides compound 4, wherein said compound is a crystalline solid substantially free of amorphous compound 4.

In some embodiments, the present invention provides compound 4, wherein said compound is substantially free of impurities.

In some embodiments, the present invention provides compound 4, wherein said compound has one or more peaks in its XRPD selected from those at about 14.9, about 16.8 and about 24.5 degrees 2-theta. In some such embodiments, the present invention provides compound 4, wherein said compound has at least two peaks in its XRPD selected from those at about 14.9, about 16.8 and about 24.5 degrees 2-theta. In some such embodiments, the present invention provides compound 4, wherein said compound is of Form A.

In some embodiments, the present invention provides compound 4, wherein said compound has an XRPD substantially similar to that depicted in FIG. 7.

In some embodiments, the present invention provides a composition comprising compound 4 and a pharmaceutically acceptable carrier or excipient.

In some embodiments, the present invention provides a method of inhibiting, preventing and/or reducing severity of a proliferative disorder associated with prostaglandin EP4 receptor activity in a patient comprising administering to said patient compound 4 or composition thereof.

In some embodiments, the present invention provides a method of treating various conditions in a patient in which prostaglandin EP4 receptor activity is implicated in the pathogenesis, comprising administering to said patient compound 4 or composition thereof. In some such embodiments, the various conditions in a patient in which prostaglandin EP4 receptor activity is implicated in the pathogenesis may include cancer, such as, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

Compound 5 (Xinafoate Salts of Compound A)

According to one embodiment, the present invention provides a xinafoate salt of compound A, represented by compound 5:

It will be appreciated by one of ordinary skill in the art that the 1-hydroxy-2-napthoic acid and compound A are ionically bonded to form compound 5. It is contemplated that compound 5 can exist in a variety of physical forms. For example, compound 5 can be in solution, suspension, or in solid form. In certain embodiments, compound 5 is in solid form. When compound 5 is in solid form, said compound may be amorphous, crystalline, or a mixture thereof. Exemplary solid forms are described in more detail below.

In some embodiments, the present invention provides compound 5 substantially free of impurities. As used herein, the term "substantially free of impurities" means that the compound contains no significant amount of extraneous matter. Such extraneous matter may include excess 1-hydroxy-2-napthoic acid, excess compound A, residual solvents, or any other impurities that may result from the preparation of, and/or isolation of, compound 5. In certain embodiments, at least about 95% by weight of compound 5 is present. In still other embodiments of the invention, at least about 99% by weight of compound 5 is present.

According to one embodiment, compound 5 is present in an amount of at least about 97, 97.5, 98.0, 98.5, 99, 99.5, 99.8 weight percent where the percentages are based on the total weight of the composition. According to another embodiment, compound 5 contains no more than about 3.0 area percent HPLC of total organic impurities and, in certain embodiments, no more than about 1.5 area percent HPLC total organic impurities relative to the total area of the HPLC chromatogram. In other embodiments, compound 5 contains no more than about 1.0% area percent HPLC of any single impurity; no more than about 0.6 area percent HPLC of any single impurity, The structure depicted for compound 5 is also meant to include all tautomeric forms of compound 5. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 5 can exist in a variety of solid forms. Exemplary such forms include polymorphs such as those described herein.

In certain embodiments, compound 5 is a crystalline solid. In other embodiments, compound 5 is a crystalline solid substantially free of amorphous compound 5. As used herein, the term "substantially free of amorphous compound 5" means that the compound contains no significant amount

5

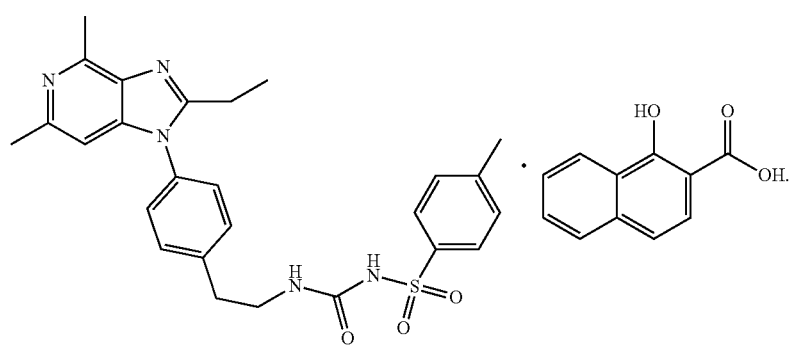

of amorphous compound 5. In certain embodiments, at least about 95% by weight of crystalline compound 5 is present. In still other embodiments of the invention, at least about 99% by weight of crystalline compound 5 is present.

In some embodiments, compound 5 is amorphous. In some embodiments, compound 5 is amorphous, and is substantially free of crystalline compound 5.

Form A of Compound 5

In some embodiments, Form A of compound 5 has at least 1, 2, 3, 4 or 5 spectral peak(s) selected from the peaks listed in Table 5 below.

TABLE 5

XRPD Peak Positions for Form A of Compound 5

| Position [°2θ][1] | Intensity [%] |
|---|---|
| 4.9 | 87.88 |
| 6.7 | 18.75 |
| 7.9 | 3.1 |
| 9.6 | 67.51 |
| 9.8 | 47.62 |
| 11.5 | 12.07 |
| 12.5 | 47.05 |
| 12.7 | 17.56 |
| 13.1 | 20.27 |
| 13.7 | 75.13 |
| 14.4 | 4.76 |
| 15.8 | 82.58 |
| 16.7 | 18.58 |
| 17.5 | 10.62 |
| 19.2 | 13.14 |
| 19.4 | 4.42 |
| 20.4 | 18.65 |
| 20.8 | 6.18 |
| 21.1 | 30.79 |
| 22.8 | 4.56 |
| 23.1 | 23.23 |

TABLE 5-continued

XRPD Peak Positions for Form A of Compound 5

| Position [°2θ][1] | Intensity [%] |
|---|---|
| 24.8 | 35.06 |
| 25.2 | 100 |
| 25.4 | 3.48 |
| 26.0 | 33.08 |
| 26.4 | 13.82 |
| 27.1 | 2.04 |
| 27.8 | 4.15 |
| 29.7 | 9.74 |
| 30.5 | 1.96 |
| 30.0 | 3.94 |
| 31.9 | 2.89 |
| 33.0 | 7.92 |
| 34.2 | 2.1 |
| 37.4 | 1.82 |
| 38.7 | 2.4 |
| 39.4 | 2.46 |

[1]In this and all subsequent tables, the position 2θ is within ±0.2.

In some embodiments, Form A of compound 5 is characterized in that it has one or more peaks in its X-ray powder diffraction pattern selected from those at about 4.9, about 15.8 and about 25.2 degrees 2-theta. In some embodiments, Form A of compound 5 is characterized in that it has two or more peaks in its X-ray powder diffraction pattern selected from those at about 4.9, about 15.8 and about 25.2 degrees 2-theta. In some embodiments, Form A of compound 5 is characterized in that it has all three peaks in its X-ray powder diffraction pattern selected from those at about 4.9, about 15.8 and about 25.2 degrees 2-theta.

Figure 9:
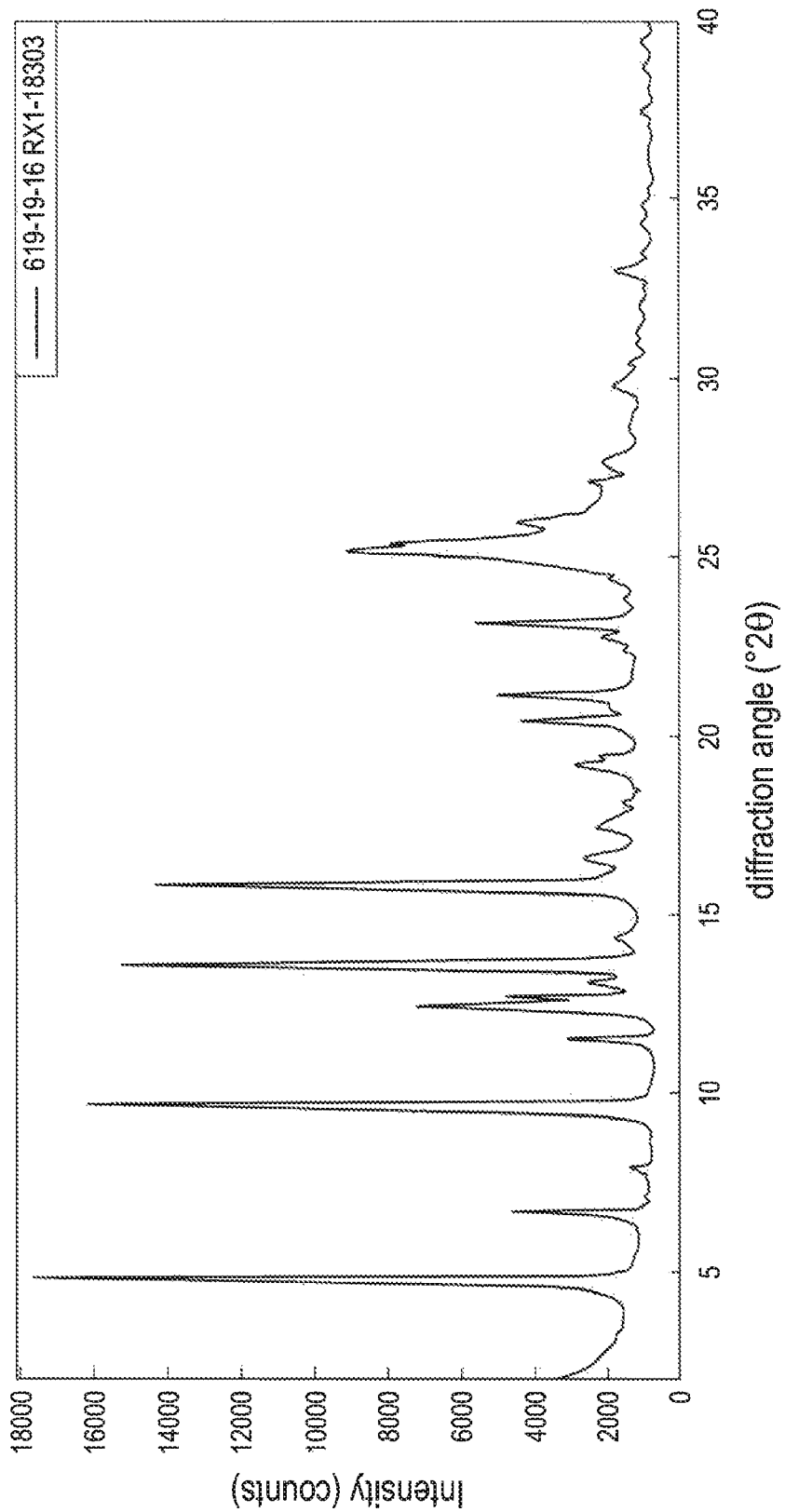
FIG. 9 depicts the XRPD pattern of Compound 5, Form A.

In certain embodiments, the X-ray powder diffraction pattern is substantially similar to the XRPD provided in FIG. 9.

Methods for preparing Form A of compound 5 are described infra.

In some embodiments, the present invention provides compound 5:

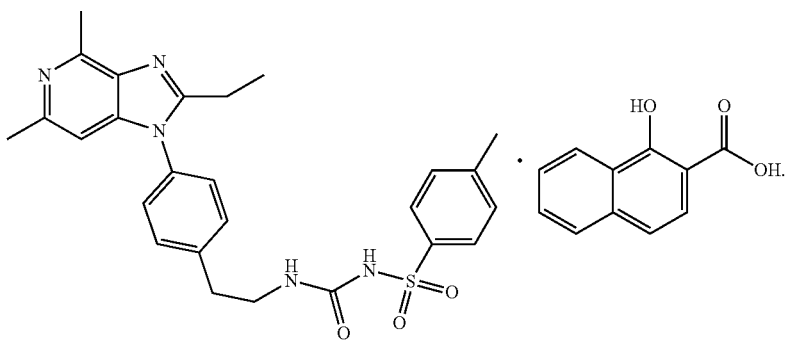

5

In some embodiments, the present invention provides compound 5, wherein said compound is crystalline.

In some embodiments, the present invention provides compound 5, wherein said compound is a crystalline solid substantially free of amorphous compound 5.

In some embodiments, the present invention provides compound 5, wherein said compound is substantially free of impurities.

In some embodiments, the present invention provides compound 5, wherein said compound has one or more peaks in its XRPD selected from those at about 4.9, about 15.8 and about 25.2 degrees 2-theta. In some such embodiments, the present invention provides compound 5, wherein said compound has at least two peaks in its XRPD selected from those at about 4.9, about 15.8 and about 25.2 degrees 2-theta. In some such embodiments, the present invention provides compound 5, wherein said compound is of Form A.

In some embodiments, the present invention provides compound 5, wherein said compound has an XRPD substantially similar to that depicted in FIG. 9.

In some embodiments, the present invention provides a composition comprising compound 5 and a pharmaceutically acceptable carrier or excipient.

In some embodiments, the present invention provides a method of inhibiting, preventing and/or reducing severity of a proliferative disorder associated with prostaglandin EP4 receptor activity in a patient comprising administering to said patient compound 5 or composition thereof.

In some embodiments, the present invention provides a method of treating various conditions in a patient in which prostaglandin EP4 receptor activity is implicated in the pathogenesis, comprising administering to said patient compound 5 or composition thereof. In some such embodiments, the various conditions in a patient in which prostaglandin EP4 receptor activity is implicated in the pathogenesis may include cancer, such as, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

Compound 6 (Isethionate Salts of Compound A)

According to one embodiment, the present invention provides an isethionate salt of compound A, represented by compound 6:

It will be appreciated by one of ordinary skill in the art that the isethionic acid and compound A are ionically bonded to form compound 6. It is contemplated that compound 6 can exist in a variety of physical forms. For example, compound 6 can be in solution, suspension, or in solid form. In certain embodiments, compound 6 is in solid form. When compound 6 is in solid form, said compound may be amorphous, crystalline, or a mixture thereof. Exemplary solid forms are described in more detail below.

In some embodiments, the present invention provides compound 6 substantially free of impurities. As used herein, the term "substantially free of impurities" means that the compound contains no significant amount of extraneous matter. Such extraneous matter may include excess isethionic acid, excess compound A, residual solvents, or any other impurities that may result from the preparation of, and/or isolation of, compound 6. In certain embodiments, at least about 95% by weight of compound 6 is present. In still other embodiments of the invention, at least about 99% by weight of compound 6 is present.

According to one embodiment, compound 6 is present in an amount of at least about 97, 97.5, 98.0, 98.5, 99, 99.5, 99.8 weight percent where the percentages are based on the total weight of the composition. According to another embodiment, compound 6 contains no more than about 3.0 area percent HPLC of total organic impurities and, in certain embodiments, no more than about 1.5 area percent HPLC total organic impurities relative to the total area of the HPLC chromatogram. In other embodiments, compound 6 contains no more than about 1.0% area percent HPLC of any single impurity; no more than about 0.6 area percent HPLC of any single impurity, The structure depicted for compound 6 is also meant to include all tautomeric forms of compound 6. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 6 can exist in a variety of solid forms. Exemplary such forms include polymorphs such as those described herein.

In certain embodiments, compound 6 is a crystalline solid. In other embodiments, compound 6 is a crystalline solid substantially free of amorphous compound 6. As used herein, the term "substantially free of amorphous compound 6" means that the compound contains no significant amount of amorphous compound 67. In certain embodiments, at least about 95% by weight of crystalline compound 6 is present. In still other embodiments of the invention, at least about 99% by weight of crystalline compound 6 is present.

In some embodiments, compound 6 is amorphous. In some embodiments, compound 6 is amorphous, and is substantially free of crystalline compound 6.

Form A of Compound 6

In some embodiments, Form A of compound 6 has at least 1, 2, 3, 4 or 5 spectral peak(s) selected from the peaks listed in Table 6 below.

TABLE 6

XRPD Peak Positions for Form A of Compound 6

| Position [°2θ][1] | Intensity [%] |
|---|---|
| 5.8 | 99.63 |
| 7.0 | 12.91 |
| 7.2 | 16.44 |

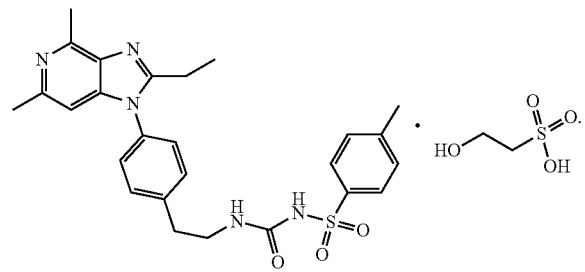

TABLE 6-continued

XRPD Peak Positions for Form A of Compound 6

| Position [°2θ][1] | Intensity [%] |
|---|---|
| 7.8 | 10.03 |
| 9.8 | 40.29 |
| 10.7 | 6.83 |
| 11.6 | 16.99 |
| 12.1 | 17.66 |
| 12.7 | 35.75 |
| 12.8 | 11.99 |
| 14.0 | 15.11 |
| 14.3 | 65.63 |
| 15.2 | 100 |
| 15.6 | 32.34 |
| 17.6 | 48.58 |
| 18.3 | 11.38 |
| 18.7 | 4.78 |
| 19.1 | 38.89 |
| 19.7 | 40.82 |
| 19.9 | 51.88 |
| 20.6 | 22.08 |
| 21.2 | 68.69 |
| 22.1 | 88.96 |
| 22.6 | 42.71 |
| 23.0 | 7.9 |
| 23.3 | 26.47 |
| 24.3 | 12.66 |
| 24.9 | 82.85 |
| 25.4 | 57.98 |
| 26.9 | 39.57 |
| 28.0 | 12.39 |
| 28.7 | 16.02 |
| 28.9 | 3.38 |
| 29.2 | 17.48 |
| 29.6 | 3.46 |
| 29.8 | 3 |
| 30.6 | 12.17 |
| 32.4 | 4.75 |
| 32.7 | 8.41 |
| 33.9 | 6.03 |
| 34.5 | 3.21 |
| 35.7 | 4.74 |
| 36.8 | 3.69 |

[1]In this and all subsequent tables, the position 2θ is within ±0.2.

In some embodiments, Form A of compound 6 is characterized in that it has one or more peaks in its X-ray powder diffraction pattern selected from those at about 5.8, about 15.2 and about 22.1 degrees 2-theta. In some embodiments, Form A of compound 6 is characterized in that it has two or more peaks in its X-ray powder diffraction pattern selected from those at about 5.8, about 15.2 and about 22.1 degrees 2-theta. In some embodiments, Form A of compound 6 is characterized in that it has all three peaks in its X-ray powder diffraction pattern selected from those at about 5.8, about 15.2 and about 22.1 degrees 2-theta.

Figure 11:
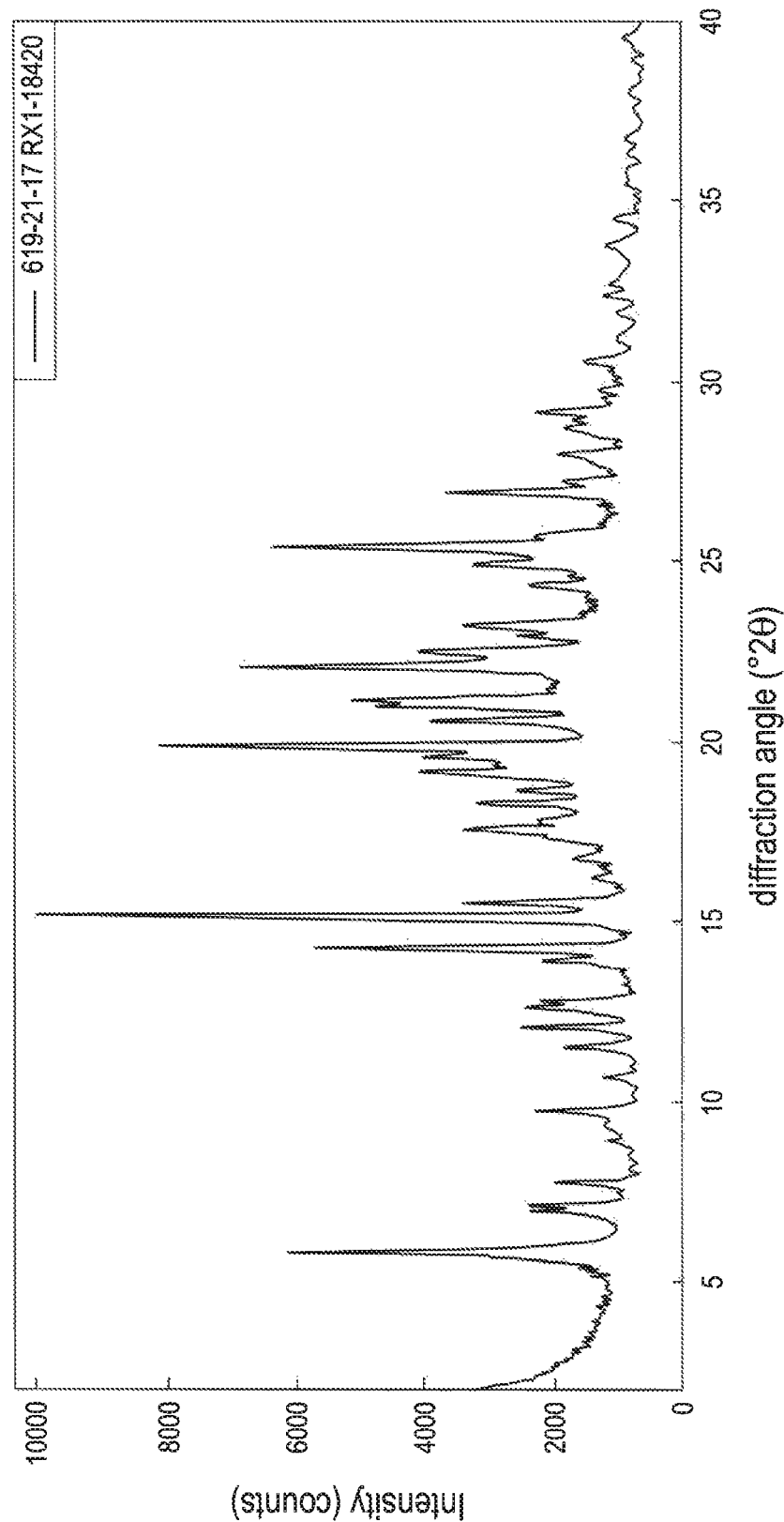
FIG. 11 depicts the XRPD pattern of Compound 6, Form A.

In certain embodiments, the X-ray powder diffraction pattern is substantially similar to the XRPD provided in FIG. 11.

Methods for preparing Form A of compound 6 are described infra.

In some embodiments, the present invention provides compound 6:

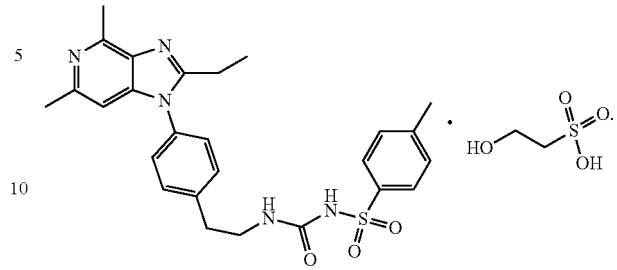

6

In some embodiments, the present invention provides compound 6, wherein said compound is crystalline.

In some embodiments, the present invention provides compound 6, wherein said compound is a crystalline solid substantially free of amorphous compound 6.

In some embodiments, the present invention provides compound 6, wherein said compound is substantially free of impurities.

In some embodiments, the present invention provides compound 6, wherein said compound has one or more peaks in its XRPD selected from those at about 5.8, about 15.2 and about 22.1 degrees 2-theta. In some such embodiments, the present invention provides compound 6, wherein said compound has at least two peaks in its XRPD selected from those at about 5.8, about 15.2 and about 22.1 degrees 2-theta. In some such embodiments, the present invention provides compound 6, wherein said compound is of Form A.

In some embodiments, the present invention provides compound 6, wherein said compound has an XRPD substantially similar to that depicted in FIG. 11.

In some embodiments, the present invention provides a composition comprising compound 6 and a pharmaceutically acceptable carrier or excipient.

In some embodiments, the present invention provides a method of inhibiting, preventing and/or reducing severity of a proliferative disorder associated with prostaglandin EP4 receptor activity in a patient comprising administering to said patient compound 6 or composition thereof.

In some embodiments, the present invention provides a method of treating various conditions in a patient in which prostaglandin EP4 receptor activity is implicated in the pathogenesis, comprising administering to said patient compound 6 or composition thereof. In some such embodiments, the various conditions in a patient in which prostaglandin EP4 receptor activity is implicated in the pathogenesis may include cancer, such as, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

Compound 7 (Mesylate Salts of Compound A)

According to one embodiment, the present invention provides a mesylate salt of compound A, represented by compound 7:

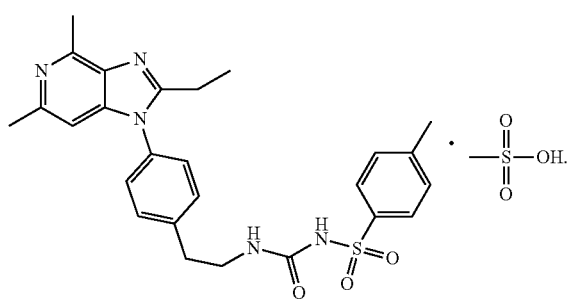

It will be appreciated by one of ordinary skill in the art that methanesulfonic acid and compound A are ionically bonded to form compound 7. It is contemplated that compound 7 can exist in a variety of physical forms. For example, compound 7 can be in solution, suspension, or in solid form. In certain embodiments, compound 7 is in solid form. When compound 7 is in solid form, said compound may be amorphous, crystalline, or a mixture thereof. Exemplary solid forms are described in more detail below.

In some embodiments, the present invention provides compound 7 substantially free of impurities. As used herein, the term "substantially free of impurities" means that the compound contains no significant amount of extraneous matter. Such extraneous matter may include excess methanesulfonic acid, excess compound A, residual solvents, or any other impurities that may result from the preparation of, and/or isolation of, compound 7. In certain embodiments, at least about 95% by weight of compound 7 is present. In still other embodiments of the invention, at least about 99% by weight of compound 7 is present.

According to one embodiment, compound 7 is present in an amount of at least about weight of the composition. According to another embodiment, compound 7 contains no more than about 3.0 area percent HPLC of total organic impurities and, in certain embodiments, no more than about 1.5 area percent HPLC total organic impurities relative to the total area of the HPLC chromatogram. In other embodiments, compound 7 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 7 is also meant to include all tautomeric forms of compound 7. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}C$- or $^{14}C$-enriched carbon are within the scope of this invention.

It has been found that compound 7 can exist in a variety of solid forms. Exemplary such forms include polymorphs such as those described herein.

In certain embodiments, compound 7 is a crystalline solid. In other embodiments, compound 7 is a crystalline solid substantially free of amorphous compound 7. As used herein, the term "substantially free of amorphous compound 7" means that the compound contains no significant amount of amorphous compound 7. In certain embodiments, at least about 95% by weight of crystalline compound 7 is present. In still other embodiments of the invention, at least about 99% by weight of crystalline compound 7 is present.

In some embodiments, compound 7 is amorphous. In some embodiments, compound 7 is amorphous, and is substantially free of crystalline compound 7.

Form A of Compound 7

In some embodiments, Form A of compound 7 has at least 1, 2, 3, 4 or 5 spectral peak(s) selected from the peaks listed in Table 7 below.

TABLE 7

XRPD Peak Positions for Form A of Compound 7

| Position [°2θ][1] | Intensity [%] |
|---|---|
| 7.0 | 33.31 |
| 7.8 | 7.24 |
| 10.1 | 8.16 |
| 10.7 | 36.62 |
| 14.0 | 37.89 |
| 14.5 | 5.87 |
| 15.6 | 42.54 |
| 16.4 | 15.77 |
| 16.7 | 1.17 |
| 17.4 | 17.97 |
| 17.6 | 1.16 |
| 17.8 | 11.14 |
| 18.6 | 22 |
| 19.1 | 100 |
| 19.6 | 14.84 |
| 19.7 | 11.11 |
| 20.3 | 4.16 |
| 20.6 | 8.33 |
| 20.8 | 1.07 |
| 21.1 | 1.85 |
| 21.5 | 10.49 |
| 221 | 20 |
| 22.5 | 73.06 |
| 22.8 | 21.05 |
| 23.1 | 10.01 |
| 23.5 | 14 |
| 23.7 | 16 |
| 25.0 | 4.63 |
| 26.0 | 5.61 |
| 26.1 | 16.41 |
| 26.7 | 15.55 |
| 27.1 | 8.71 |
| 27.5 | 3.04 |
| 28.0 | 11.91 |
| 28.4 | 7.99 |
| 29.5 | 8.34 |
| 30.7 | 5.69 |
| 31.3 | 2.68 |
| 31.9 | 3.32 |
| 32.0 | 2.89 |

TABLE 7-continued

XRPD Peak Positions for Form A of Compound 7

| Position [°2θ][1] | Intensity [%] |
|---|---|
| 32.5 | 3.53 |
| 32.9 | 4.83 |
| 33.7 | 0.87 |
| 36.6 | 7.2 |
| 37.2 | 2.62 |
| 37.6 | 4.83 |
| 39.1 | 1.38 |

[1] In this and all subsequent tables, the position 2θ is within ±0.2.

In some embodiments, Form A of compound 7 is characterized in that it has one or more peaks in its X-ray powder diffraction pattern selected from those at about 15.6, about 19.1 and about 22.5 degrees 2-theta. In some embodiments, Form A of compound 7 is characterized in that it has two or more peaks in its X-ray powder diffraction pattern selected from those at about 15.6, about 19.1 and about 22.5 degrees 2-theta. In some embodiments, Form A of compound 7 is characterized in that it has all three peaks in its X-ray powder diffraction pattern selected from those at about 15.6, about 19.1 and about 22.5 degrees 2-theta.

Figure 13:
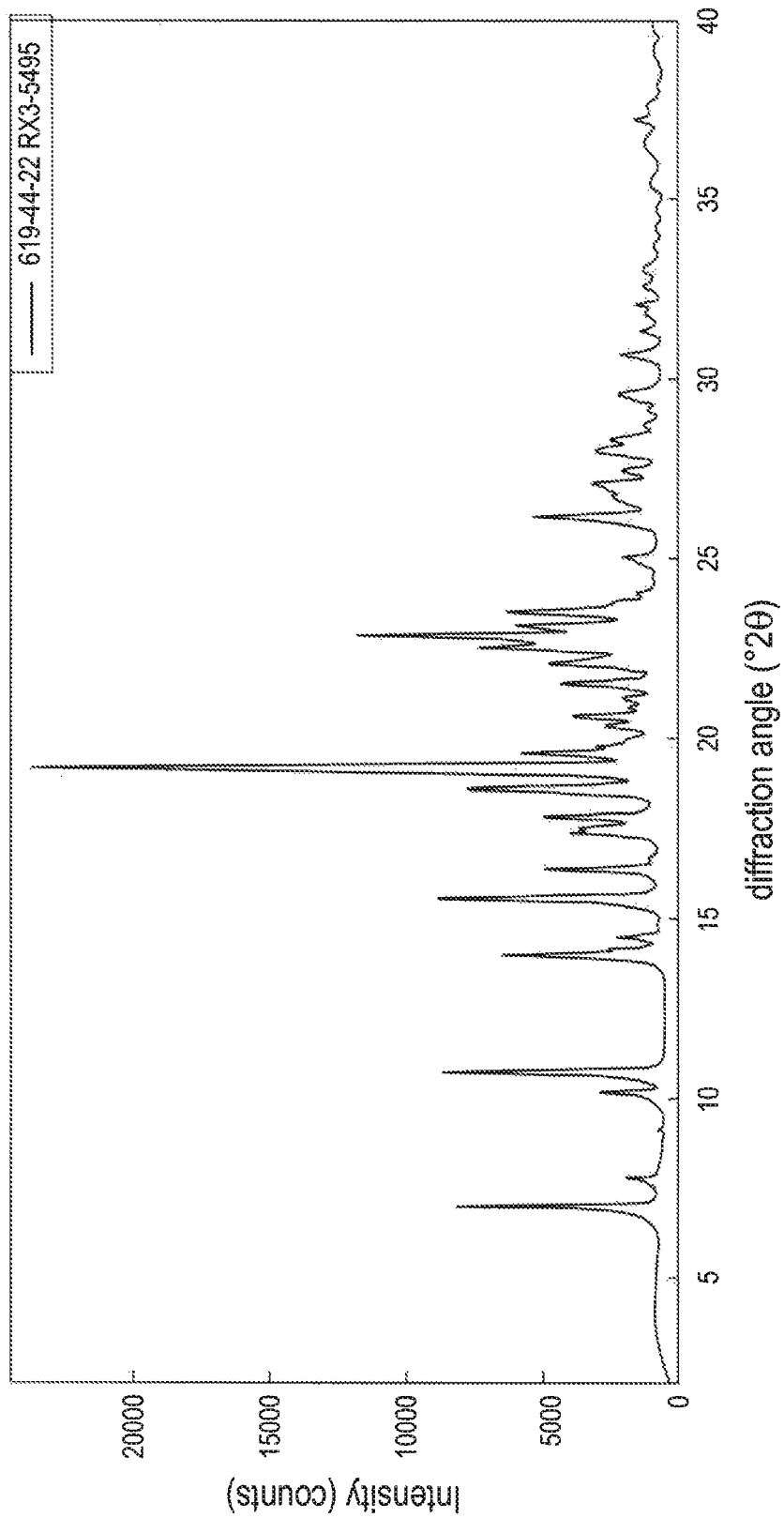
FIG. 13 depicts the XRPD pattern of Compound 7, Form A.

In certain embodiments, the X-ray powder diffraction pattern is substantially similar to the XRPD provided in FIG. 13.

Methods for preparing Form A of compound 7 are described infra.

In some embodiments, the present invention provides compound 7:

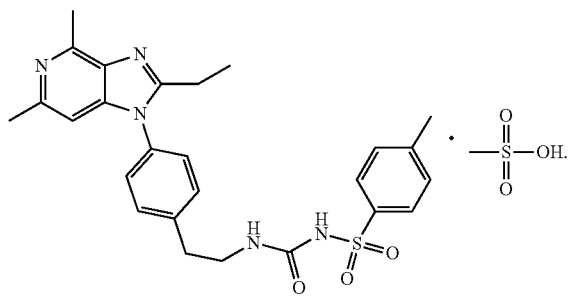

7

In some embodiments, the present invention provides compound 7, wherein said compound is crystalline.

In some embodiments, the present invention provides compound 7, wherein said compound is a crystalline solid substantially free of amorphous compound 7.

In some embodiments, the present invention provides compound 7, wherein said compound is substantially free of impurities.

In some embodiments, the present invention provides compound 7, wherein said compound has one or more peaks in its XRPD selected from those at about 15.6, about 19.1 and about 22.5 degrees 2-theta. In some such embodiments, the present invention provides compound 7, wherein said compound has at least two peaks in its XRPD selected from those at about 15.6, about 19.1 and about 22.5 degrees 2-theta. In some such embodiments, the present invention provides compound 7, wherein said compound is of Form A.

In some embodiments, the present invention provides compound 7, wherein said compound has an XRPD substantially similar to that depicted in FIG. 13.

In some embodiments, the present invention provides a composition comprising compound 7 and a pharmaceutically acceptable carrier or excipient.

In some embodiments, the present invention provides a method of inhibiting, preventing and/or reducing severity of a proliferative disorder associated with prostaglandin EP4 receptor activity in a patient comprising administering to said patient compound 7 or composition thereof.

In some embodiments, the present invention provides a method of treating various conditions in a patient in which prostaglandin EP4 receptor activity is implicated in the pathogenesis, comprising administering to said patient compound 7 or composition thereof. In some such embodiments, the various conditions in a patient in which prostaglandin EP4 receptor activity is implicated in the pathogenesis may include cancer, such as, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

Compound 8 (Napadisylate Salts of Compound A)

According to one embodiment, the present invention provides a napthalene-1,5-disulfonic acid salt of compound A, represented by compound 8:

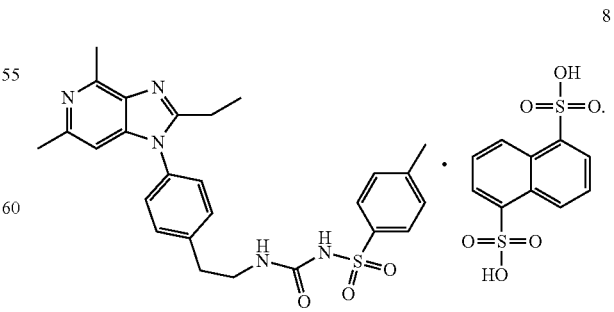

8

It will be appreciated by one of ordinary skill in the art that the napthalene-1,5-disulfonic acid and compound A are ionically bonded to form compound 8. It is contemplated that compound 8 can exist in a variety of physical forms. For example, compound 8 can be in solution, suspension, or in solid form. In certain embodiments, compound 8 is in solid form. When compound 8 is in solid form, said compound may be amorphous, crystalline, or a mixture thereof. Exemplary solid forms are described in more detail below.

In some embodiments, the present invention provides compound 8 substantially free of impurities. As used herein, the term "substantially free of impurities" means that the compound contains no significant amount of extraneous matter. Such extraneous matter may include excess napthalene-1,5-disulfonic acid, excess compound A, residual solvents, or any other impurities that may result from the preparation of, and/or isolation of, compound 8. In certain embodiments, at least about 95% by weight of compound 8 is present. In still other embodiments of the invention, at least about 99% by weight of compound 8 is present.

According to one embodiment, compound 8 is present in an amount of at least about 97, 97.5, 98.0, 98.5, 99, 99.5, 99.8 weight percent where the percentages are based on the total weight of the composition. According to another embodiment, compound 8 contains no more than about 3.0 area percent HPLC of total organic impurities and, in certain embodiments, no more than about 1.5 area percent HPLC total organic impurities relative to the total area of the HPLC chromatogram. In other embodiments, compound 8 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 8 is also meant to include all tautomeric forms of compound 8. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 8 can exist in a variety of solid forms. Exemplary such forms include polymorphs such as those described herein.

In certain embodiments, compound 8 is a crystalline solid. In other embodiments, compound 8 is a crystalline solid substantially free of amorphous compound 8. As used herein, the term "substantially free of amorphous compound 8" means that the compound contains no significant amount of amorphous compound 8. In certain embodiments, at least about 95% by weight of crystalline compound 8 is present. In still other embodiments of the invention, at least about 99% by weight of crystalline compound 8 is present.

In some embodiments, compound 8 is amorphous. In some embodiments, compound 8 is amorphous, and is substantially free of crystalline compound 8.

Form A of Compound 8

In some embodiments, Form A of compound 8 has at least 1, 2, 3, 4 or 5 spectral peak(s) selected from the peaks listed in Table 8 below.

TABLE 8

XRPD Peak Positions for Form A of Compound 8

| Position [°2θ][1] | Intensity [%] |
| --- | --- |
| 6.3 | 5.71 |
| 6.8 | 52.76 |
| 7.5 | 6.57 |
| 9.9 | 4.1 |
| 10.7 | 29.64 |
| 11.0 | 47.27 |
| 12.1 | 9.42 |
| 12.8 | 16.63 |
| 13.5 | 93.6 |
| 14.0 | 87.33 |
| 16.1 | 15.56 |
| 17.4 | 2.9 |
| 17.7 | 9.64 |
| 18.4 | 38.49 |
| 18.8 | 4.14 |
| 19.1 | 2.75 |
| 20.0 | 16.92 |
| 20.4 | 45.39 |
| 20.9 | 7.25 |
| 21.7 | 100 |
| 22.6 | 12.99 |
| 22.9 | 2.82 |
| 23.6 | 19.17 |
| 24.2 | 45.45 |
| 25.1 | 32.36 |
| 26.6 | 34.47 |
| 27.5 | 12.55 |
| 28.1 | 4.61 |
| 29.2 | 9.81 |
| 29.9 | 27.75 |
| 30.4 | 13.37 |
| 33.8 | 3.17 |
| 34.8 | 3.29 |
| 36.8 | 17.43 |
| 38.7 | 2.36 |

[1]In this and all subsequent tables, the position 2θ is within ±0.2.

In some embodiments, Form A of compound 8 is characterized in that it has one or more peaks in its X-ray powder diffraction pattern selected from those at about 13.5, about 14.0 and about 21.7 degrees 2-theta. In some embodiments, Form A of compound 8 is characterized in that it has two or more peaks in its X-ray powder diffraction pattern selected from those at about 13.5, about 14.0 and about 21.7 degrees 2-theta. In some embodiments, Form A of compound 8 is characterized in that it has all three peaks in its X-ray powder diffraction pattern selected from those at about 13.5, about 14.0 and about 21.7 degrees 2-theta.

Figure 15:
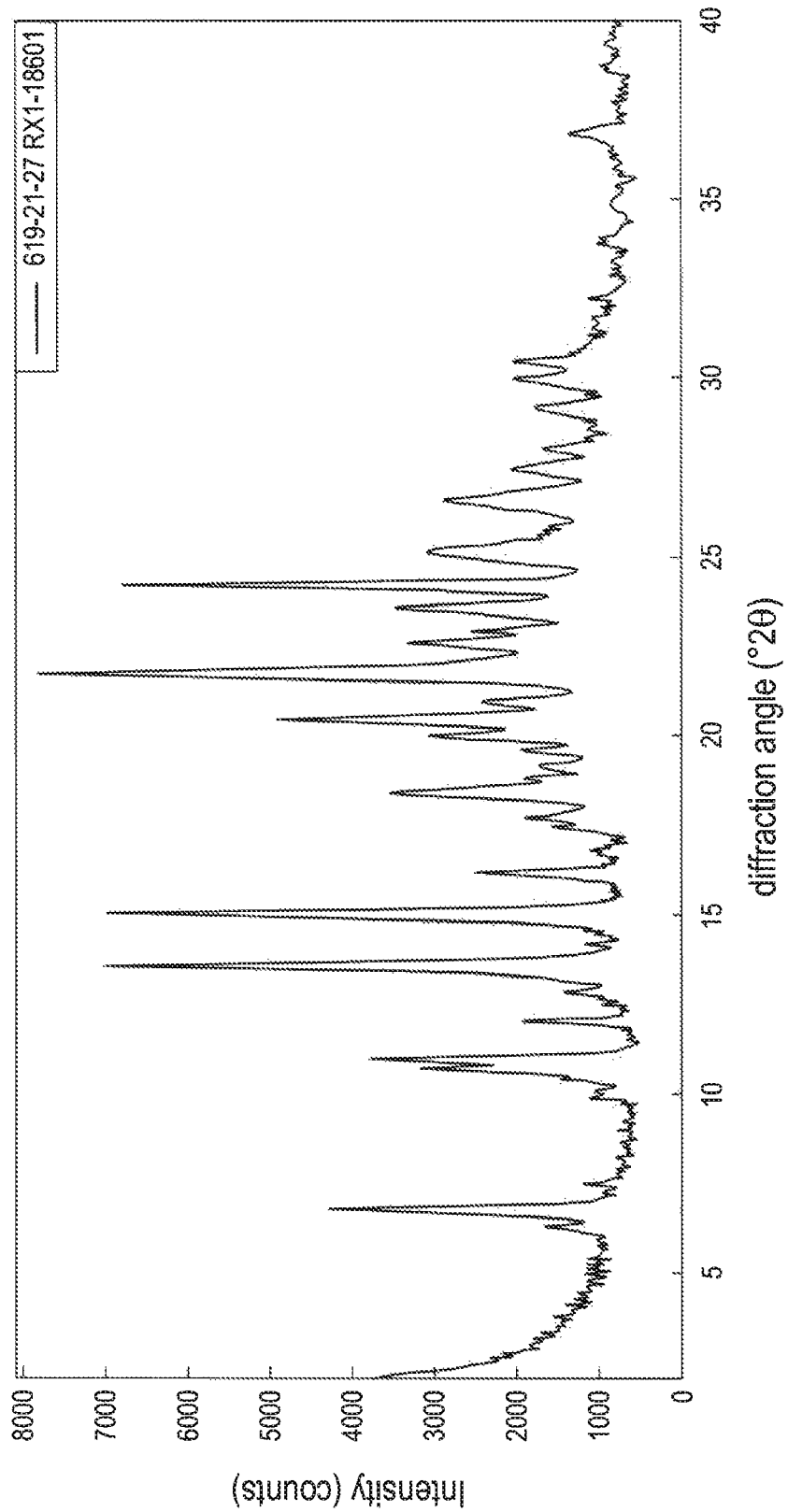
FIG. 15 depicts the XRPD pattern of Compound 8, Form A.

In certain embodiments, the X-ray powder diffraction pattern is substantially similar to the XRPD provided in FIG. 15.

Methods for preparing Form A of compound 8 are described infra.

In some embodiments, the present invention provides compound 8:

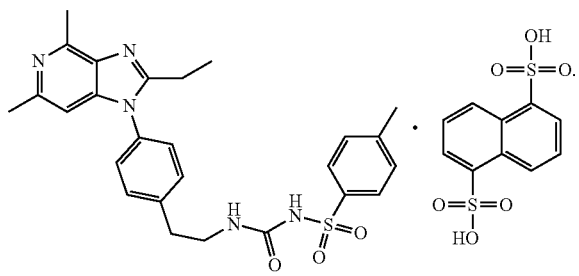

In some embodiments, the present invention provides compound 8, wherein said compound is crystalline.

In some embodiments, the present invention provides compound 8, wherein said compound is a crystalline solid substantially free of amorphous compound 8.

In some embodiments, the present invention provides compound 8, wherein said compound is substantially free of impurities.

In some embodiments, the present invention provides compound 8, wherein said compound has one or more peaks in its XRPD selected from those at about 13.5, about 14.0 and about 21.7 degrees 2-theta. In some such embodiments, the present invention provides compound 8, wherein said compound has at least two peaks in its XRPD selected from those at about 13.5, about 14.0 and about 21.7 degrees 2-theta. In some such embodiments, the present invention provides compound 8, wherein said compound is of Form A.

In some embodiments, the present invention provides compound 8, wherein said compound has an XRPD substantially similar to that depicted in FIG. 15.

In some embodiments, the present invention provides a composition comprising compound 8 and a pharmaceutically acceptable carrier or excipient.

In some embodiments, the present invention provides a method of inhibiting, preventing and/or reducing severity of a proliferative disorder associated with prostaglandin EP4 receptor activity in a patient comprising administering to said patient compound 8 or composition thereof.

In some embodiments, the present invention provides a method of treating various conditions in a patient in which prostaglandin EP4 receptor activity is implicated in the pathogenesis, comprising administering to said patient compound 8 or composition thereof. In some such embodiments, the various conditions in a patient in which prostaglandin EP4 receptor activity is implicated in the pathogenesis may include cancer, such as, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

Compound 9 (Oxalate Salts of Compound A)

According to one embodiment, the present invention provides an oxalate salt of compound A, represented by compound 9:

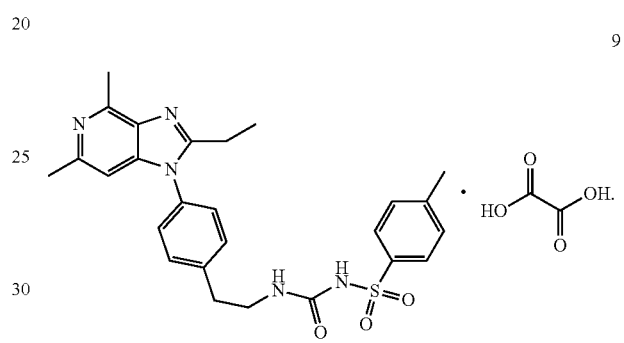

It will be appreciated by one of ordinary skill in the art that the oxalic acid and compound A are ionically bonded to form compound 9. It is contemplated that compound 9 can exist in a variety of physical forms. For example, compound 9 can be in solution, suspension, or in solid form. In certain embodiments, compound 9 is in solid form. When compound 9 is in solid form, said compound may be amorphous, crystalline, or a mixture thereof. Exemplary solid forms are described in more detail below.

In some embodiments, the present invention provides compound 9 substantially free of impurities. As used herein, the term "substantially free of impurities" means that the compound contains no significant amount of extraneous matter. Such extraneous matter may include excess oxalic acid, excess compound A, residual solvents, or any other impurities that may result from the preparation of, and/or isolation of, compound 9. In certain embodiments, at least about 95% by weight of compound 9 is present. In still other embodiments of the invention, at least about 99% by weight of compound 9 is present.

According to one embodiment, compound 9 is present in an amount of at least about 97, 97.5, 98.0, 98.5, 99, 99.5, 99.8 weight percent where the percentages are based on the total weight of the composition. According to another embodiment, compound 9 contains no more than about 3.0 area percent HPLC of total organic impurities and, in certain embodiments, no more than about 1.5 area percent HPLC total organic impurities relative to the total area of the HPLC chromatogram. In other embodiments, compound 9 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 9 is also meant to include all tautomeric forms of compound 9. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 9 can exist in a variety of solid forms. Exemplary such forms include polymorphs such as those described herein.

In certain embodiments, compound 9 is a crystalline solid. In other embodiments, compound 9 is a crystalline solid substantially free of amorphous compound 9. As used herein, the term "substantially free of amorphous compound 9" means that the compound contains no significant amount of amorphous compound 9. In certain embodiments, at least about 95% by weight of crystalline compound 9 is present. In still other embodiments of the invention, at least about 99% by weight of crystalline compound 9 is present.

In some embodiments, compound 9 is amorphous. In some embodiments, compound 9 is amorphous, and is substantially free of crystalline compound 9.

Form A of Compound 9

In some embodiments, Form A of compound 9 has at least 1, 2, 3, 4 or 5 spectral peak(s) selected from the peaks listed in Table 9 below.

TABLE 9

XRPD Peak Positions for Form A of Compound 9

| Position [°2θ][1] | Intensity [%] |
|---|---|
| 6.1 | 32.14 |
| 7.7 | 42.15 |
| 9.1 | 17.81 |
| 9.9 | 5.89 |
| 11.5 | 21.71 |
| 11.8 | 5.47 |
| 12.2 | 5.3 |
| 12.7 | 3.71 |
| 13.7 | 9.37 |
| 14.2 | 4.59 |
| 15.6 | 36.05 |
| 16.6 | 100 |
| 17.2 | 27.97 |
| 17.5 | 42.56 |
| 18.3 | 14.14 |
| 19.0 | 11.11 |
| 20.5 | 6.38 |
| 21.6 | 20.16 |
| 22.1 | 40.11 |
| 22.7 | 38.26 |
| 23.2 | 43.12 |
| 23.8 | 16.45 |
| 24.7 | 22.41 |
| 26.2 | 2.12 |
| 26.9 | 28.09 |
| 27.5 | 14.1 |
| 28.5 | 3.08 |
| 30.3 | 13.04 |
| 31.0 | 8.51 |
| 32.6 | 1.99 |

[1]In this and all subsequent tables, the position 2θ is within ±0.2.

In some embodiments, Form A of compound 9 is characterized in that it has one or more peaks in its X-ray powder diffraction pattern selected from those at about 16.6, about 17.5 and about 23.2 degrees 2-theta. In some embodiments, Form A of compound 9 is characterized in that it has two or more peaks in its X-ray powder diffraction pattern selected from those at about 16.6, about 17.5 and about 23.2 degrees 2-theta. In some embodiments, Form A of compound 9 is characterized in that it has all three peaks in its X-ray powder diffraction pattern selected from those at about 16.6, about 17.5 and about 23.2 degrees 2-theta.

Figure 17:
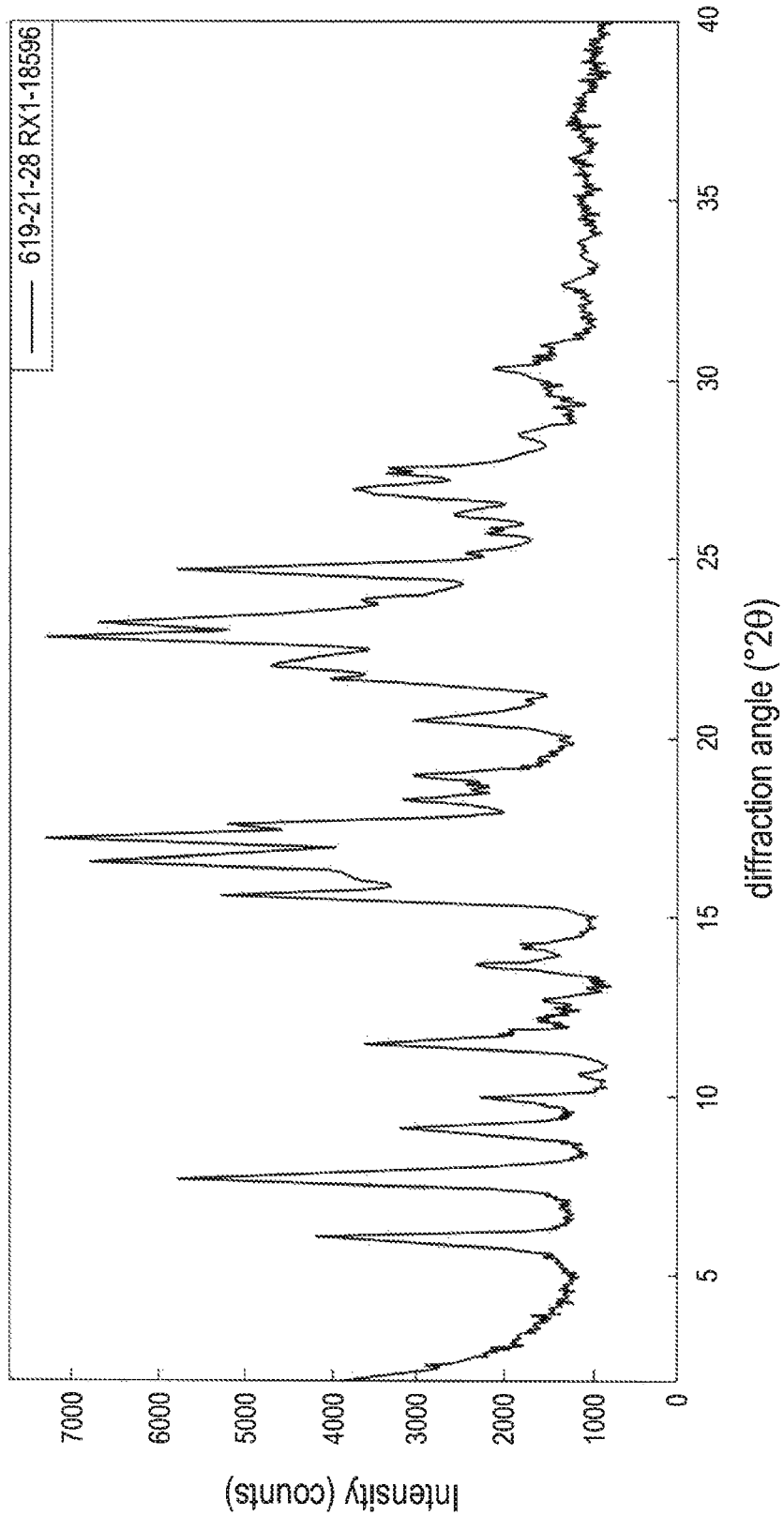
FIG. 17 depicts the XRPD pattern of Compound 9, Form A.

In certain embodiments, the X-ray powder diffraction pattern is substantially similar to the XRPD provided in FIG. 17.

Methods for preparing Form A of compound 9 are described infra.

In some embodiments, the present invention provides compound 9:

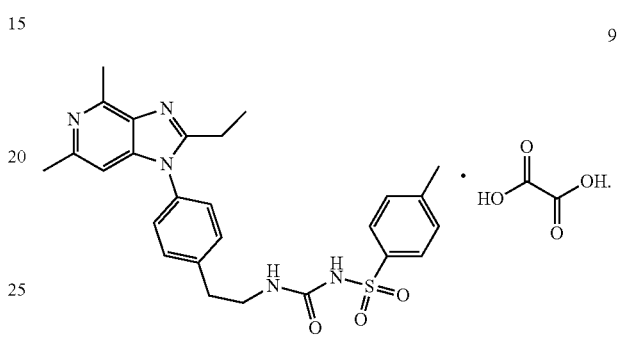

9

In some embodiments, the present invention provides compound 9, wherein said compound is crystalline.

In some embodiments, the present invention provides compound 9, wherein said compound is a crystalline solid substantially free of amorphous compound 9.

In some embodiments, the present invention provides compound 9, wherein said compound is substantially free of impurities.

In some embodiments, the present invention provides compound 9, wherein said compound has one or more peaks in its XRPD selected from those at about 16.6, about 17.5 and about 23.2 degrees 2-theta. In some such embodiments, the present invention provides compound 9, wherein said compound has at least two peaks in its XRPD selected from those at about 16.6, about 17.5 and about 23.2 degrees 2-theta. In some such embodiments, the present invention provides compound 9, wherein said compound is of Form A.

In some embodiments, the present invention provides compound 9, wherein said compound has an XRPD substantially similar to that depicted in FIG. 17.

In some embodiments, the present invention provides a composition comprising compound 9 and a pharmaceutically acceptable carrier or excipient.

In some embodiments, the present invention provides a method of inhibiting, preventing and/or reducing severity of a proliferative disorder associated with prostaglandin EP4 receptor activity in a patient comprising administering to said patient compound 9 or composition thereof.

In some embodiments, the present invention provides a method of treating various conditions in a patient in which prostaglandin EP4 receptor activity is implicated in the pathogenesis, comprising administering to said patient compound 9 or composition thereof. In some such embodiments, the various conditions in a patient in which prostaglandin EP4 receptor activity is implicated in the pathogenesis may include cancer, such as, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma.

Compound 10 (Cinnamic Acid Co-Crystals of Compound A)

According to one embodiment, the present invention provides a cinnamic acid co-crystal of compound A, represented by compound 10:

about 95% by weight of compound 10 is present. In still other embodiments of the invention, at least about 99% by weight of compound 10 is present.

According to one embodiment, compound 10 is present in an amount of at least about weight of the composition. According to another embodiment, compound 10 contains no more than about 3.0 area percent HPLC of total organic impurities and, in certain embodiments, no more than about 1.5 area percent HPLC total organic impurities relative to the total area of the HPLC chromatogram. In other embodiments, compound 10 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 10 is also meant to include all tautomeric forms of compound 10. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

It has been found that compound 10 can exist in a variety of solid forms. Exemplary such forms include polymorphs such as those described herein.

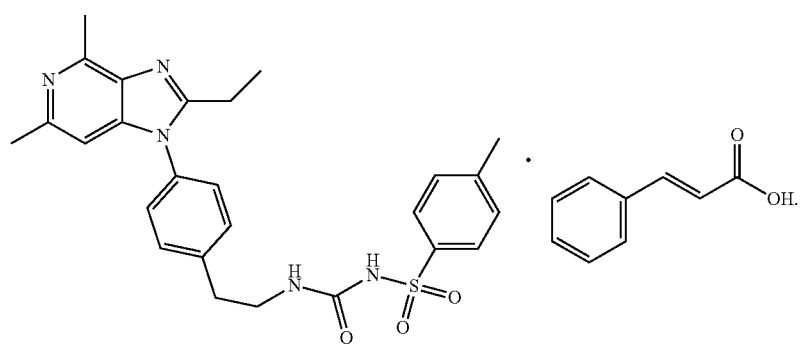

10

It will be appreciated by one of ordinary skill in the art that the cinnamic acid and compound A are bonded via van der waals and pi-pi interactions, among others, to form compound 10. It is contemplated that compound 10 can exist in a variety of physical forms. For example, compound 10 can be in solution, suspension, or in solid form. In certain embodiments, compound 10 is in solid form. When compound 10 is in solid form, said compound may be amorphous, crystalline, or a mixture thereof. Exemplary solid forms are described in more detail below.

In some embodiments, the present invention provides compound 10 substantially free of impurities. As used herein, the term "substantially free of impurities" means that the compound contains no significant amount of extraneous matter. Such extraneous matter may include excess cinnamic acid, excess compound A, residual solvents, or any other impurities that may result from the preparation of, and/or isolation of, compound 10. In certain embodiments, at least In certain embodiments, compound 10 is a crystalline solid. In other embodiments, compound 10 is a crystalline solid substantially free of amorphous compound 10. As used herein, the term "substantially free of amorphous compound 10" means that the compound contains no significant amount of amorphous compound 10. In certain embodiments, at least about 95% by weight of crystalline compound 10 is present. In still other embodiments of the invention, at least about 99% by weight of crystalline compound 10 is present.

In some embodiments, compound 10 is amorphous. In some embodiments, compound 10 is amorphous, and is substantially free of crystalline compound 10.

Form A of Compound 10

In some embodiments, Form A of compound 10 has at least 1, 2, 3, 4 or 5 spectral peak(s) selected from the peaks listed in Table 10 below.

TABLE 10

XRPD Peak Positions for Form A of Compound 10

| Position [°2θ][1] | Intensity [%] |
|---|---|
| 4.8 | 33.13 |
| 5.7 | 3.96 |
| 6.7 | 4.03 |
| 7.9 | 9 |
| 9.6 | 78.7 |
| 11.5 | 29.66 |
| 12.6 | 11.29 |
| 12.8 | 27.51 |
| 13.5 | 18.67 |
| 13.6 | 28.47 |
| 14.3 | 46.33 |
| 15.1 | 87.8 |
| 15.7 | 100 |
| 15.9 | 16.89 |
| 17.0 | 8.46 |
| 17.5 | 9.36 |
| 18.3 | 12.81 |
| 19.2 | 18.88 |
| 20.3 | 18.64 |
| 20.7 | 9.31 |

TABLE 10-continued

XRPD Peak Positions for Form A of Compound 10

| Position [°2θ][1] | Intensity [%] |
|---|---|
| 21.2 | 64.74 |
| 21.6 | 8.8 |
| 22.5 | 15.25 |
| 23.0 | 9.48 |
| 23.9 | 6.18 |
| 24.9 | 15.92 |
| 25.4 | 24.53 |
| 25.8 | 51.55 |
| 26.1 | 57.05 |
| 26.6 | 5.58 |
| 27.1 | 22.2 |
| 27.3 | 36.9 |
| 27.7 | 4.35 |
| 28.2 | 4.7 |
| 28.9 | 12.06 |
| 29.5 | 6.85 |
| 30.5 | 3.04 |
| 30.8 | 5.92 |
| 32.6 | 3.4 |
| 32.8 | 2.74 |
| 34.0 | 1.03 |
| 34.4 | 6.57 |
| 34.9 | 3.11 |
| 36.4 | 5.37 |

[1] In this and all subsequent tables, the position 2θ is within ±0.2.

In some embodiments, Form A of compound 10 is characterized in that it has one or more peaks in its X-ray powder diffraction pattern selected from those at about 9.6, about 15.1 and about 15.7 degrees 2-theta. In some embodiments, Form A of compound 10 is characterized in that it has two or more peaks in its X-ray powder diffraction pattern selected from those at about 9.6, about 15.1 and about 15.7 degrees 2-theta. In some embodiments, Form A of compound 10 is characterized in that it has all three peaks in its X-ray powder diffraction pattern selected from those at about 9.6, about 15.1 and about 15.7 degrees 2-theta.

Figure 19:
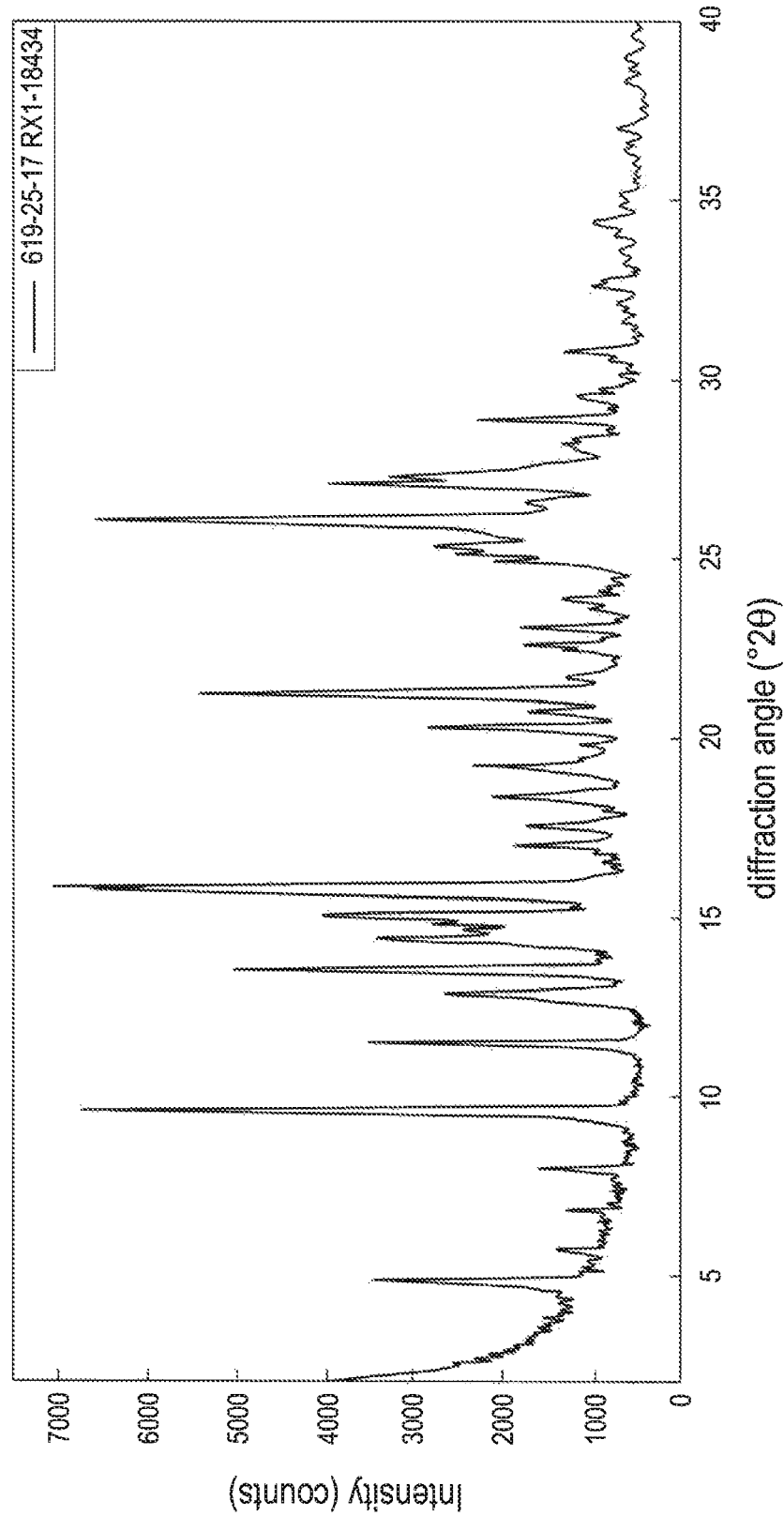
FIG. 19 depicts the XRPD pattern of Compound 10, Form A.

In certain embodiments, the X-ray powder diffraction pattern is substantially similar to the XRPD provided in FIG. 19.

Methods for preparing Form A of compound 10 are described infra.

In some embodiments, the present invention provides compound 10:

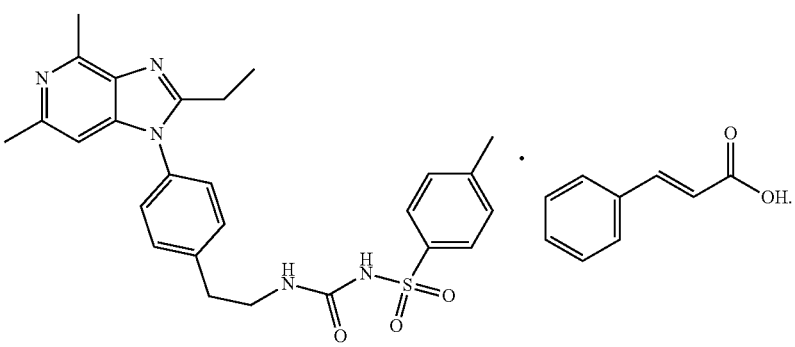

10

In some embodiments, the present invention provides compound 10, wherein said compound is crystalline.

In some embodiments, the present invention provides compound 10, wherein said compound is a crystalline solid substantially free of amorphous compound 10.

In some embodiments, the present invention provides compound 10, wherein said compound is substantially free of impurities.

In some embodiments, the present invention provides compound 10, wherein said compound has one or more peaks in its XRPD selected from those at about 9.6, about 15.1 and about 15.7 degrees 2-theta. In some such embodiments, the present invention provides compound 10, wherein said compound has at least two peaks in its XRPD selected from those at about 9.6, about 15.1 and about 15.7 degrees 2-theta. In some such embodiments, the present invention provides compound 10, wherein said compound is of Form A.

In some embodiments, the present invention provides compound 10, wherein said compound has an XRPD substantially similar to that depicted in FIG. 19.

In some embodiments, the present invention provides a composition comprising compound 10 and a pharmaceutically acceptable carrier or excipient.

In some embodiments, the present invention provides a method of inhibiting, preventing and/or reducing severity of a proliferative disorder associated with prostaglandin EP4 receptor activity in a patient comprising administering to said patient compound 10 or composition thereof.

In some embodiments, the present invention provides a method of treating various conditions in a patient in which prostaglandin EP4 receptor activity is implicated in the pathogenesis, comprising administering to said patient compound 10 or composition thereof. In some such embodiments, the various conditions in a patient in which prostaglandin EP4 receptor activity is implicated in the pathogenesis may include cancer, such as, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

Compound 11 (Resorcinol Co-Crystals of Compound A)

According to one embodiment, the present invention provides a resorcinol co-crystal of compound A, represented by compound 11:

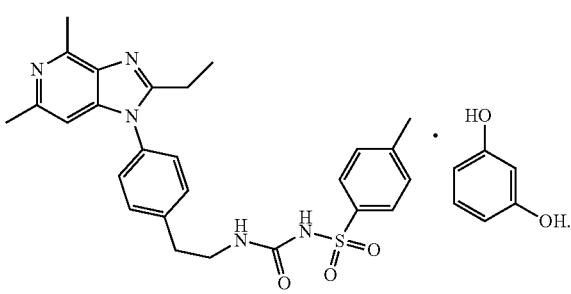

11

It will be appreciated by one of ordinary skill in the art that the resorcinol and compound A are bonded via van der waals and pi-pi interactions, among others, to form compound 11. It is contemplated that compound 11 can exist in a variety of physical forms. For example, compound 11 can be in solution, suspension, or in solid form. In certain embodiments, compound 11 is in solid form. When compound 11 is in solid form, said compound may be amorphous, crystalline, or a mixture thereof. Exemplary solid forms are described in more detail below.

In some embodiments, the present invention provides compound 11 substantially free of impurities. As used herein, the term "substantially free of impurities" means that the compound contains no significant amount of extraneous matter. Such extraneous matter may include excess resorcinol, excess compound A, residual solvents, or any other impurities that may result from the preparation of, and/or isolation of, compound 11. In certain embodiments, at least about 95% by weight of compound 11 is present. In still other embodiments of the invention, at least about 99% by weight of compound 11 is present.

According to one embodiment, compound 11 is present in an amount of at least about 97, 97.5, 98.0, 98.5, 99, 99.5, 99.8 weight percent where the percentages are based on the total weight of the composition. According to another embodiment, compound 11 contains no more than about 3.0 area percent HPLC of total organic impurities and, in certain embodiments, no more than about 1.5 area percent HPLC total organic impurities relative to the total area of the HPLC chromatogram. In other embodiments, compound 11 contains no more than about 1.0% area percent HPLC of any single impurity; no more than about 0.6 area percent HPLC of any single impurity, and, in certain embodiments, no more than about 0.5 area percent HPLC of any single impurity, relative to the total area of the HPLC chromatogram.

The structure depicted for compound 11 is also meant to include all tautomeric forms of compound 11. Additionally, structures depicted here are also meant to include compounds that differ only in the presence of one or more isotopically enriched atoms. For example, compounds having the present structure except for the replacement of hydrogen by deuterium or tritium, or the replacement of a carbon by a 13C- or 1+C-enriched carbon are within the scope of this invention.

It has been found that compound 11 can exist in a variety of solid forms. Exemplary such forms include polymorphs such as those described herein.

In certain embodiments, compound 11 is a crystalline solid. In other embodiments, compound 11 is a crystalline solid substantially free of amorphous compound 11. As used herein, the term "substantially free of amorphous compound 11" means that the compound contains no significant amount of amorphous compound 11. In certain embodiments, at least about 95% by weight of crystalline compound 11 is present. In still other embodiments of the invention, at least about 99% by weight of crystalline compound 11 is present.

In some embodiments, compound 11 is amorphous. In some embodiments, compound 12 is amorphous, and is substantially free of crystalline compound 11.

Form A of Compound 11

In some embodiments, Form A of compound 11 has at least 1, 2, 3, 4 or 5 spectral peak(s) selected from the peaks listed in Table 11 below.

TABLE 11

XRPD Peak Positions for Form A of Compound 11

| Position [°2θ][1] | Intensity [%] |
|---|---|
| 8.9 | 32.03 |
| 10.8 | 52.36 |
| 12.5 | 7.09 |
| 13.6 | 50.66 |
| 13.9 | 31.47 |

TABLE 11-continued

XRPD Peak Positions for Form A of Compound 11

| Position [°2θ][1] | Intensity [%] |
|---|---|
| 14.4 | 24.94 |
| 14.9 | 9.24 |
| 15.5 | 4.1 |
| 16.1 | 49.99 |
| 16.5 | 14.44 |
| 17.7 | 16.65 |
| 18.5 | 27.49 |
| 19.4 | 20.16 |
| 19.7 | 100 |
| 20.2 | 20.65 |
| 20.4 | 12.01 |
| 20.8 | 31.74 |
| 22.3 | 32.84 |
| 23.1 | 44.36 |
| 23.6 | 27.21 |
| 24.1 | 14.46 |
| 24.9 | 14.43 |
| 25.2 | 19.18 |
| 25.6 | 2.42 |
| 26.6 | 16.02 |
| 27.1 | 5.85 |
| 30.2 | 10.54 |
| 31.9 | 6.66 |

[1]In this and all subsequent tables, the position 2θ is within ±0.2.

In some embodiments, Form A of compound 11 is characterized in that it has one or more peaks in its X-ray powder diffraction pattern selected from those at about 10.8, about 13.6 and about 19.7 degrees 2-theta. In some embodiments, Form A of compound 11 is characterized in that it has two or more peaks in its X-ray powder diffraction pattern selected from those at about 10.8, about 13.6 and about 19.7 degrees 2-theta. In some embodiments, Form A of compound 11 is characterized in that it has all three peaks in its X-ray powder diffraction pattern selected from those at about 10.8, about 13.6 and about 19.7 degrees 2-theta.

Figure 21:
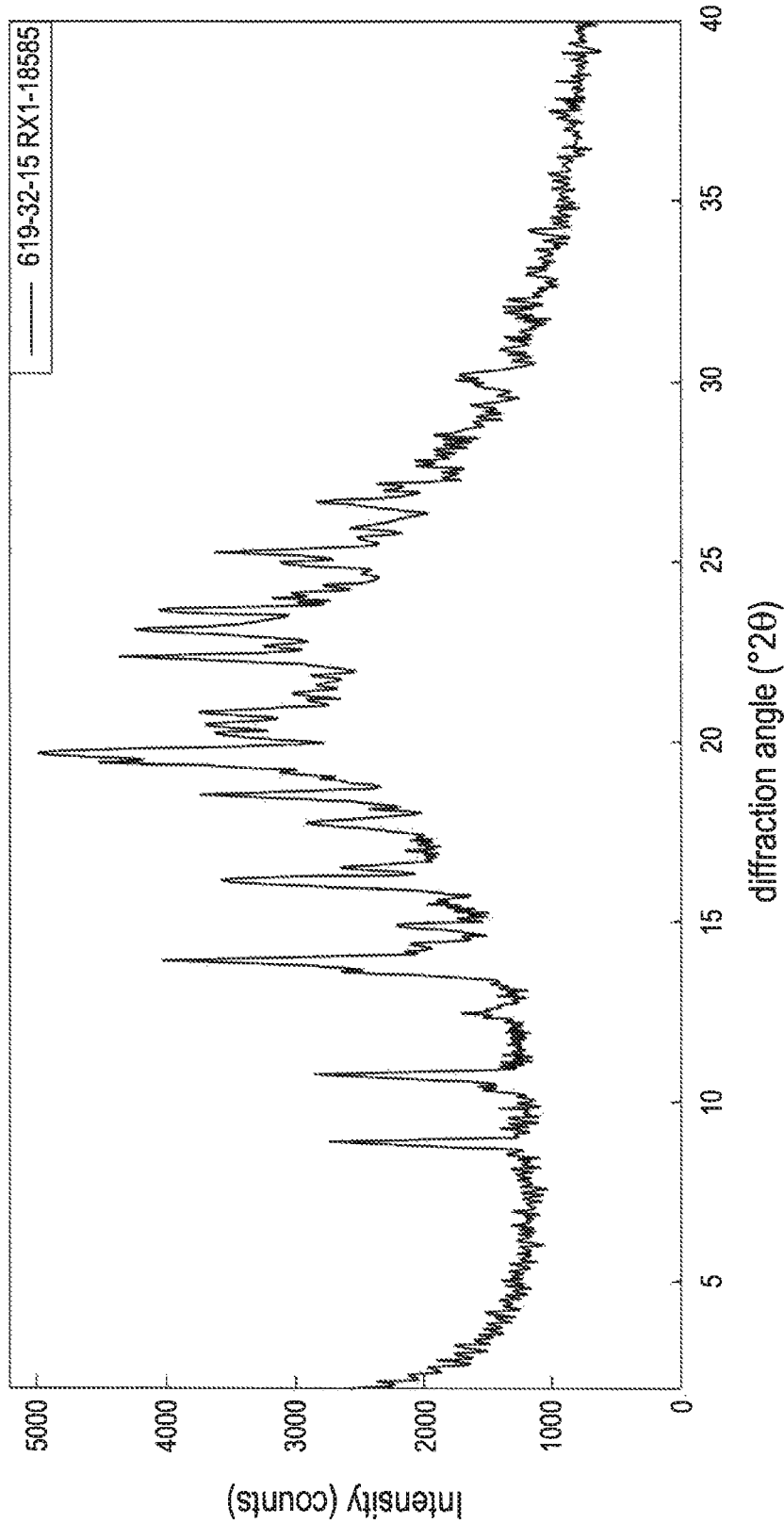
FIG. 21 depicts the XRPD pattern of Compound 11, Form A.

In certain embodiments, the X-ray powder diffraction pattern is substantially similar to the XRPD provided in FIG. 21.

Methods for preparing Form A of compound 11 are described infra.

In some embodiments, the present invention provides compound 11:

11

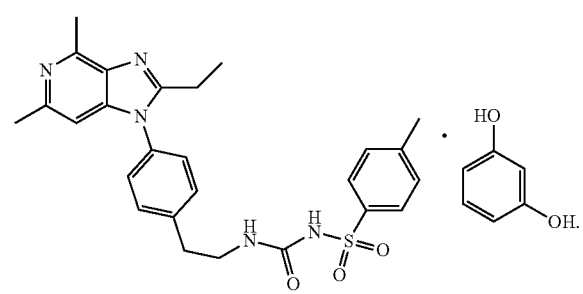

In some embodiments, the present invention provides compound 11, wherein said compound is crystalline.

In some embodiments, the present invention provides compound 11, wherein said compound is a crystalline solid substantially free of amorphous compound 11.

In some embodiments, the present invention provides compound 11, wherein said compound is substantially free of impurities.

In some embodiments, the present invention provides compound 11, wherein said compound has one or more peaks in its XRPD selected from those at about 10.8, about 13.6 and about 19.7 degrees 2-theta. In some such embodiments, the present invention provides compound 11, wherein said compound has at least two peaks in its XRPD selected from those at about 10.8, about 13.6 and about 19.7 degrees 2-theta. In some such embodiments, the present invention provides compound 11, wherein said compound is of Form A.

In some embodiments, the present invention provides compound 11, wherein said compound has an XRPD substantially similar to that depicted in FIG. 21.

In some embodiments, the present invention provides a composition comprising compound 11 and a pharmaceutically acceptable carrier or excipient.

In some embodiments, the present invention provides a method of inhibiting, preventing and/or reducing severity of a proliferative disorder associated with prostaglandin EP4 receptor activity in a patient comprising administering to said patient compound 11 or composition thereof.

In some embodiments, the present invention provides a method of treating various conditions in a patient in which prostaglandin EP4 receptor activity is implicated in the pathogenesis, comprising administering to said patient compound 11 or composition thereof. In some such embodiments, the various conditions in a patient in which prostaglandin EP4 receptor activity is implicated in the pathogenesis may include cancer, such as, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

In some embodiments, the present invention provides a compound selected from: compound 1, Form A; compound 2, Form A; compound 3, Form A; compound 4, Form A; compound 5, Form A; compound 6, Form A; compound 7, Form A; compound 8, Form A; compound 9, Form A; compound 10, Form A; and compound 11, Form A. In some such embodiments, the present invention provides a composition comprising one of the above compound forms and a pharmaceutically acceptable carrier or excipient. In some such embodiments, the present invention provides a method of inhibiting, preventing and/or reducing severity of a proliferative disorder associated with prostaglandin EP4 receptor activity in a patient comprising administering to said patient one of the above compound forms or composition thereof. In some embodiments, the present invention provides a method of treating various conditions in a patient in which prostaglandin EP4 receptor activity is implicated in the pathogenesis, comprising administering to said patient one of the above compound forms or composition thereof. In some such embodiments, the various conditions in a patient in which prostaglandin EP4 receptor activity is implicated in the pathogenesis may include cancer, such as, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

General Methods of Providing a Salt or Co-Crystal Compound

Compound A is prepared according to the methods described in detail in the '407 patent, the entirety of which is hereby incorporated herein by reference. Salt or co-crystal compounds of general formula X, which formula encompasses, inter alia, compounds 1 through 11, and/or particular forms thereof, are prepared from compound A, according to the general Scheme below.

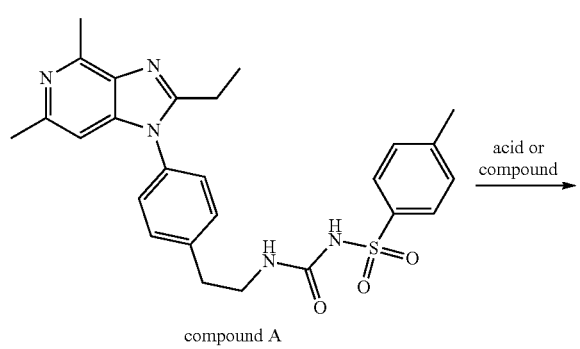

compound A

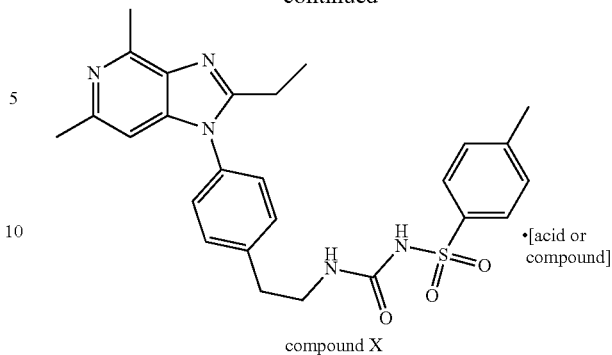

compound X

For instance, each of compounds 1 through 11, and forms thereof, are prepared from compound A by combining compound A with an appropriate acid or compound to form a salt or co-crystal. Thus, another aspect of the present invention provides a method for preparing compounds 1 through 11, and forms thereof.

As described generally above, in some embodiments, the present invention provides a method for preparing a salt or co-crystal compound of the general formula X:

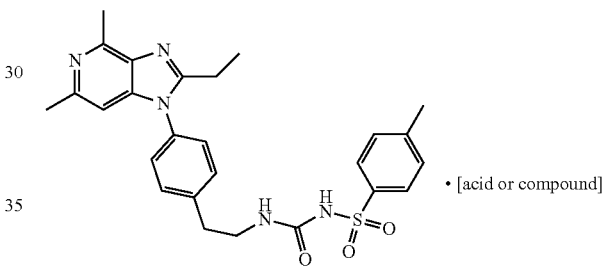

salt or co-crystal compound X comprising steps of:
combining compound A:

compound A

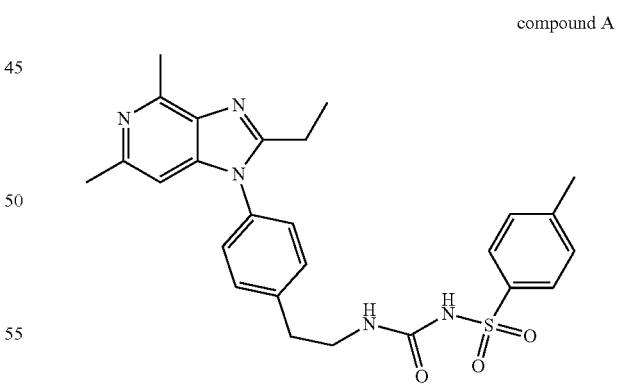

with a suitable acid or compound and optionally a suitable solvent under conditions suitable for forming a salt or co-crystal compound of general formula X.

In some embodiments, a suitable acid or compound is 1,2-ethanedisulfonic acid. In some embodiments, the present invention provides a method of making an edisylate salt of compound A. In certain embodiments, the edisylate salt of compound A is compound 1. In certain embodiments, the edisylate salt of compound A is Form A of compound 1.

In some embodiments, a suitable acid or compound is ethanesulfonic acid. In some embodiments, the present invention provides a method of making a esylate salt of compound A. In certain embodiments, the esylate salt of compound A is compound 2. In certain embodiments, the esylate salt of compound A is Form A of compound 2.

In some embodiments, a suitable acid or compound is gentisic acid. In some embodiments, the present invention provides a method of making a gentisate salt of compound A. In certain embodiments, the gentisate salt of compound A is compound 3. In certain embodiments, the gentisate salt of compound A is Form A of compound 3.

In some embodiments, a suitable acid or compound is hydrochloric acid. In some embodiments, the present invention provides a method of making a hydrochloride salt of compound A. In certain embodiments, the hydrochloric salt of compound A is compound 4. In certain embodiments, the hydrochloride salt of compound A is Form A of compound 4.

In some embodiments, a suitable acid or compound is 1-hydroxy-2-napthoic acid. In some embodiments, the present invention provides a method of making a xinafoate salt of compound A. In certain embodiments, the xinafoate salt of compound A is compound 5. In certain embodiments, the xinafoate salt of compound A is Form A of compound 5.

In some embodiments, a suitable acid or compound is isethionic acid. In some embodiments, the present invention provides a method of making an isethionate salt of compound A. In certain embodiments, the isethionate salt of compound A is compound 6. In certain embodiments, the isethionate salt of compound A is Form A of compound 6.

In some embodiments, a suitable acid or compound is methanesulfonic acid. In some embodiments, the present invention provides a method of making an mesylate salt of compound A. In certain embodiments, the mesylate salt of compound A is compound 7. In certain embodiments, the mesylate salt of compound A is Form A of compound 7.

In some embodiments, a suitable acid or compound is napthalene-1,5-disulfonic acid. In some embodiments, the present invention provides a method of making a napadisylate salt of compound A. In certain embodiments, the phosphate salt of compound A is compound 8. In certain embodiments, the phosphate salt of compound A is Form A of compound 8.

In some embodiments, a suitable acid or compound is oxalic acid. In some embodiments, the present invention provides a method of making an oxalate salt of compound A. In certain embodiments, the oxalate salt of compound A is compound 9. In certain embodiments, the oxalate salt of compound A is Form A of compound 9.

In some embodiments, a suitable acid or compound is cinnamic acid. In some embodiments, the present invention provides a method of making a cinnamic acid co-crystal of compound A. In certain embodiments, the cinnamic acid co-crystal of compound A is compound 10. In certain embodiments, the cinnamic acid co-crystal of compound A is Form A of compound 10.

In some embodiments, a suitable acid or compound is resorcinol. In some embodiments, the present invention provides a method of making a resorcinol co-crystal of compound A. In certain embodiments, the resorcinol co-crystal of compound A is compound 11. In certain embodiments, the resorcinol co-crystal of compound A is Form A of compound 11.

A suitable solvent may be any solvent system (e.g., one solvent or a mixture of solvents) in which compound A and/or an acid are soluble, or are at least partially soluble.

Examples of suitable solvents useful in the present invention include, but are not limited to protic solvents, aprotic solvents, polar aprotic solvent, or mixtures thereof. In certain embodiments, suitable solvents include an ether, an ester, an alcohol, a ketone, or a mixture thereof. In some embodiments, the solvent is one or more organic alcohols. In some embodiments, the solvent is chlorinated. In some embodiments, the solvent is an aromatic solvent.

In certain embodiments, a suitable solvent is methanol, ethanol, isopropanol, or acetone wherein said solvent is anhydrous or in combination with water or heptane. In some embodiments, suitable solvents include tetrahydrofuran, dimethylformamide, dimethylsulfoxide, glyme, diglyme, methyl t-butyl ether, t-butanol, n-butanol, and acetonitrile. In some embodiments, a suitable solvent is ethanol. In some embodiments, a suitable solvent is anhydrous ethanol. In some embodiments, the suitable solvent is MTBE.

In some embodiments, a suitable solvent is ethyl acetate. In some embodiments, a suitable solvent is a mixture of methanol and methylene chloride. In some embodiments, a suitable solvent is a mixture of acetonitrile and water. In certain embodiments, a suitable solvent is methyl acetate, isopropyl acetate, acetone, or tetrahydrofuran. In certain embodiments, a suitable solvent is diethylether. In certain embodiments, a suitable solvent is water. In certain embodiments, a suitable solvent is methyl ethyl ketone. In certain embodiments, a suitable solvent is toluene.

In some embodiments, the present invention provides a method for preparing a salt or co-crystal compound of the general formula X, comprising one or more steps of removing a solvent and adding a solvent. In some embodiments, an added solvent is the same as the solvent removed. In some embodiments, an added solvent is different from the solvent removed. Means of solvent removal are known in the synthetic and chemical arts and include, but are not limited to, any of those described herein and in the Exemplification.

In some embodiments, a method for preparing a salt or co-crystal compound of the general formula X comprises one or more steps of heating or cooling a preparation.

In some embodiments, a method for preparing a salt or co-crystal compound of the general formula X comprises one or more steps of agitating or stirring a preparation.

In some embodiments, a method for preparing a salt or co-crystal compound of the general formula X comprises a step of adding a suitable acid to a solution or slurry of compound A.

In some embodiments, a method for preparing a salt or co-crystal compound of the general formula X comprises a step of heating.

In certain embodiments, a salt or co-crystal compound of formula X precipitates from the mixture. In another embodiment, a salt or co-crystal compound of formula X crystallizes from the mixture. In other embodiments, a salt or co-crystal compound of formula X crystallizes from solution following seeding of the solution (i.e., adding crystals of a salt or co-crystal compound of formula X to the solution).

A salt or co-crystal compound of formula X can precipitate out of the reaction mixture, or be generated by removal of part or all of the solvent through methods such as evaporation, distillation, filtration (ex. nanofiltration, ultrafiltration), reverse osmosis, absorption and reaction, by adding an anti-solvent such as heptane, by cooling or by different combinations of these methods.

As described generally above, a salt or co-crystal compound of formula X is optionally isolated. It will be appreciated that a salt or co-crystal compound of formula X may be isolated by any suitable physical means known to one of ordinary skill in the art. In certain embodiments, precipitated solid salt or co-crystal compound of formula X is separated from the supernatant by filtration. In other embodiments, precipitated solid salt or co-crystal compound of formula X is separated from the supernatant by decanting the supernatant.

In certain embodiments, a salt or co-crystal compound of formula X is separated from the supernatant by filtration.

In certain embodiments, an isolated salt or co-crystal compound of formula X is dried in air. In other embodiments, isolated salt or co-crystal compound of formula X is dried under reduced pressure, optionally at elevated temperature.

Combinations with Other Therapeutic Agents

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

One or more other therapeutic agent may be administered separately from a compound or composition of the invention, as part of a multiple dosage regimen. Alternatively, one or more other therapeutic agents may be part of a single dosage form, mixed together with a compound of this invention in a single composition. If administered as a multiple dosage regime, one or more other therapeutic agent and a compound or composition of the invention may be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent and a compound or composition of the invention are administered as a multiple dosage regimen within greater than 24 hours apart.

As used herein, the term "combination," "combined," and related terms refers to the simultaneous or sequential administration of therapeutic agents in accordance with this invention. For example, a compound of the present invention may be administered with one or more other therapeutic agent simultaneously or sequentially in separate unit dosage forms or together in a single unit dosage form. Accordingly, the present invention provides a single unit dosage form comprising a compound of the current invention, one or more other therapeutic agent, and a pharmaceutically acceptable carrier, adjuvant, or vehicle.

The amount of a compound of the invention and one or more other therapeutic agent (in those compositions which comprise an additional therapeutic agent as described above) that may be combined with the carrier materials to produce a single dosage form will vary depending upon the host treated and the particular mode of administration. Preferably, a composition of the invention should be formulated so that a dosage of between 0.01-100 mg/kg body weight/day of a compound of the invention can be administered.

In those compositions which comprise one or more other therapeutic agent, the one or more other therapeutic agent and a compound of the invention may act synergistically. Therefore, the amount of the one or more other therapeutic agent in such compositions may be less than that required in a monotherapy utilizing only that therapeutic agent. In such compositions a dosage of between 0.01-1,000 µg/kg body weight/day of the one or more other therapeutic agent can be administered.

The amount of one or more other therapeutic agent present in the compositions of this invention may be no more than the amount that would normally be administered in a composition comprising that therapeutic agent as the only active agent. Preferably the amount of one or more other therapeutic agent in the presently disclosed compositions will range from about 50% to 100% of the amount normally present in a composition comprising that agent as the only therapeutically active agent. In some embodiments, one or more other therapeutic agent is administered at a dosage of about 50%, about 55%, about 60%, about 65%, about 70%, about 75%, about 80%, about 85%, about 90%, or about 95% of the amount normally administered for that agent. As used herein, the phrase "normally administered" means the amount an FDA approved therapeutic agent is approved for dosing per the FDA label insert.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

Exemplary Other Therapeutic Agents

In some embodiments, one or more other therapeutic agent is a Poly ADP ribose polymerase (PARP) inhibitor. In some embodiments, a PARP inhibitor is selected from olaparib (Lynparza®, AstraZeneca); rucaparib (Rubraca®, Clovis Oncology); niraparib (Zejula®, Tesaro); talazoparib (MDV3800/BMN 673/LT00673, Medivation/Pfizer/Biomarin); veliparib (ABT-888, Abb Vie); and BGB-290 (BeiGene, Inc.).

In some embodiments, one or more other therapeutic agent is a histone deacetylase (HDAC) inhibitor. In some embodiments, an HDAC inhibitor is selected from vorinostat (Zolinza®, Merck); romidepsin (Istodax®, Celgene); panobinostat (Farydak®, Novartis); belinostat (Beleodaq®, Spectrum Pharmaceuticals); entinostat (SNDX-275, Syndax Pharmaceuticals) (NCT00866333); and chidamide (Epidaza®, HBI-8000, Chipscreen Biosciences, China).

In some embodiments, one or more other therapeutic agent is a CDK inhibitor, such as a CDK4/CDK6 inhibitor. In some embodiments, a CDK 4/6 inhibitor is selected from palbociclib (Ibrance®, Pfizer); ribociclib (Kisqali®, Novartis); abemaciclib (Ly2835219, Eli Lilly); and trilaciclib (G1T28, G1 Therapeutics).

In some embodiments, one or more other therapeutic agent is a phosphatidylinositol 3 kinase (PI3K) inhibitor. In some embodiments, a PI3K inhibitor is selected from idelalisib (Zydelig®, Gilead), alpelisib (BYL719, Novartis), taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

In some embodiments, one or more other therapeutic agent is a platinum-based therapeutic, also referred to as platins. Platins cause cross-linking of DNA, such that they inhibit DNA repair and/or DNA synthesis, mostly in rapidly reproducing cells, such as cancer cells. In some embodiments, a platinum-based therapeutic is selected from cisplatin (Platinol®, Bristol-Myers Squibb); carboplatin (Paraplatin®, Bristol-Myers Squibb; also, Teva; Pfizer); oxaliplatin (Eloxitin® Sanofi-Aventis); nedaplatin (Aqupla®, Shionogi), picoplatin (Poniard Pharmaceuticals); and satraplatin (JM-216, Agennix).

In some embodiments, one or more other therapeutic agent is a taxane compound, which causes disruption of microtubules, which are essential for cell division. In some embodiments, a taxane compound is selected from paclitaxel (Taxol®, Bristol-Myers Squibb), docetaxel (Taxotere®, Sanofi-Aventis; Docefrez®, Sun Pharmaceutical), albumin-bound paclitaxel (Abraxane®; Abraxis/Celgene), cabazitaxel (Jevtana®, Sanofi-Aventis), and SID530 (SK Chemicals, Co.) (NCT00931008).

In some embodiments, one or more other therapeutic agent is a nucleoside inhibitor, or a therapeutic agent that interferes with normal DNA synthesis, protein synthesis, cell replication, or will otherwise inhibit rapidly proliferating cells.

In some embodiments, a nucleoside inhibitor is selected from trabectedin (guanidine alkylating agent, Yondelis®, Janssen Oncology), mechlorethamine (alkylating agent, Valchlor®, Aktelion Pharmaceuticals); vincristine (Oncovin®, Eli Lilly; Vincasar®, Teva Pharmaceuticals; Marqibo®, Talon Therapeutics); temozolomide (prodrug to alkylating agent 5-(3-methyltriazen-1-yl)-imidazole-4-carboxamide (MTIC) Temodar®, Merck); cytarabine injection (ara-C, antimetabolite cytidine analog, Pfizer); lomustine (alkylating agent, CeeNU®, Bristol-Myers Squibb; Gleostine®, NextSource Biotechnology); azacitidine (pyrimidine nucleoside analog of cytidine, Vidaza®, Celgene); omacetaxine mepesuccinate (cephalotaxine ester) (protein synthesis inhibitor, Synribo®; Teva Pharmaceuticals); asparaginase *Erwinia chrysanthemi* (enzyme for depletion of asparagine, Elspar®, Lundbeck; Erwinaze®, EUSA Pharma); eribulin mesylate (microtubule inhibitor, tubulin-based antimitotic, Halaven®, Eisai); cabazitaxel (microtubule inhibitor, tubulin-based antimitotic, Jevtana®, Sanofi-Aventis); capacetrine (thymidylate synthase inhibitor, Xeloda®, Genentech); bendamustine (bifunctional mechlorethamine derivative, believed to form interstrand DNA cross-links, Treanda®, Cephalon/Teva); ixabepilone (semi-synthetic analog of epothilone B, microtubule inhibitor, tubulin-based antimitotic, Ixempra®, Bristol-Myers Squibb); nelarabine (prodrug of deoxyguanosine analog, nucleoside metabolic inhibitor, Arranon®, Novartis); clorafabine (prodrug of ribonucleotide reductase inhibitor, competitive inhibitor of deoxycytidine, Clolar®, Sanofi-Aventis); and trifluridine and tipiracil (thymidine-based nucleoside analog and thymidine phosphorylase inhibitor, Lonsurf®, Taiho Oncology).

In some embodiments, one or more other therapeutic agent is a kinase inhibitor or VEGF-R antagonist. Approved VEGF inhibitors and kinase inhibitors useful in the present invention include: bevacizumab (Avastin®, Genentech/Roche) an anti-VEGF monoclonal antibody; ramucirumab (Cyramza®, Eli Lilly), an anti-VEGFR-2 antibody and ziv-aflibercept, also known as VEGF Trap (Zaltrap®; Regeneron/Sanofi). VEGFR inhibitors, such as regorafenib (Stivarga®, Bayer); vandetanib (Caprelsa®, AstraZeneca); axitinib (Inlyta®, Pfizer); and lenvatinib (Lenvima®, Eisai); Raf inhibitors, such as sorafenib (Nexavar®, Bayer AG and Onyx); dabrafenib (Tafinlar®, Novartis); and vemurafenib (Zelboraf®, Genentech/Roche); MEK inhibitors, such as cobimetanib (Cotellic®, Exelexis/Genentech/Roche); trametinib (Mekinist®, Novartis); Bcr-Abl tyrosine kinase inhibitors, such as imatinib (Gleevec®, Novartis); nilotinib (Tasigna®, Novartis); dasatinib (Sprycel®, BristolMyersSquibb); bosutinib (Bosulif®, Pfizer); and ponatinib (Inclusig®, Ariad Pharmaceuticals); Her2 and EGFR inhibitors, such as gefitinib (Iressa®, AstraZeneca); erlotinib (Tarceeva®, Genentech/Roche/Astellas); lapatinib (Tykerb®, Novartis); afatinib (Gilotrif®, Boehringer Ingelheim); osimertinib (targeting activated EGFR, Tagrisso®, AstraZeneca); and brigatinib (Alunbrig®, Ariad Pharmaceuticals); c-Met and VEGFR2 inhibitors, such as cabozanitib (Cometriq®, Exelexis); and multikinase inhibitors, such as sunitinib (Sutent®, Pfizer); pazopanib (Votrient®, Novartis); ALK inhibitors, such as crizotinib (Xalkori®, Pfizer); ceritinib (Zykadia®, Novartis); and alectinib (Alecenza®, Genentech/Roche); Bruton's tyrosine kinase inhibitors, such as ibrutinib (Imbruvica®, Pharmacyclics/Janssen); and Flt3 receptor inhibitors, such as midostaurin (Rydapt®, Novartis).

Other kinase inhibitors and VEGF-R antagonists that are in development and may be used in the present invention include tivozanib (Aveo Pharmaeuticals); vatalanib (Bayer/Novartis); lucitanib (Clovis Oncology); dovitinib (TKI258, Novartis); Chiauanib (Chipscreen Biosciences); CEP-11981 (Cephalon); linifanib (Abbott Laboratories); neratinib (HKI-272, Puma Biotechnology); radotinib (Supect®, IY5511, Il-Yang Pharmaceuticals, S. Korea); ruxolitinib (Jakafi®, Incyte Corporation); PTC299 (PTC Therapeutics); CP-547,632 (Pfizer); foretinib (Exelexis, GlaxoSmithKline); quizartinib (Daiichi Sankyo) and motesanib (Amgen/Takeda).

In some embodiments, one or more other therapeutic agent is an mTOR inhibitor, which inhibits cell proliferation, angiogenesis and glucose uptake. In some embodiments, an mTOR inhibitor is everolimus (Afinitor®, Novartis); temsirolimus (Torisel®, Pfizer); and sirolimus (Rapamune®, Pfizer).

In some embodiments, one or more other therapeutic agent is a proteasome inhibitor. Approved proteasome inhibitors useful in the present invention include bortezomib (Velcade®, Takeda); carfilzomib (Kyprolis®, Amgen); and ixazomib (Ninlaro®, Takeda).

In some embodiments, one or more other therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (Lartruvo®; Eli Lilly). Approved EGFR antagonists which may be used in the present invention include cetuximab (Erbitux®, Eli Lilly); necitumumab (Portrazza®, Eli Lilly), panitumumab (Vectibix®, Amgen); and osimertinib (targeting activated EGFR, Tagrisso®, AstraZeneca).

In some embodiments, one or more other therapeutic agent is an aromatase inhibitor. In some embodiments, an aromatase inhibitor is selected from exemestane (Aromasin®, Pfizer); anastazole (Arimidex®, AstraZeneca) and letrozole (Femara®, Novartis).

In some embodiments, one or more other therapeutic agent is an antagonist of the hedgehog pathway. Approved hedgehog pathway inhibitors which may be used in the present invention include sonidegib (Odomzo®, Sun Pharmaceuticals); and vismodegib (Erivedge®, Genentech), both for treatment of basal cell carcinoma.

In some embodiments, one or more other therapeutic agent is a folic acid inhibitor. Approved folic acid inhibitors useful in the present invention include pemetrexed (Alimta®, Eli Lilly).

In some embodiments, one or more other therapeutic agent is a CC chemokine receptor 4 (CCR4) inhibitor. CCR4 inhibitors being studied that may be useful in the present invention include mogamulizumab (Poteligeo®, Kyowa Hakko Kirin, Japan).

In some embodiments, one or more other therapeutic agent is an isocitrate dehydrogenase (IDH) inhibitor. IDH inhibitors being studied which may be used in the present invention include AG120 (Celgene; NCT02677922); AG221 (Celgene, NCT02677922; NCT02577406); BAY1436032 (Bayer, NCT02746081); IDH305 (Novartis, NCT02987010).

In some embodiments, one or more other therapeutic agent is an arginase inhibitor. Arginase inhibitors being studied which may be used in the present invention include AEB1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, one or more other therapeutic agent is a glutaminase inhibitor. Glutaminase inhibitors being studied which may be used in the present invention include CB-839 (Calithera Biosciences).

In some embodiments, one or more other therapeutic agent is an antibody that binds to tumor antigens, that is, proteins expressed on the cell surface of tumor cells. Approved antibodies that bind to tumor antigens which may be used in the present invention include rituximab (Rituxan®, Genentech/BiogenIdec); ofatumumab (anti-CD20, Arzerra®, GlaxoSmithKline); obinutuzumab (anti-CD20, Gazyva®, Genentech), ibritumomab (anti-CD20 and Yttrium-90, Zevalin®, Spectrum Pharmaceuticals); daratumumab (anti-CD38, Darzalex®, Janssen Biotech); dinutuximab (anti-glycolipid GD2, Unituxin®, United Therapeutics); trastuzumab (anti-HER2, Herceptin®, Genentech); ado-trastuzumab emtansine (anti-HER2, fused to emtansine, Kadcyla®, Genentech); and pertuzumab (anti-HER2, Perjeta®, Genentech); and brentuximab vedotin (anti-CD30-drug conjugate, Adcetris®, Seattle Genetics).

In some embodiments, one or more other therapeutic agent is a topoisomerase inhibitor. Approved topoisomerase inhibitors useful in the present invention include irinotecan (Onivyde®, Merrimack Pharmaceuticals); topotecan (Hycamtin®, GlaxoSmithKline). Topoisomerase inhibitors being studied which may be used in the present invention include pixantrone (Pixuvri®, CTI Biopharma).

In some embodiments, one or more other therapeutic agent is an inhibitor of anti-apoptotic proteins, such as BCL-2. Approved anti-apoptotics which may be used in the present invention include venetoclax (Venclexta®, Abb Vie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

In some embodiments, one or more other therapeutic agent is an androgen receptor inhibitor. Approved androgen receptor inhibitors useful in the present invention include enzalutamide (Xtandi®, Astellas/Medivation); approved inhibitors of androgen synthesis include abiraterone (Zytiga®, Centocor/Ortho); approved antagonist of gonadotropin-releasing hormone (GnRH) receptor (degaralix, Firmagon®, Ferring Pharmaceuticals).

In some embodiments, one or more other therapeutic agent is a selective estrogen receptor modulator (SERM), which interferes with the synthesis or activity of estrogens. Approved SERMs useful in the present invention include raloxifene (Evista®, Eli Lilly).

In some embodiments, one or more other therapeutic agent is an inhibitor of bone resorption. An approved therapeutic which inhibits bone resorption is Denosumab (Xgeva®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (Zometa®, Novartis).

In some embodiments, one or more other therapeutic agent is an inhibitor of interaction between the two primary p53 suppressor proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, one or more other therapeutic agent is an inhibitor of transforming growth factor-beta (TGF-beta or TGFβ). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA-formerly MSB0011459X), which is a bispecific, anti-PD-L1/TGFβ trap compound (NCT02699515); and (NCT02517398). M7824 is comprised of a fully human IgG1 antibody against PD-L1 fused to the extracellular domain of human TGF-beta receptor II, which functions as a TGFβ "trap."

In some embodiments, one or more other therapeutic agent is selected from glembatumumab vedotin-monomethyl auristatin E (MMAE) (Celldex), an anti-glycoprotein NMB (gpNMB) antibody (CR011) linked to the cytotoxic MMAE. gpNMB is a protein overexpressed by multiple tumor types associated with cancer cells' ability to metastasize.

In some embodiments, one or more other therapeutic agent is an antiproliferative compound. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (TemodalR); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZd6244 from AstraZeneca, PD181461 from Pfizer and leucovorin.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™. Letrozole is marketed under the trade names Femara™ or Femar™. Aminoglutethimide is marketed under the trade name Orimeten™ A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™ Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; *vinca* alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™ Docetaxel is marketed under the trade name Taxotere™. Vinblastine sulfate is marketed under the trade name Vinblastin R.P™. Vincristine sulfate is marketed under the trade name Farmistin™

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™ Gemcitabine is marketed under the trade name Gemzar™

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; Ilmofosine; RO 318220 and RO 320432; GO 6976; Isis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR1 ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PIβ KB, PIβK-C2α, PIβK-C2β, PIβK-C2γ, Vps34, p110-α, p110-β, p110-γ, p110-γ, p85-α, p85-β, p55-γ, p150, p101, and p87. Examples of PIβK inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PIβK inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α-γ- or δ-tocopherol or α-γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™ The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (RituxanR), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl){2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4th Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl) phthalazine or a pharmaceutically acceptable salt thereof, 1-(4-chloroanilino)-4-(4-pyridylmethyl) phthalazine succinate; Angiostatin™; Endostatin™; anthranilic acid amides; ZD4190; Zd6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The structure of the active compounds identified by code numbers, generic or trade names may be taken from the actual edition of the standard compendium "The Merck Index" or from databases, e.g. Patents International (e.g. IMS World Publications).

Exemplary Immuno-Oncology agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTBR, LIGHT, DcR3, HVEM, VEGI/TLIA, TRAMP/DR3, EDAR, EDAI, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO2010/077634), durvalumab (MEDI4736), BMS-936559 (WO2007/005874), and MSB0010718C (WO2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO10/19570, WO14/08218), or IMP-731 or IMP-321 (WO08/132601, WO009/44273).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO006/105021, WO009/009116), or MK-4166 (WO11/028683).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS: F001287 (Bristol-Myers Squibb); Phy906/KD108 (Phytoceutica); an enzyme that breaks down kynurenine (Kynase, Kyn Therapeutics); and NLG-919 (WO09/73620, WO009/1156652, WO11/56652, WO12/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO06/029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO11/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (OpdivoR, Bristol-Myers Squibb, also known as ONO-4538, MDX1106 and BMS- 936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase-(TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific CD8+ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+ (Th17) and CD8+ (Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that may be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams ET. AL., "Big opportunities for small molecules in immuno-oncology," Cancer Therapy 2015, Vol. 14, pages 603-622, the content of which is incorporated herein by reference in its entirety. In some embodiments, an immuno-oncology agent is selected from the examples described in Table 1 of Jerry L. Adams ET. AL. In some embodiments, an immuno-oncology agent is a small molecule targeting an immuno-oncology target selected from those listed in Table 2 of Jerry L. Adams ET. AL. In some embodiments, an immuno-oncology agent is a small molecule agent selected from those listed in Table 2 of Jerry L. Adams ET. AL.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BiTE®) antibody constructs can mediate bystander tumor cell killing", PLOS ONE 12 (8): e0183390, the content of which is incorporated herein by reference in its entirety. In some embodiments, an immuno-oncology agent is a bispecific T cell engager (BiTE®) antibody construct. In some embodiments, a bispecific T cell engager (BiTER) antibody construct is a CD19/CD3 bispecific antibody construct. In some embodiments, a bispecific T cell engager (BiTE®) antibody construct is an EGFR/CD3 bispecific antibody construct. In some embodiments, a bispecific T cell engager (BiTE®) antibody construct activates T cells. In some embodiments, a bispecific T cell engager (BiTE®) antibody construct activates T cells, which release cytokines inducing upregulation of intercellular adhesion molecule 1 (ICAM-1) and FAS on bystander cells. In some embodiments, a bispecific T cell engager (BiTE®) antibody construct activates T cells which result in induced bystander cell lysis. In some embodiments, the bystander cells are in solid tumors. In some embodiments, the bystander cells being lysed are in proximity to the BiTE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex-vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory CD8$^+$ (αβ) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®). In some embodiments, the checkpoint inhibitor is selected from nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); and atezolizumab (anti-PD-L1 antibody, Tecentriq®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (Keytruda®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that may be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, *Trillium* Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that may be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2 ((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

Uses of Compounds and Pharmaceutically Acceptable Compositions Thereof

In some embodiments, the present invention provides a method for treating a proliferative disorder in a patient comprising administering to the patient an agent that inhibits prostaglandin EP4 receptor (EP4) activity in combination with an additional therapeutic agent, as described herein. In some embodiments, a proliferative disorder is a cancer selected from those as described herein. In some embodiments, a patient is a cancer patient who has been treated, or is being treated or to be treated, by immunotherapy. In some embodiments, a cancer patient is not pregnant or breastfeeding when receiving the instant treatment. In some embodiments, a cancer patient does not conceive children when receiving the instant treatment.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

In some embodiments, the cancer is small cell lung cancer, non-small cell lung cancer, colorectal cancer, breast cancer, gastric cancer, multiple myeloma, acute myeloid leukemia (AML), acute lymphoblastic leukemia (ALL), pancreatic cancer, liver cancer, hepatocellular cancer, neuroblastoma, other solid tumors or other hematological cancers.

In some embodiments, the cancer is non-small cell lung cancer (NSCLC). In some embodiments, the cancer is advanced and/or metastatic NSCLC. In some embodiments, the cancer is ovarian cancer. In some embodiments, the cancer is breast cancer. In some embodiments, the cancer is head and neck cancer. In some embodiments, the cancer is colorectal cancer (CRC). In some embodiments, the cancer is advanced or progressive microsatellite stable (MSS) CRC.

NSCLC patients

In some embodiments, a cancer patient is a NSCLC patient. In some embodiments, a NSCLC patient has been treated by immunotherapy. In some embodiments, a NSCLC patient has been treated by PD-1/L1 immunotherapy. In some embodiments, a NSCLC patient has been treated by PD-1/L1 immunotherapy for a minimum of 12 weeks. In some embodiments, a NSCLC patient has progressed on PD-1/L1 immunotherapy given for a minimum of 12 weeks (aka post-PD-1/L1 NSCLC adenocarcinoma patients).

In some embodiments, a NSCLC patient has pathologically diagnosed adenocarcinoma histology of NSCLC.

In some embodiments, a NSCLC patient is an advanced (stage IIIb) and metastatic (stage IV) patient who has progressed clinically and/or radiographically per RECIST 1.1 (Response Evaluation Criteria in Solid Tumors).

In some embodiments, a NSCLC patient is at least 18 years old.

In some embodiments, a NSCLC patient has known PD-L1 positive status (>1%). In some embodiments, a NSCLC patient has a measurable disease as per RECIST 1.1. In some embodiments, a NSCLC patient has progression from a prior immunotherapy treatment with a PD-1 or PD-L1 antagonist given for a minimum of 12 weeks. In some embodiments, a prior immunotherapy may have been given with or without chemotherapy and may have been used in any line. In some embodiments, a NSCLC patient has one additional line of intervening chemotherapy following progression.

In some embodiments, a NSCLC patient has performance status of ECOG 0-1. In some embodiments, a NSCLC patient has ECOG performance status grade 0. In some embodiments, a NSCLC patient has ECOG performance status grade 1. ECOG performance status is discussed in Oken M, Creech R, Tormey D, et al. "Toxicity and response criteria of the Eastern Cooperative Oncology Group" Am J Clin Oncol. 1982; 5:649-655. ECOG performance status grade 0 refers to patients who are fully active, and are able to carry on all pre-disease performance without restriction. ECOG performance status grade 1 refers to patients who are restricted in physically strenuous activity but ambulatory and able to carry out work of a light or sedentary nature, e.g., light house work, office work.

In some embodiments, a NSCLC patient has adequate bone marrow, renal, and hepatic function as follows (within 7 days of starting therapy):

Absolute neutrophil count (ANC)≥1000/μL; and/or

Hemoglobin>9 g/dl; and/or

Platelet Count>75,000/μL; and/or

Serum creatinine≤1.5×upper limit of normal (ULN) or glomerular filtration rate (GFR)>40 mL/min for subject with creatinine levels>1.5×institutional ULN (using the Cockcroft-Gault formula); and/or Serum total bilirubin≤1.5×ULN or direct bilirubin≤ ULN for subjects with total bilirubin levels>1.5 ULN; and/or Aspartate aminotransferase (AST) and alanine aminotransferase (ALT)≤2.5×

ULN (or ≤5× if liver metastases are present).

In some embodiments, a NSCLC patient has recovered to grade 1 or baseline for all clinically significant on-going adverse events (AEs) from prior therapy.

In some embodiments, a NSCLC patient does not have recent (within the last 12 months) history of inflammatory bowel disease (IBD), including Crohn's disease and ulcerative colitis, or non-infectious interstitial lung disease.

In some embodiments, a NSCLC patient does not have current use of nonsteroidal anti-inflammatory drugs (NSAIDs) or cyclooxygenase-2 (COX-2) inhibitors within 3 days before treatment initiation or at any time during the study unless used for management of adverse events. In some embodiments, a NSCLC patient does not use an aspirin product, or only use it at prophylactic cardiovascular doses.

In some embodiments, a NSCLC patient does not have recent (within the last 12 months) or current gastrointestinal (GI) ulcer or colitis (other than IBD) or clinically significant autoimmune disease (i.e. severe) requiring continuous systemic immunosuppressive therapy.

In some embodiments, a NSCLC patient does not have a history of severe hypersensitivity reactions to PD-1 antibodies.

In some embodiments, a NSCLC patient has not received a live vaccine within 30 days prior to the planned first dose of the instant treatment.

In some embodiments, a NSCLC patient does not have any condition requiring continuous systemic treatment with either corticosteroids (>10 mg daily prednisone equivalents) or other immunosuppressive medications within 2 weeks prior to first dose of the instant treatment. In some embodiments, a NSCLC patient has inhaled or topical steroids and physiological replacement doses of up to 10 mg daily prednisone equivalent in the absence of active autoimmune disease.

In some embodiments, a NSCLC patient does not have a known EGFR, ALK, or ROS gene alteration.

In some embodiments, a NSCLC patient has a history of smoking.

In some embodiments, a NSCLC patient does not have uncontrolled or life-threatening symptomatic concomitant disease (including known symptomatic HIV, symptomatic Hepatitis B and C, or active tuberculosis [TB]).

In some embodiments, a NSCLC patient has not received chemotherapy or an investigational agent or device, or undergone a major surgery or systemic radiation within 3 weeks of starting the instant treatment, or had inadequate healing or recovery from complications of any of these prior to starting the instant treatment.

In some embodiments, a NSCLC patient has not had potentially life-threatening second malignancy within 3 years before starting the instant treatment.

In some embodiments, a NSCLC patient does not have clinically unstable central nervous system (CNS)/brain metastasis (treated or stable CNS metastases allowed).

In some embodiments, a NSCLC patient does not have any other concurrent antineoplastic treatment except for allowed local radiation of lesions for palliation (to be considered non-target lesions after treatment).

In some embodiments, a NSCLC patient does not have clinically significant (i.e., active) cardiovascular disease, including but not being limited to:

cerebral vascular accident/stroke (<6 months prior to enrollment); and/or myocardial infarction (<6 months prior to enrollment); and/or unstable angina; and/or congestive heart failure (≥New York Heart Association Classification Class II); and/or serious cardiac arrhythmia requiring medication.

In some embodiments, a NSCLC patient does not have medical conditions requiring concomitant administration of strong CYP3A4 or P-glycoprotein inhibitors or inducers.

In some embodiments, a NSCLC patient is not pregnant or breastfeeding, or expecting to conceive children during the instant treatment.

In some embodiments, a NSCLC patient is with advanced or metastatic Post-PD-1/L1 Non-Small Cell Lung Cancer (NSCLC) adenocarcinoma.

In some embodiments, a NSCLC patient is an adult patient diagnosed with NSCLC who has been previously treated for a minimum of 12 weeks with any PD-1 or PD-L1 checkpoint inhibitor.

In some embodiments, a NSCLC patient is treated with grapiprant at a starting dose level of 300 mg twice a day (BID). In some embodiments, a NSCLC patient is treated with grapiprant and pembrolizumab for up to 2 years.

In some embodiments, a NSCLC patient is an adult patient with a histologically confirmed non-small cell lung cancer (NSCLC) adenocarcinoma.

In some embodiments, a NSCLC patient has an advanced (stage IIIb) disease that is not amenable to curative intent treatment with concurrent chemoradiation and metastatic (stage IV) patients.

In some embodiments, a NSCLC patient has progressed clinically and/or radiographically per RECIST v1.1 after receiving a PD-1 or PD-L1 antagonist for a minimum of 12 weeks. In some embodiments, a NSCLC patient has received Immunotherapy with chemotherapy. In some embodiments, a NSCLC patient has received Immunotherapy without chemotherapy. In some embodiments, a NSCLC patient has received Immunotherapy in any line. In some embodiments, a NSCLC patient has received no more than one prior regimen of immunotherapy.

In some embodiments, a NSCLC patient has measurable disease per RECIST v1.1 as assessed by the local site investigator/radiology. In some embodiments, lesions situated in a previously irradiated area are considered measurable if progression has been demonstrated in such lesions.

In some embodiments, a NSCLC patient has a disease that can be safely accessed via bronchoscopic, thoracoscopic or percutaneous biopsy for multiple core biopsies (minimum of 3 passes per biopsy).

In some embodiments, a NSCLC patient has an Eastern Cooperative Oncology Group (ECOG) performance status of 0 to 1.

In some embodiments, a NSCLC patient has adequate organ function as defined in Table A below.

In some embodiments, a NSCLC patient does not use NSAIDs (eg, ibuprophen, naproxen), COX-2 inhibitors (eg, celecoxib) within 3 days before treatment initiation or at any time during the treatment. In some embodiments, a NSCLC patient uses NSAIDs (eg, ibuprophen, naproxen), COX-2 inhibitors (eg, celecoxib) within 3 days before treatment initiation or at any time during the treatment for management of AE. In some embodiments, a NSCLC patient uses Aspirin products that is limited to prophylactic cardiovascular doses.

In some embodiments, a NSCLC patient does not have a known epidermal growth factor receptor (EGFR), anaplastic lymphoma kinase (ALK), or ROS gene alteration.

In some embodiments, a NSCLC patient does not have a known BRAF gene mutation.

In some embodiments, a NSCLC patient has a history of smoking (>100 cigarettes lifetime).

In some embodiments, a NSCLC patient does not have a history of severe hypersensitivity reactions to a PD-1/L1 antibody.

In some embodiments, a NSCLC patient has not received prior systemic anti-cancer therapy including investigational agents within 4 weeks prior to treatment. In some embodiments, a NSCLC patient has recovered from all AEs due to previous therapies to ≤Grade 1 or baseline. In some embodiments, a NSCLC patient has ≤Grade 2 neuropathy.

In some embodiments, a NSCLC patient has not received prior radiotherapy within 2 weeks of start of a treatment of the invention. In some embodiments, a NSCLC patient has recovered from all radiation-related toxicities, not require corticosteroids, and not have had radiation pneumonitis. In some embodiments, a NSCLC patient has a 1-week washout for palliative radiation (≤2 weeks of radiotherapy) to non-central nervous system (CNS) disease. In some embodiments, a NSCLC patient does not receive any antineoplastic treatment during a treatment of the invention, except for allowed local radiation of lesions for palliation only (to be considered non-target lesions after treatment). In some embodiments, a NSCLC patient has received a surgery, and recovered fully from the toxicity and/or complications from the intervention prior to starting a treatment of the invention.

In some embodiments, a NSCLC patient has not received a live vaccine within 30 days prior to the first dose of study treatment.

In some embodiments, a NSCLC patient has not taken strong CYP3A4 or P-glycoprotein inhibitors or inducers prior to and during a treatment of the invention. In some embodiments, a NSCLC patient has taken strong CYP3A4 or P-glycoprotein inhibitors or inducers, but transferred to other medications within ≥5 half-lives prior to dosing of a treatment of the invention.

In some embodiments, a NSCLC patient does not participate in or has not participated in a study of an investigational agent within 4 weeks prior to the first dose of a treatment of the invention. In some embodiments, a NSCLC patient has not used an investigational device within 4 weeks prior to the first dose of a treatment of the invention.

In some embodiments, a NSCLC patient does not have a diagnosis of immunodeficiency. In some embodiments, a NSCLC patient is not receiving chronic systemic steroid therapy (in dosing exceeding 10 mg daily of prednisone equivalent), or any other form of immunosuppressive therapy, within 7 days prior the first dose of a treatment of the invention.

In some embodiments, a NSCLC patient does not have a known additional potentially life-threatening malignancy that is progressing or has required active treatment within 3 years prior to the first dose of a treatment of the invention. In some embodiments, a NSCLC patient has a basal cell carcinoma of the skin. In some embodiments, a NSCLC patient has squamous cell carcinoma of the skin. In some embodiments, a NSCLC patient has carcinoma in situ (eg, breast carcinoma, cervical cancer in situ) that have undergone potentially curative therapy.

In some embodiments, a NSCLC patient does not have known active CNS metastases and/or carcinomatous meningitis (clinically stable and/or previously treated inactive CNS metastases allowed).

In some embodiments, a NSCLC patient does not have an active autoimmune disease that has required systemic treatment in past 2 years (ie, with use of disease modifying agents, corticosteroids or immunosuppressive drugs). In some embodiments, a systemic treatment is not replacement therapy (eg, thyroxine, insulin, or physiologic corticosteroid replacement therapy for adrenal or pituitary insufficiency). In some embodiments, an autoimmune disease is inflammatory bowel disease (IBD) such as Crohn's disease and ulcerative colitis.

In some embodiments, a NSCLC patient does not have a history of (non-infectious) pneumonitis that required steroids or has current pneumonitis.

In some embodiments, a NSCLC patient does not have an active infection requiring systemic therapy.

In some embodiments, a NSCLC patient does not have recent (within the last 12 months) or current GI ulcer or colitis or non-immune colitis.

In some embodiments, a NSCLC patient does not have a known history of human immunodeficiency virus (HIV) infection.

In some embodiments, a NSCLC patient does not have a known history of Hepatitis B or known active Hepatitis C virus infection.

In some embodiments, a NSCLC patient does not have clinically significant (ie, active) cardiovascular disease: cerebral vascular accident/stroke (<6 months prior to enrollment), myocardial infarction (<6 months prior to enrollment), unstable angina, congestive heart failure (≥New York Heart Association Classification Class II), or uncontrolled cardiac arrhythmia.

In some embodiments, a NSCLC patient does not have a known psychiatric or substance abuse disorder that would interfere with cooperating with a treatment of the invention.

In some embodiments, a NSCLC patient is not a woman of childbearing potential (WOCBP) who has a positive pregnancy test prior to a treatment of the invention.

In some embodiments, a NSCLC patient is not breastfeeding or expecting to conceive or father children within the projected duration of a treatment of the invention.

CRC patients

In some embodiments, a CRC patient is histologically confirmed advanced, metastatic, or progressive colorectal cancer (CRC). In some embodiments, microsatellite stable disease (MSS) is based on prior PCR or immunohistochemistry results.

In some embodiments, a CRC patient is at least 18 years old.

In some embodiments, a CRC patient has progressed on first line 5-FU based therapy, refused therapy or is intolerable to 5-FU based therapy.

In some embodiments, a CRC patient has a measurable disease as per RECIST 1.1 (Response Evaluation Criteria in Solid Tumors).

In some embodiments, a CRC patient has a performance status of ECOG 0-1. In some embodiments, a CRC patient has ECOG performance status grade 0. In some embodiments, a CRC patient has ECOG performance status grade 1.

In some embodiments, a CRC patient has adequate bone marrow, renal, and hepatic function as follows (within 7 days of starting therapy):

Absolute neutrophil count (ANC)≥1000/µL; and/or
Hemoglobin>9 g/dl; and/or
Platelet Count>75,000/µl; and/or
Serum creatinine≤1.5×upper limit of normal (ULN) or glomerular filtration rate (GFR)≥40 mL/min for subject with creatinine levels>1.5×institutional ULN (using the Cockcroft-Gault formula); and/or
Serum total bilirubin≤1.5×ULN or direct bilirubin≤ ULN for subjects with total bilirubin levels>1.5 ULN; and/or
Aspartate aminotransferase (AST) and alanine aminotransferase (ALT)≤2.5×ULN (or ≤5× if liver metastases are present).

In some embodiments, a CRC patient has recovered to Grade 1 or baseline for all clinically significant on-going adverse events (AEs) from prior therapy.

In some embodiments, a CRC patient has completed previous treatment (including other investigational therapy) at least 3 weeks before initiation of the instant treatment.

In some embodiments, a CRC patient has not been treated with an anti-PD-1, anti-PD-L1, or anti-PD-L2 therapeutic antibody.

In some embodiments, a CRC patient has not used non-steroidal anti-inflammatory drugs (NSAIDs) or cyclooxygenase-2 (COX-2) inhibitors within 3 days before initiation of the instant treatment, or at any time during the instant treatment, unless used for management of AE. In some embodiments, a CRC patient does not use any aspirin product, or only use it at prophylactic cardiovascular doses.

In some embodiments, a CRC patient does not have a recent (within the last 12 months) history of inflammatory bowel disease (IBD), including Crohn's disease and ulcerative colitis, or non-infectious interstitial lung disease.

In some embodiments, a CRC patient does not have recent (within the last 12 months) or current gastrointestinal (GI) ulcer or colitis (other than IBD) or clinically significant autoimmune disease (i.e. severe) requiring continuous systemic immunosuppressive therapy.

In some embodiments, a CRC patient does not have any condition requiring continuous systemic treatment with either corticosteroids (>10 mg daily prednisone equivalents) or other immunosuppressive medications within 2 weeks prior to first dose of the instant treatment. In some embodiments, a CRC patient takes inhaled or topical steroids and physiological replacement doses of up to 10 mg daily prednisone equivalent in the absence of active clinically significant (severe) autoimmune disease.

In some embodiments, a CRC patient does not have a history of severe hypersensitivity reactions to chimeric or humanized antibodies.

In some embodiments, a CRC patient has not received a live vaccine within 30 days prior to the first dose of the instant treatment.

In some embodiments, a CRC patient does not receive any other concurrent antineoplastic treatment except for allowed local radiation of lesions for palliation only (to be considered non-target lesions after treatment).

In some embodiments, a CRC patient does not have uncontrolled or life-threatening symptomatic concomitant disease (including known symptomatic HIV, symptomatic Hepatitis B and C, or active tuberculosis [TB]).

In some embodiments, a CRC patient has not undergone a major surgery or systemic radiation within 3 weeks of starting the instant treatment or has inadequate healing or recovery from complications of surgery or radiation prior to starting the instant treatment.

In some embodiments, a CRC patient has not had a potentially life-threatening second malignancy within the last 3 years.

In some embodiments, a CRC patient does not have clinically unstable central nervous system (CNS)/brain metastasis (treated or stable CNS metastases allowed).

In some embodiments, a CRC patient has not had a clinically significant (i.e., active) cardiovascular disease, including but not being limited to:

cerebral vascular accident/stroke (<6 months prior to enrollment); and/or
myocardial infarction (<6 months prior to enrollment); and/or
unstable angina; and/or
congestive heart failure (≥New York Heart Association Classification Class II); and/or
serious cardiac arrhythmia requiring medication.

In some embodiments, a CRC patient does not have medical conditions requiring concomitant administration of strong CYP3A4 or P-glycoprotein inhibitors or inducers.

In some embodiments, a CRC patient is with advanced or progressive MSS CRC.

In some embodiments, a CRC patient is treated at a starting dose of Grapiprant 300 mg administered orally twice a day (BID).

In some embodiments, a CRC patient is treated with grapiprant 300 mg administered orally BID, and pembrolizumab administered 200 mg IV every 3 weeks (Q3W).

In some embodiments, a CRC patient is an adult patient with a histologically confirmed advanced, metastatic, or progressive CRC that is MSS. In some embodiments, microsatellite stability is based on prior polymerase chain reaction (PCR), Next-Gen sequencing, or immunohistochemistry results per institutional standards.

In some embodiments, a CRC patient has received at least two prior lines of therapy for advanced or metastatic CRC, at least one of which included fluorouracil. In some embodiments, a CRC patient has received adjuvant therapy, and progression occurs within 6 months of its completion.

In some embodiments, a CRC patient has measurable disease per RECIST v1.1 as assessed by the local site investigator/radiology. In some embodiments, lesions situated in a previously irradiated area are considered measurable if progression has been demonstrated in such lesions.

In some embodiments, a CRC patient has an accessible tumor that can be safely accessed for multiple core biopsies.

In some embodiments, a CRC patient has an Eastern Cooperative Oncology Group (ECOG) performance status of 0 to 1.

In some embodiments, a CRC patient has adequate organ function as defined in Table A below.

In some embodiments, a CRC patient is able to swallow and absorb oral tablets.

In some embodiments, a CRC patient is a woman who is not postmenopausal and uses contraception, or a man.

In some embodiments, a CRC patient has not received prior therapy with an anti-PD-1, anti-PD-L1, or anti-PD-L2 agent or with an agent directed to another stimulatory or co-inhibitory T-cell receptor (eg, CTLA-4, OX 40, CD137).

In some embodiments, a CRC patient does not use NSAIDs (eg, ibuprophen, naproxen), COX-2 inhibitors (eg, celecoxib) within 3 days before initiation of a treatment of the invention, or at any time during a treatment of the invention. In some embodiments, a CRC patient uses NSAIDs (eg, ibuprophen, naproxen), COX-2 inhibitors (eg, celecoxib) for management of AE of a treatment of the invention. In some embodiments, a CRC patient uses an aspirin product that is limited to prophylactic cardiovascular doses.

In some embodiments, a CRC patient does not have history of severe hypersensitivity reactions to chimeric or humanized antibodies.

In some embodiments, a CRC patient has not received prior systemic anti-cancer therapy including investigational agents within 4 weeks (or 5 half-lives, whichever is shorter) prior to a treatment of the invention. In some embodiments, a CRC patient has recovered from all AEs due to previous therapies to ≤Grade 1 or baseline. In some embodiments, a CRC patient is with ≤Grade 2 neuropathy. In some embodiments, a CRC patient has received major surgery, and has fully recovered from the toxicity and/or complications from the intervention prior to starting a treatment of the invention.

In some embodiments, a CRC patient has not received prior radiotherapy within 2 weeks of start of a treatment of the invention. In some embodiments, a CRC patient has recovered from all radiation-related toxicities, does not require corticosteroids, and has not had radiation pneumonitis. In some embodiments, a CRC patient has a 1-week washout for palliative radiation (≤2 weeks of radiotherapy) to non-central nervous system (CNS) disease. In some embodiments, a CRC patient does not receive antineoplastic treatment concurrently with a treatment of the invention. In some embodiments, a CRC patient receives antineoplastic treatment for local radiation of lesions for palliation only (to be considered non-target lesions after treatment).

In some embodiments, a CRC patient has not received a live vaccine within 30 days prior to the first dose of a treatment of the invention.

In some embodiments, a CRC patient does not take strong CYP3A4 or P-glycoprotein inhibitors or inducers. In some embodiments, a CRC patient has taken strong CYP3A4 or P-glycoprotein inhibitors or inducers, but transferred to other medications within ≥5 half-lives prior to dosing of a treatment of the invention.

In some embodiments, a CRC patient does not participate in, or has not participated in, a study of an investigational agent within 4 weeks prior to the first dose of a treatment of the invention. In some embodiments, a CRC patient has not used an investigational device within 4 weeks prior to the first dose of a treatment of the invention.

In some embodiments, a CRC patient does not have a diagnosis of immunodeficiency. In some embodiments, a CRC patient does not receive chronic systemic steroid therapy (in dosing exceeding 10 mg daily of prednisone equivalent), or any other form of immunosuppressive therapy, within 7 days prior to the first dose of a treatment of the invention.

In some embodiments, a CRC patient does not have a known additional potentially life-threatening malignancy that is progressing or has required active treatment within 3 years prior to start of a treatment of the invention. In some embodiments, a CRC patient has basal cell carcinoma of the skin. In some embodiments, a CRC patient has squamous cell carcinoma of the skin. In some embodiments, a CRC patient has carcinoma in situ (eg, breast carcinoma, cervical cancer in situ) that has undergone potentially curative therapy.

In some embodiments, a CRC patient does not have known active CNS metastases and/or carcinomatous meningitis. In some embodiments, a CRC patient is with previously treated brain metastases and is radiologically stable, ie, without evidence of progression for at least 4 weeks by repeat imaging (note that the repeat imaging should be performed during study screening), and/or clinically stable and without requirement of steroid treatment for at least 14 days prior to first dose of a treatment of the invention.

In some embodiments, a CRC patient does not have an active autoimmune disease that has required systemic treatment (ie, with use of disease modifying agents, corticosteroids or immunosuppressive drugs) in 2 years prior to start of a treatment of the invention. In some embodiments, a CRC patient has received replacement therapy (eg, thyroxine, insulin, or physiologic corticosteroid replacement therapy for adrenal or pituitary insufficiency) in 2 years prior to start of a treatment of the invention. In some embodiments, an autoimmune disease includes but is not limited to inflammatory bowel disease (IBD) such as Crohn's disease and ulcerative colitis.

In some embodiments, a CRC patient does not have a history of (non-infectious) pneumonitis that required steroids or has current pneumonitis.

In some embodiments, a CRC patient does not have an active infection requiring systemic therapy.

In some embodiments, a CRC patient does not have recent (within 12 months from start of a treatment of the invention) or current GI ulcer or non-immune colitis.

In some embodiments, a CRC patient does not have a known history of human immunodeficiency virus (HIV) infection.

In some embodiments, a CRC patient does not have a known history of Hepatitis B or known active Hepatitis C virus infection.

In some embodiments, a CRC patient does not have clinically significant (ie, active) cardiovascular disease: cerebral vascular accident/stroke (<6 months prior to enrollment), myocardial infarction (<6 months prior to enrollment), unstable angina, congestive heart failure (≥ New York Heart Association Classification Class II), or uncontrolled cardiac arrhythmia.

In some embodiments, a CRC patient does not have a known psychiatric or substance abuse disorder that would interfere with cooperating with a treatment of the invention.

In some embodiments, a CRC patient is not a woman of childbearing potential (WOCBP) who has a positive pregnancy test prior to a treatment of the invention.

In some embodiments, a CRC patient does not breastfeed or expect to conceive or father children within a treatment of the invention.

Cancer

Cancer includes, in some embodiments, without limitation, leukemias (e.g., acute leukemia, acute lymphocytic leukemia, acute myelocytic leukemia, acute myeloblastic leukemia, acute promyelocytic leukemia, acute myelomonocytic leukemia, acute monocytic leukemia, acute erythroleukemia, chronic leukemia, chronic myelocytic leukemia, chronic lymphocytic leukemia), polycythemia vera, lymphoma (e.g., Hodgkin's disease or non-Hodgkin's disease), Waldenstrom's macroglobulinemia, multiple myeloma, heavy chain disease, and solid tumors such as sarcomas and carcinomas (e.g., fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, uterine cancer, testicular cancer, lung carcinoma, small cell lung carcinoma, bladder carcinoma, epithelial carcinoma, glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, and retinoblastoma).

In some embodiments, the cancer is glioma, astrocytoma, glioblastoma multiforme (GBM, also known as glioblastoma), medulloblastoma, craniopharyngioma, ependymoma, pinealoma, hemangioblastoma, acoustic neuroma, oligodendroglioma, schwannoma, neurofibrosarcoma, meningioma, melanoma, neuroblastoma, or retinoblastoma.

In some embodiments, the cancer is acoustic neuroma, astrocytoma (e.g. Grade I-Pilocytic Astrocytoma, Grade II-Low-grade Astrocytoma, Grade III-Anaplastic Astrocytoma, or Grade IV-Glioblastoma (GBM)), chordoma, CNS lymphoma, craniopharyngioma, brain stem glioma, ependymoma, mixed glioma, optic nerve glioma, subependymoma, medulloblastoma, meningioma, metastatic brain tumor, oligodendroglioma, pituitary tumors, primitive neuroectodermal (PNET) tumor, or schwannoma. In some embodiments, the cancer is a type found more commonly in children than adults, such as brain stem glioma, craniopharyngioma, ependymoma, juvenile pilocytic astrocytoma (JPA), medulloblastoma, optic nerve glioma, pineal tumor, primitive neuroectodermal tumors (PNET), or rhabdoid tumor. In some embodiments, the patient is an adult human. In some embodiments, the patient is a child or pediatric patient.

Cancer includes, in another embodiment, without limitation, mesothelioma, hepatobilliary (hepatic and billiary duct), bone cancer, pancreatic cancer, skin cancer, cancer of the head or neck, cutaneous or intraocular melanoma, ovarian cancer, colon cancer, rectal cancer, cancer of the anal region, stomach cancer, gastrointestinal (gastric, colorectal, and duodenal), uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, testicular cancer, chronic or acute leukemia, chronic myeloid leukemia, lymphocytic lymphomas, cancer of the bladder, cancer of the kidney or ureter, renal cell carcinoma, carcinoma of the renal pelvis, non-Hodgkins's lymphoma, spinal axis tumors, brain stem glioma, pituitary adenoma, adrenocortical cancer, gall bladder cancer, multiple myeloma, cholangiocarcinoma, fibrosarcoma, neuroblastoma, retinoblastoma, or a combination of one or more of the foregoing cancers.

In some embodiments, the cancer is selected from hepatocellular carcinoma, ovarian cancer, ovarian epithelial cancer, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical adenoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from hepatocellular carcinoma (HCC), hepatoblastoma, colon cancer, rectal cancer, ovarian cancer, ovarian epithelial cancer, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical adenoma, pancreatic cancer, pancreatic ductal carcinoma, pancreatic adenocarcinoma, glioma, neurofibromatosis-1 associated malignant peripheral sheath tumors (MPNST), Waldenstrom's macroglobulinemia, or medulloblastoma.

In some embodiments, the cancer is a solid tumor, such as a sarcoma, carcinoma, or lymphoma. Solid tumors generally comprise an abnormal mass of tissue that typically does not include cysts or liquid areas. In some embodiments, the cancer is selected from renal cell carcinoma, or kidney cancer; hepatocellular carcinoma (HCC) or hepatoblastoma, or liver cancer; melanoma; breast cancer; colorectal carcinoma, or colorectal cancer; colon cancer; rectal cancer; anal cancer; lung cancer, such as non-small cell lung cancer (NSCLC) or small cell lung cancer (SCLC); ovarian cancer, ovarian epithelial cancer, ovarian carcinoma, or fallopian tube cancer; papillary serous cystadenocarcinoma or uterine papillary serous carcinoma (UPSC); prostate cancer; testicular cancer; gallbladder cancer; hepatocholangiocarcinoma; soft tissue and bone synovial sarcoma; rhabdomyosarcoma; osteosarcoma; chondrosarcoma; Ewing sarcoma; anaplastic thyroid cancer; adrenocortical carcinoma; pancreatic cancer; pancreatic ductal carcinoma or pancreatic adenocarcinoma; gastrointestinal/stomach (GIST) cancer; lymphoma; squamous cell carcinoma of the head and neck (SCCHN); salivary gland cancer; glioma, or brain cancer; neurofibromatosis-1 associated malignant peripheral nerve sheath tumors (MPNST); Waldenstrom's macroglobulinemia; or medulloblastoma.

In some embodiments, the cancer is selected from renal cell carcinoma, hepatocellular carcinoma (HCC), hepatoblastoma, colorectal carcinoma, colorectal cancer, colon cancer, rectal cancer, anal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, chondrosarcoma, anaplastic thyroid cancer, adrenocortical carcinoma, pancreatic cancer, pancreatic ductal carcinoma, pancreatic adenocarcinoma, glioma, brain cancer, neurofibromatosis-1 associated malignant peripheral nerve sheath tumors (MPNST), Waldenstrom's macroglobulinemia, or medulloblastoma.

In some embodiments, the cancer is selected from hepatocellular carcinoma (HCC), hepatoblastoma, colon cancer, rectal cancer, ovarian cancer, ovarian epithelial cancer, ovarian carcinoma, fallopian tube cancer, papillary serous cystadenocarcinoma, uterine papillary serous carcinoma (UPSC), hepatocholangiocarcinoma, soft tissue and bone synovial sarcoma, rhabdomyosarcoma, osteosarcoma, anaplastic thyroid cancer, adrenocortical carcinoma, pancreatic cancer, pancreatic ductal carcinoma, pancreatic adenocarcinoma, glioma, neurofibromatosis-1 associated malignant peripheral nerve sheath tumors (MPNST), Waldenstrom's macroglobulinemia, or medulloblastoma.

In some embodiments, the cancer is hepatocellular carcinoma (HCC). In some embodiments, the cancer is hepatoblastoma. In some embodiments, the cancer is colon cancer. In some embodiments, the cancer is rectal cancer. In some embodiments, the cancer is ovarian cancer, or ovarian carcinoma. In some embodiments, the cancer is ovarian epithelial cancer. In some embodiments, the cancer is fallopian tube cancer. In some embodiments, the cancer is papillary serous cystadenocarcinoma. In some embodiments, the cancer is uterine papillary serous carcinoma (UPSC). In some embodiments, the cancer is hepatocholangiocarcinoma. In some embodiments, the cancer is soft tissue and bone synovial sarcoma. In some embodiments, the cancer is rhabdomyosarcoma. In some embodiments, the cancer is osteosarcoma. In some embodiments, the cancer is anaplastic thyroid cancer. In some embodiments, the cancer is adrenocortical carcinoma. In some embodiments, the cancer is pancreatic cancer, or pancreatic ductal carcinoma. In some embodiments, the cancer is pancreatic adenocarcinoma. In some embodiments, the cancer is glioma. In some embodiments, the cancer is malignant peripheral nerve sheath tumors (MPNST). In some embodiments, the cancer is neurofibromatosis-1 associated MPNST. In some embodiments, the cancer is Waldenstrom's macroglobulinemia. In some embodiments, the cancer is medulloblastoma.

In some embodiments, the cancer is Acute Lymphoblastic Leukemia (ALL), Acute Myeloid Leukemia (AML), Adrenocortical Carcinoma, Anal Cancer, Appendix Cancer, Atypical Teratoid/Rhabdoid Tumor, Basal Cell Carcinoma, Bile Duct Cancer, Bladder Cancer, Bone Cancer, Brain Tumor, Astrocytoma, Brain and Spinal Cord Tumor, Brain Stem Glioma, Central Nervous System Atypical Teratoid/Rhabdoid Tumor, Central Nervous System Embryonal Tumors, Breast Cancer, Bronchial Tumors, Burkitt Lymphoma, Carcinoid Tumor, Carcinoma of Unknown Primary, Central Nervous System Cancer, Cervical Cancer, Childhood Cancers, Chordoma, Chronic Lymphocytic Leukemia (CLL), Chronic Myelogenous Leukemia (CML), Chronic Myeloproliferative Disorders, Colon Cancer, Colorectal Cancer, Craniopharyngioma, Cutaneous T-Cell Lymphoma, Ductal Carcinoma In Situ (DCIS), Embryonal Tumors, Endometrial Cancer, Ependymoblastoma, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Fibrous Histiocytoma of Bone, Gallbladder Cancer, Gastric Cancer, Gastrointestinal Carcinoid Tumor, Gastrointestinal Stromal Tumors (GIST), Germ Cell Tumor, Ovarian Germ Cell Tumor, Gestational Trophoblastic Tumor, Glioma, Hairy Cell Leukemia, Head and Neck Cancer, Heart Cancer, Hepatocellular Cancer, Histiocytosis, Langerhans Cell Cancer, Hodgkin Lymphoma, Hypopharyngeal Cancer, Intraocular Melanoma, Islet Cell Tumors, Kaposi Sarcoma, Kidney Cancer, Langerhans Cell Histiocytosis, Laryngeal Cancer, Leukemia, Lip and Oral Cavity Cancer, Liver Cancer, Lobular Carcinoma In Situ (LCIS), Lung Cancer, Lymphoma, AIDS-Related Lymphoma, Macroglobulinemia, Male Breast Cancer, Medulloblastoma, Medulloepithelioma, Melanoma, Merkel Cell Carcinoma, Malignant Mesothelioma, Metastatic Squamous Neck Cancer with Occult Primary, Midline Tract Carcinoma Involving NUT Gene, Mouth Cancer, Multiple Endocrine Neoplasia Syndrome, Multiple Myeloma/Plasma Cell Neoplasm, Mycosis Fungoides, Myelodysplastic Syndrome, Myelodysplastic/Myeloproliferative Neoplasm, Chronic Myelogenous Leukemia (CML), Acute Myeloid Leukemia (AML), Myeloma, Multiple Myeloma, Chronic Myeloproliferative Disorder, Nasal Cavity Cancer, Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip Cancer, Oropharyngeal Cancer, Osteosarcoma, Ovarian Cancer, Pancreatic Cancer, Papillomatosis, Paraganglioma, Paranasal Sinus Cancer, Nasal Cavity Cancer, Parathyroid Cancer, Penile Cancer, Pharyngeal Cancer, Pheochromocytoma, Pineal Parenchymal Tumors of Intermediate Differentiation, Pineoblastoma, Pituitary Tumor, Plasma Cell Neoplasm, Pleuropulmonary Blastoma, Breast Cancer, Primary Central Nervous System (CNS) Lymphoma, Prostate Cancer, Rectal Cancer, Renal Cell Cancer, Clear cell renal cell carcinoma, Renal Pelvis Cancer, Ureter Cancer, Transitional Cell Cancer, Retinoblastoma, Rhabdomyosarcoma, Salivary Gland Cancer, Sarcoma, Sezary Syndrome, Skin Cancer, Small Cell Lung Cancer, Small Intestine Cancer, Soft Tissue Sarcoma, Squamous Cell Carcinoma, Squamous Neck Cancer with Occult Primary, Squamous Cell Carcinoma of the Head and Neck (HNSCC), Stomach Cancer, Supratentorial Primitive Neuroectodermal Tumors, T-Cell Lymphoma, Testicular Cancer, Throat Cancer, Thymoma, Thymic Carcinoma, Thyroid Cancer, Transitional Cell Cancer of the Renal Pelvis and Ureter, Triple Negative Breast Cancer (TNBC), Gestational Trophoblastic Tumor, Unknown Primary, Unusual Cancer of Childhood, Urethral Cancer, Uterine Cancer, Uterine Sarcoma, Waldenstrom Macroglobulinemia, or Wilms Tumor.

In certain embodiments, the cancer is selected from bladder cancer, breast cancer (including TNBC), cervical cancer, colorectal cancer, chronic lymphocytic leukemia (CLL), diffuse large B-cell lymphoma (DLBCL), esophageal adenocarcinoma, glioblastoma, head and neck cancer, leukemia (acute and chronic), low-grade glioma, lung cancer (including adenocarcinoma, non-small cell lung cancer, and squamous cell carcinoma), Hodgkin's lymphoma, non-Hodgkin lymphoma (NHL), melanoma, multiple myeloma (MM), ovarian cancer, pancreatic cancer, prostate cancer, renal cancer (including renal clear cell carcinoma and kidney papillary cell carcinoma), and stomach cancer.

In some embodiments, the cancer is small cell lung cancer, non-small cell lung cancer, colorectal cancer, multiple myeloma, acute myeloid leukemia (AML), acute lymphoblastic leukemia (ALL), pancreatic cancer, liver cancer, hepatocellular cancer, neuroblastoma, other solid tumors or other hematological cancers.

In some embodiments, the cancer is small cell lung cancer, non-small cell lung cancer, colorectal cancer, multiple myeloma, or AML.

The present invention further features methods and compositions for the diagnosis, prognosis and treatment of viral-associated cancers, including human immunodeficiency virus (HIV) associated solid tumors, human papilloma virus (HPV)-16 positive incurable solid tumors, and adult T-cell leukemia, which is caused by human T-cell leukemia virus type I (HTLV-I) and is a highly aggressive form of CD4+ T-cell leukemia characterized by clonal integration of HTLV-I in leukemic cells (See https://clinicaltrials.gov/ct2/show/study/NCT02631746); as well as virus-associated tumors in gastric cancer, nasopharyngeal carcinoma, cervical cancer, vaginal cancer, vulvar cancer, squamous cell carcinoma of the head and neck, and Merkel cell carcinoma. (See https://clinicaltrials.gov/ct2/show/study/NCT02488759; see also https://clinicaltrials.gov/ct2/show/study/NCT0240886; https://clinicaltrials.gov/ct2/show/NCT02426892)

In some embodiments, the present invention provides a method for treating a tumor in a patient in need thereof, comprising administering to the patient an agent that inhibits prostaglandin EP4 receptor (EP4) activity and, optionally, an additional therapeutic agent as described herein, or pharmaceutical compositions thereof described herein. In some embodiments, the tumor comprises any of the cancers described herein. In some embodiments, the tumor comprises melanoma cancer. In some embodiments, the tumor comprises breast cancer. In some embodiments, the tumor comprises lung cancer. In some embodiments the tumor comprises small cell lung cancer (SCLC). In some embodiments, the tumor comprises non-small cell lung cancer (NSCLC).

In some embodiments, the tumor is treated by arresting further growth of the tumor. In some embodiments, the tumor is treated by reducing the size (e.g., volume or mass) of the tumor by at least 5%, 10%, 25%, 50%, 75%, 90% or 99% relative to the size of the tumor prior to treatment. In some embodiments, tumors are treated by reducing the quantity of the tumors in the patient by at least 5%, 10%, 25%, 50%, 75%, 90% or 99% relative to the quantity of tumors prior to treatment.

Pharmaceutically Acceptable Compositions

The compounds and compositions, according to the method of the present invention, may be administered using any amount and any route of administration effective for treating or lessening the severity of a disease, disorder or condition described herein. The exact amount required will vary from subject to subject, depending on the species, age, and general condition of the subject, the severity of the disease or condition, the particular agent, its mode of administration, and the like. The compounds and compositions, according to the method of the present invention, are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the disease or disorder being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound as described herein, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According some embodiments, the invention provides a composition comprising an agent that inhibits EP4 activity and a pharmaceutically acceptable carrier, adjuvant, or vehicle. According some embodiments, the invention provides a composition comprising an agent that inhibits EP4 activity, an immuno-oncology agent, and a pharmaceutically acceptable carrier, adjuvant, or vehicle. In certain embodiments, the amount of an agent that inhibits EP4 activity in compositions of this invention is such that is effective to measurably inhibit EP4 activity, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

In some embodiments, an agent that inhibits EP4 activity and an immuno-oncology agent as described herein are administered in a single composition as a single dosage form. In some embodiments, an agent that inhibits EP4 activity and an immuno-oncology agent as described herein are administered separately as a multiple dosage regimen. If administered as a multiple dosage regime, the two agents may be administered simultaneously, sequentially or within a period of time from one another, for example within 1, 2, 3, 4, 5, 6, 7, 8, 9, 10, 11, 12, 13, 14, 15, 16, 17, 18, 20, 21, 22, 23, or 24 hours from one another. In some embodiments, the two agents are administerd as a multiple dosage regimen within greater than 24 hours aparts.

As used herein, the term "combination," "combined," and related terms refers to the simultaneous or sequential administration of therapeutic agents in accordance with this invention. For example, an agent that inhibits EP4 activity may be administered with an immuno-oncology agent simultaneously or sequentially in separate unit dosage forms; or an agent that inhibits EP4 activity may be administered with an immuno-oncology agent simultaneously in a single unit dosage form. Accordingly, the present invention provides a single unit dosage form comprising an agent that inhibits EP4 activity, an immuno-oncology agent, and a pharmaceutically acceptable carrier, adjuvant, or vehicle.

The amount of an agent that inhibits EP4 activity and an immuno-oncology agent that may be combined with the carrier materials to produce a single dosage form will vary depending upon the host treated and the particular mode of administration. Preferably, compositions of this invention should be formulated so that a dosage of between 0.01-100 mg/kg body weight/day of each agent can be administered.

In some embodiments, an agent that inhibits EP4 activity and an immuno-oncology agent may act synergistically. Therefore, the amount of each agent will be less than that required in a monotherapy utilizing only that therapeutic agent. In such compositions a dosage of between about 50% to about 100% of the amount normally administered of each agent can be administered. In some embodiments, each agent is administered at a dosage of about 50%, about 55%, about 60%, about 65%, about 70%, about 75%, about 80%, about 85%, about 90%, or about 95% of the amount normally administered of each agent. As used herein, the phrase "normally administered" means the amount an FDA approved therapeutic agent is approvied for dosing per the FDA label insert.

The amount of each agent present in the compositions of this invention will be no more than the amount that would normally be administered in a composition comprising that therapeutic agent as the only active agent. In some embodiments, the amount of each agent in the presently disclosed compositions will range from about 50% to 100% of the amount normally present in a composition comprising that agent as the only therapeutically active agent.

In some embodiments, an agent that inhibits EP4 activity and/or an immuno-oncology agent as described in, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with an agent that inhibits EP4 activity and/or an immuno-oncology agent as described in, or pharmaceutical compositions thereof, are another embodiment of the present invention.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

General Procedures

X-ray Powder Diffraction (XRPD): The Rigaku Smart-Lab X-ray diffraction system was configured for reflection Bragg-Brentano geometry using a line source X-ray beam. The x-ray source is a Cu Long Fine Focus tube that was operated at 40 kV and 44 ma. That source provides an incident beam profile at the sample that changes from a narrow line at high angles to a broad rectangle at low angles. Beam conditioning slits are used on the line X-ray source to ensure that the maximum beam size is less than 10 mm both along the line and normal to the line. The Bragg-Brentano geometry is a para-focusing geometry controlled by passive divergence and receiving slits with the sample itself acting as the focusing component for the optics. The inherent resolution of Bragg-Brentano geometry is governed in part by the diffractometer radius and the width of the receiving slit used. Typically, the Rigaku Smart-Lab is operated to give peak widths of $0.1°2\theta$ or less. The axial divergence of the X-ray beam is controlled by 5.0-degree Soller slits in both the incident and diffracted beam paths.

Powder samples were prepared in a low background Si holder using light manual pressure to keep the sample surfaces flat and level with the reference surface of the sample holder. Each sample was analyzed from 2 to $40° 2\theta$ using a continuous scan of $6° 2\theta$ per minute with an effective step size of $0.02° 2\theta$.

Differential Scanning calorimetry (DSC): DSC analyses were carried out using a TA Instruments Q2000 instrument. The instrument temperature calibration was performed using indium. The DSC cell was kept under a nitrogen purge of ~50 mL per minute during each analysis. The sample was placed in a standard, crimped, aluminum pan and was heated from 25° C. to 350° C. at a rate of 10° C. per minute.

Thermogravimetric (TG) Analysis: The TG analysis was carried out using a TA Instruments Q50 instrument. The instrument balance was calibrated using class M weights and the temperature calibration was performed using alumel. The nitrogen purge was ~40 mL per minute at the balance and ~60 mL per minute at the furnace. Each sample was placed into a pre-tared platinum pan and heated from 20° C. to 350° C. at a rate of 10° C. per minute.

Nuclear Magnetic Resonance (NMR) Spectroscopy: The 1H NMR spectra were acquired on a Bruker DRX-500 spectrometer located at the Chemistry Department of Purdue University. Samples were prepared by dissolving material in DMSO-d6. The solutions were filtered and placed into individual 5-mm NMR tubes for subsequent spectral acquisition. The temperature controlled (298K) 1H NMR spectra acquired on the DRX-500 utilized a 5-mm cryoprobe operating at an observing frequency of 499.89 MHz.

Example 1-Preparation of Forms A of Compound 1

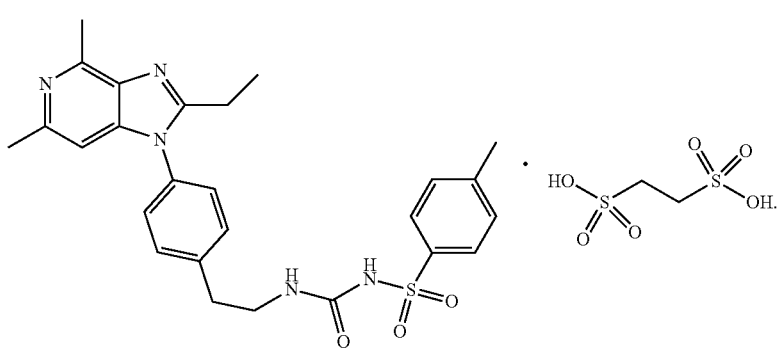

1

Form A of Compound 1

Form A of compound 1 was prepared by slurrying compound A with 1,2-ethanedisulfonic acid in acetone for 7 days at RT. The molar ratio of compound A to 1,2-ethanedisulfonic acid was about 1:1. The resulting solid material was analyzed by XRPD, DSC, TG and NMR.

Table 1, supra, is reproduced below and sets forth the X-ray diffraction peaks observed for Form A of compound 1.

TABLE 1

XRPD Peak Positions for Form A of Compound 1

| Position [°2θ] | Intensity [%] |
| --- | --- |
| 4.0 | 71.6 |
| 6.2 | 15.98 |
| 6.7 | 39.98 |
| 7.3 | 3.08 |
| 8.1 | 50.62 |
| 9.1 | 12.66 |
| 9.9 | 8.31 |
| 11.2 | 27.74 |
| 12.2 | 22.36 |
| 13.0 | 100 |
| 13.3 | 42.29 |
| 13.8 | 38.6 |
| 14.7 | 17.47 |
| 15.2 | 70.22 |
| 15.3 | 12.2 |
| 15.9 | 24.11 |
| 17.3 | 4.53 |
| 17.7 | 3.19 |
| 18.3 | 44.39 |
| 18.7 | 43.29 |
| 20.0 | 17.3 |
| 20.2 | 5.08 |
| 21.0 | 54.75 |
| 21.5 | 53.97 |
| 22.0 | 74.63 |

TABLE 1-continued

XRPD Peak Positions for Form A of Compound 1

| Position [°2θ] | Intensity [%] |
| --- | --- |
| 22.2 | 62.86 |
| 22.6 | 16.25 |
| 22.9 | 42.78 |
| 23.5 | 17.78 |
| 23.7 | 15.33 |
| 24.1 | 21.44 |
| 26.1 | 17 |
| 28.0 | 26.35 |
| 28.7 | 7.07 |

TABLE 1-continued

XRPD Peak Positions for Form A of Compound 1

| Position [°2θ] | Intensity [%] |
| --- | --- |
| 29.9 | 42.03 |
| 33.2 | 4.02 |
| 34.1 | 8.13 |

FIG. 1 depicts an XRPD pattern of Form A of compound 1.

Figure 2:
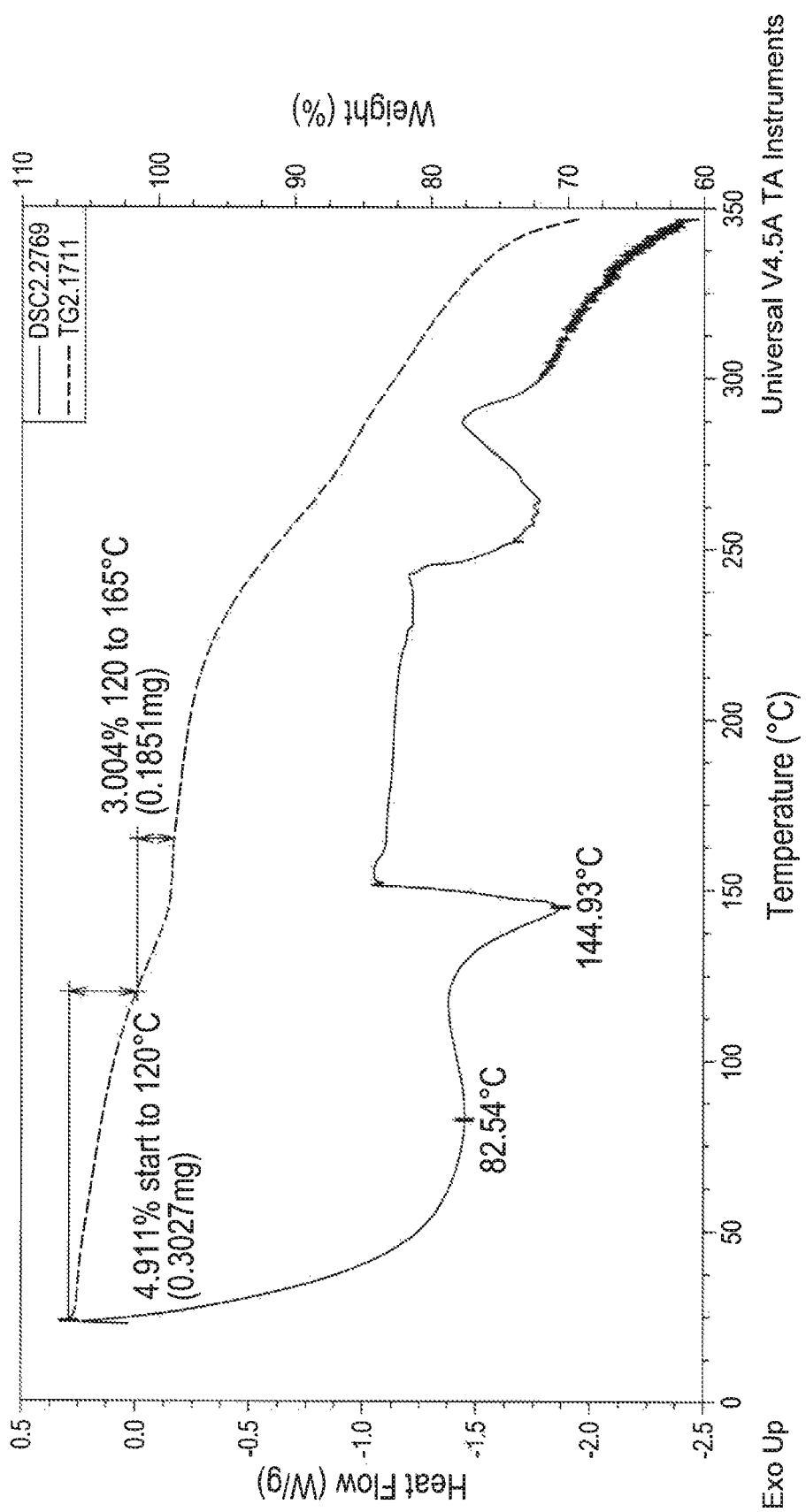
FIG. 2 depicts a TG/DSC trace of Compound 1, Form A.

FIG. 2 depicts a TG/DSC trace of Form A of compound 1.

Example 2-Preparation of Form A of Compound 2

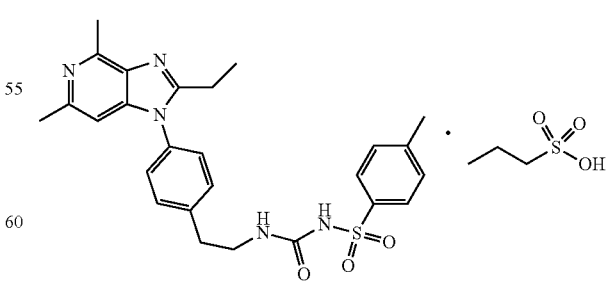

2

Form A of Compound 2

Form A of compound 2 was prepared by slurrying compound A with ethanesulfonic acid in acetone for 7 days at RT. The molar ratio of compound A to ethanesulfonic acid was about 1:1. The resulting solid material was analyzed by XRPD, DSC, TG and NMR.

Table 2, supra, is reproduced below and sets forth the X-ray diffraction peaks observed for Form A of compound 2.

TABLE 2

XRPD Peak Positions for Form A of Compound 2

| Position [°2θ] | Intensity [%] |
|---|---|
| 7.0 | 25.33 |
| 7.7 | 1.4 |
| 9.8 | 2.85 |
| 10.1 | 8.06 |
| 10.6 | 33.26 |
| 13.9 | 25.89 |
| 14.3 | 7.97 |
| 14.9 | 1.44 |
| 15.4 | 13.75 |
| 15.6 | 12.5 |
| 16.1 | 12.27 |
| 17.1 | 6.92 |
| 17.7 | 12.48 |
| 18.7 | 28.32 |
| 19.0 | 2.48 |
| 19.4 | 100 |
| 19.7 | 7.42 |
| 20.3 | 3.79 |
| 20.6 | 16.86 |
| 21.2 | 10.92 |
| 22.0 | 5.4 |
| 22.4 | 44.45 |
| 22.6 | 19.97 |
| 22.9 | 22.43 |
| 23.4 | 6.39 |
| 23.6 | 8.31 |
| 23.8 | 14.16 |
| 24.4 | 1.95 |
| 25.8 | 21.26 |
| 26.3 | 0.5 |
| 26.5 | 6.39 |
| 26.7 | 5.16 |
| 27.1 | 4.54 |
| 27.3 | 9.29 |
| 27.6 | 6.69 |
| 27.8 | 3 |
| 28.0 | 2.21 |
| 28.5 | 4.18 |
| 28.8 | 1.88 |
| 29.2 | 4.7 |
| 29.4 | 2.06 |
| 30.6 | 4.12 |
| 31.0 | 2 |
| 31.1 | 0.88 |
| 31.4 | 1.02 |
| 31.9 | 3.47 |
| 32.6 | 2.62 |
| 33.3 | 1.68 |
| 33.5 | 0.61 |
| 33.8 | 0.5 |
| 34.4 | 0.63 |
| 35.1 | 1.09 |
| 35.8 | 2.84 |
| 36.4 | 0.7 |
| 36.6 | 2.1 |
| 36.8 | 4.7 |
| 37.6 | 3.53 |
| 37.8 | 0.69 |
| 39.1 | 0.83 |
| 39.4 | 0.45 |
| 39.5 | 0.54 |

FIG. 3 depicts an XRPD pattern of Form A of compound 2.

Figure 4:
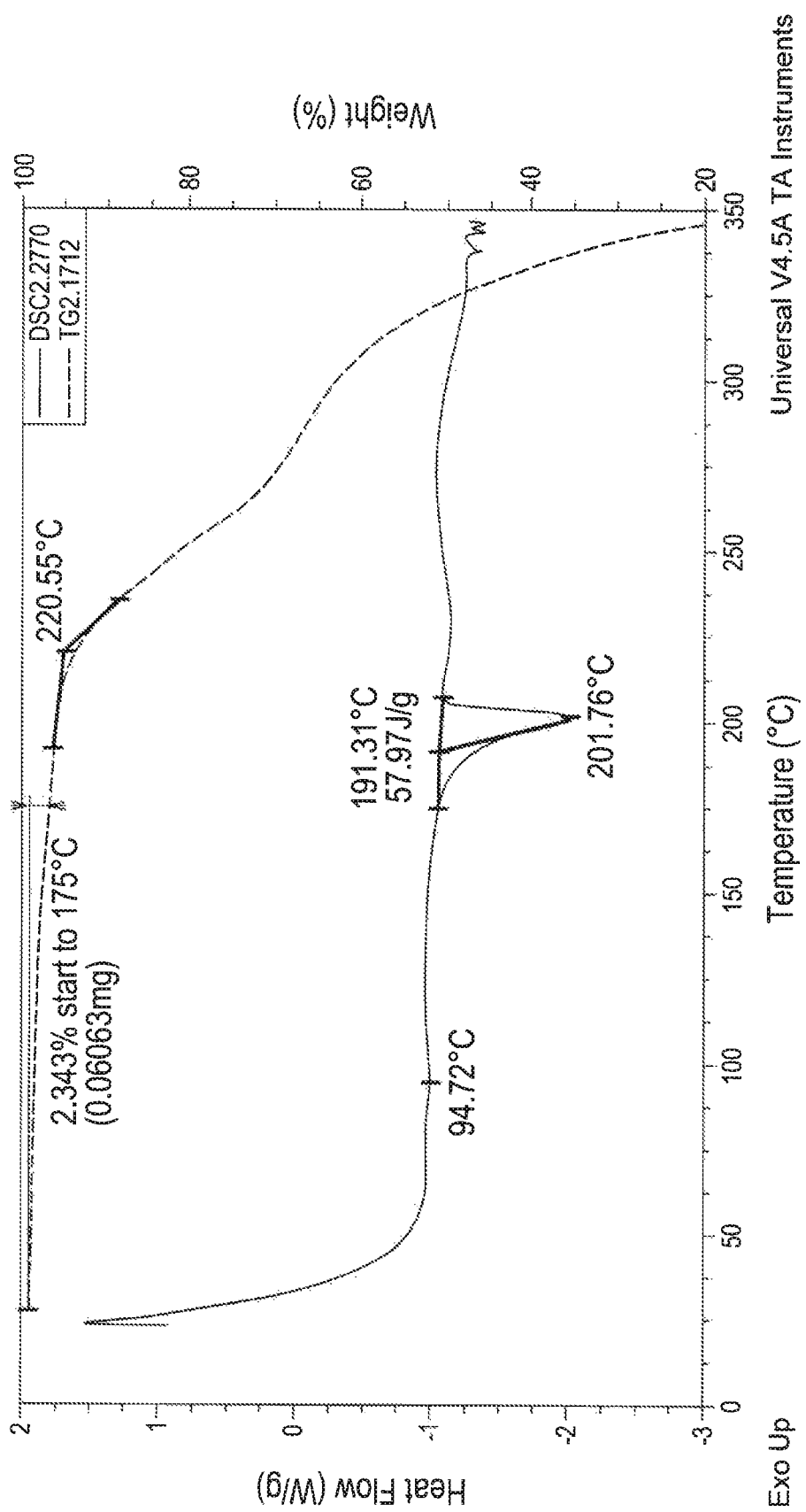
FIG. 4 depicts a TG/DSC trace of Compound 2, Form A.

FIG. 4 depicts a TG/DSC trace of Form A of compound 2.

Example 3-Preparation of Form A of Compound 3

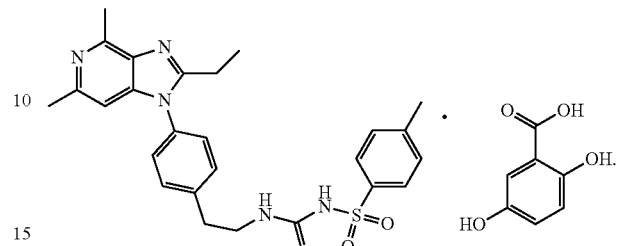

Form A of Compound 3

Form A of compound 3 was prepared by evaporating a solution of compound A and gentisic acid in methanol at RT. The molar ratio of compound A to gentisic acid was about 1:1. The resulting solid material was analyzed by XRPD, DSC, TG and NMR.

Table 3, supra, is reproduced below and sets forth the X-ray diffraction peaks observed for Form A of compound 3.

TABLE 3

XRPD Peak Positions for Form A of Compound 3

| Position [°2θ] | Intensity [%] |
|---|---|
| 8.2 | 64.33 |
| 9.5 | 100 |
| 9.9 | 20.01 |
| 12.4 | 34.52 |
| 13.0 | 25.53 |
| 15.0 | 2.18 |
| 15.4 | 8.24 |
| 15.7 | 21.79 |
| 16.2 | 2.41 |
| 16.9 | 17.35 |
| 17.1 | 7.65 |
| 17.4 | 9.75 |
| 18.5 | 21.22 |
| 19.0 | 2.17 |
| 20.3 | 9.43 |
| 20.6 | 18.62 |
| 21.7 | 8.26 |
| 22.8 | 26.07 |
| 23.2 | 16.5 |
| 23.6 | 17.27 |
| 24.8 | 11.08 |
| 25.0 | 6.16 |
| 25.2 | 2.9 |
| 25.8 | 24.55 |
| 26.4 | 5.5 |
| 27.4 | 2.95 |
| 27.6 | 4.51 |
| 27.8 | 1.5 |
| 29.0 | 15.21 |
| 29.2 | 5.54 |
| 30.2 | 2.86 |
| 30.7 | 3.56 |
| 31.7 | 3.3 |
| 32.1 | 2.77 |
| 32.4 | 2.42 |
| 32.9 | 4.46 |
| 33.2 | 5.34 |
| 33.8 | 1.01 |
| 34.4 | 0.79 |
| 36.0 | 2.24 |

TABLE 3-continued

| XRPD Peak Positions for Form A of Compound 3 | |
|---|---|
| Position [°2θ] | Intensity [%] |
| 36.5 | 0.93 |
| 37.3 | 0.58 |
| 37.6 | 0.74 |
| 39.0 | 2.68 |

FIG. 5 depicts an XRPD pattern of Form A of compound 3.

Figure 6:
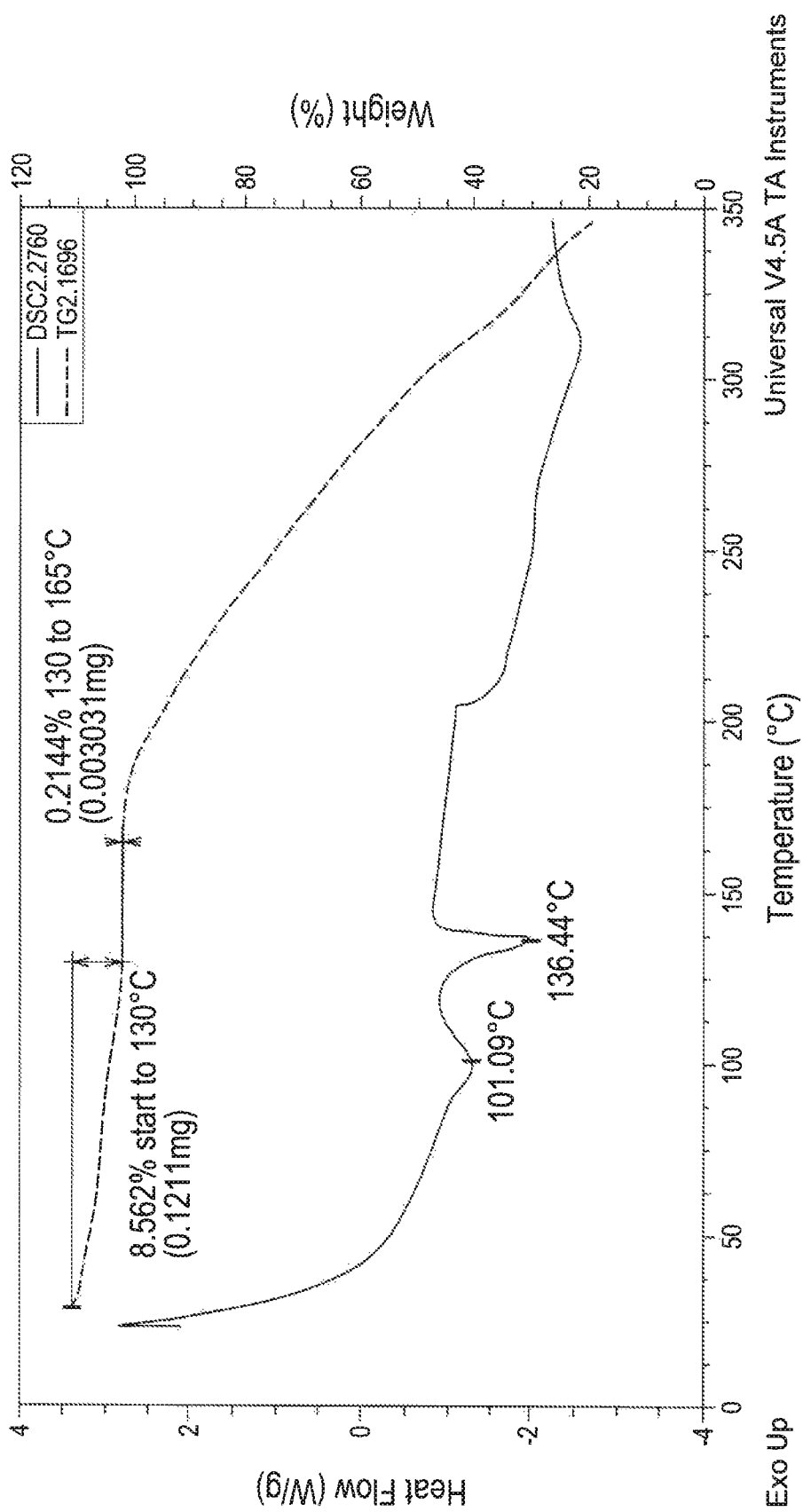
FIG. 6 depicts a TG/DSC trace of Compound 3, Form A.

FIG. 6 depicts a TG/DSC trace of Form A of compound 3.

Example 4-Preparation of Form A of Compound 4

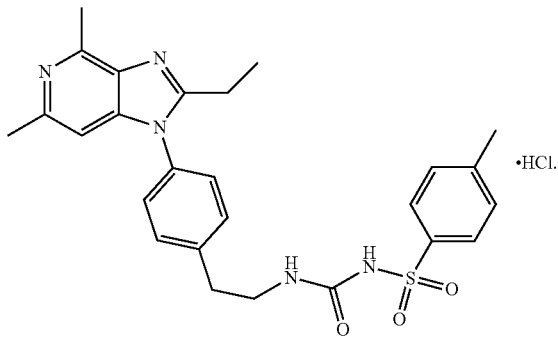

4

Form A of Compound 4

Form A of compound 4 was prepared by slurrying compound A with hydrochloric acid in acetone for 7 days at RT. The molar ratio of compound A to hydrochloric acid was about 1:1. The resulting solid material was analyzed by XRPD, DSC, TG and NMR.

Table 4, supra, is reproduced below and sets forth the X-ray diffraction peaks observed for Form A of compound 4.

TABLE 4

| XRPD Peak Positions for Form A of Compound 4 | |
|---|---|
| Position [°2θ] | Intensity [%] |
| 7.2 | 5.47 |
| 9.4 | 14.04 |
| 10.5 | 3.06 |
| 10.8 | 5.09 |
| 11.7 | 19.4 |
| 12.2 | 2.52 |
| 13.2 | 39.12 |
| 14.3 | 13.74 |
| 14.9 | 75.47 |
| 15.0 | 10.98 |
| 15.4 | 4.1 |
| 15.9 | 3.33 |
| 16.1 | 62.43 |
| 16.8 | 69.56 |
| 17.4 | 0.71 |
| 17.7 | 0.71 |
| 18.7 | 21.13 |
| 18.8 | 12.61 |

TABLE 4-continued

| XRPD Peak Positions for Form A of Compound 4 | |
|---|---|
| Position [°2θ] | Intensity [%] |
| 19.3 | 1.29 |
| 19.6 | 4.15 |
| 20.4 | 2.34 |
| 21.1 | 6.39 |
| 21.5 | 39.57 |
| 21.7 | 46.52 |
| 22.1 | 20.67 |
| 22.7 | 10.05 |
| 22.7 | 14.69 |
| 23.1 | 11.29 |
| 23.4 | 13.77 |
| 23.5 | 18.22 |
| 23.7 | 33.49 |
| 24.0 | 6.21 |
| 24.2 | 18.86 |
| 24.5 | 100 |
| 25.2 | 7.38 |
| 25.8 | 6.2 |
| 26.1 | 15.98 |
| 26.3 | 7.76 |
| 26.5 | 2.8 |
| 27.1 | 4.13 |
| 27.2 | 4.66 |
| 27.5 | 5.44 |
| 28.7 | 54.32 |
| 29.0 | 37.48 |
| 29.5 | 2.79 |
| 29.8 | 1.24 |
| 30.2 | 3.8 |
| 30.6 | 1.44 |
| 31.0 | 4.32 |
| 31.5 | 9.48 |
| 31.7 | 7.69 |
| 32.0 | 3.05 |
| 32.3 | 11.21 |
| 32.5 | 15.93 |
| 32.9 | 2.31 |
| 33.7 | 0.83 |
| 34.0 | 1.63 |
| 34.4 | 3.62 |
| 34.8 | 0.58 |
| 35.0 | 2.54 |
| 35.6 | 8.89 |
| 36.2 | 1.61 |
| 36.7 | 7.12 |
| 37.2 | 2.36 |
| 38.2 | 3.13 |
| 38.6 | 3.02 |
| 39.0 | 0.44 |
| 39.7 | 3.2 |
| 39.9 | 4.42 |

FIG. 7 depicts an XRPD pattern of Form A of compound 4.

Figure 8:
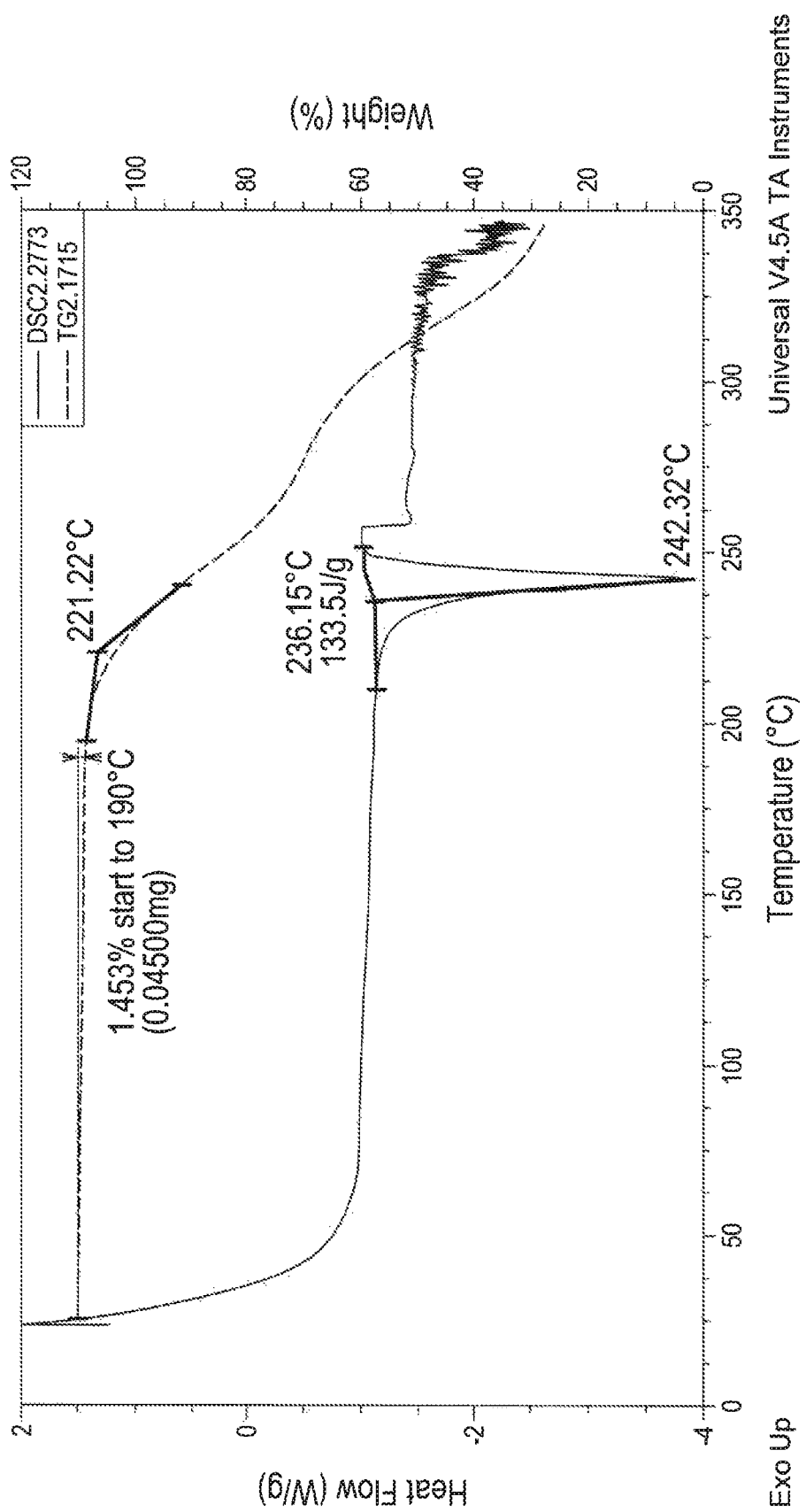
FIG. 8 depicts a TG/DSC trace of Compound 4, Form A.

FIG. 8 depicts a TG/DSC trace of Form A of compound 4.

Example 5-Preparation of Form A of Compound 5

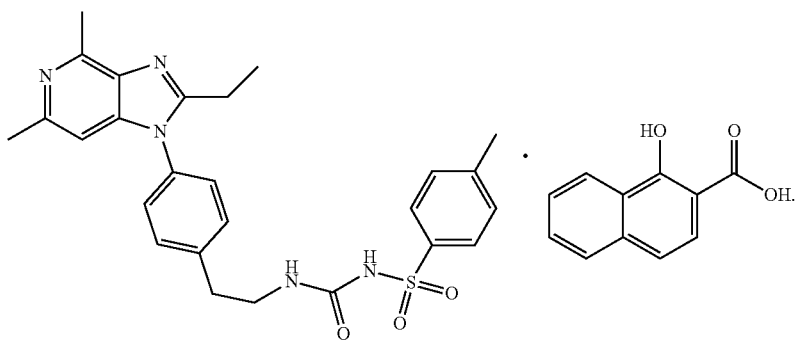

Form A of Compound 5

Form A of compound 5 was prepared by slurrying compound A with xinafoic acid in acetone for 7 days at RT. The molar ratio of compound A to xinafoic acid was about 1:1. The resulting solid material was analyzed by XRPD, DSC, TG and NMR.

Table 5, supra, is reproduced below and sets forth the X-ray diffraction peaks observed for Form A of compound 5.

TABLE 5

XRPD Peak Positions for Form A of Compound 5

| Position [°2θ] | Intensity [%] |
|---|---|
| 4.9 | 87.88 |
| 6.7 | 18.75 |
| 7.9 | 3.1 |
| 9.6 | 67.51 |
| 9.8 | 47.62 |
| 11.5 | 12.07 |
| 12.5 | 47.05 |
| 12.7 | 17.56 |
| 13.1 | 20.27 |
| 13.7 | 75.13 |
| 14.4 | 4.76 |
| 15.8 | 82.58 |
| 16.7 | 18.58 |
| 17.5 | 10.62 |
| 19.2 | 13.14 |
| 19.4 | 4.42 |
| 20.4 | 18.65 |
| 20.8 | 6.18 |
| 21.1 | 30.79 |
| 22.8 | 4.56 |
| 23.1 | 23.23 |
| 24.8 | 35.06 |
| 25.2 | 100 |
| 25.4 | 3.48 |
| 26.0 | 33.08 |
| 26.4 | 13.82 |
| 27.1 | 2.04 |
| 27.8 | 4.15 |
| 29.7 | 9.74 |
| 30.5 | 1.96 |
| 30.0 | 3.94 |
| 31.9 | 2.89 |
| 33.0 | 7.92 |
| 34.2 | 2.1 |
| 37.4 | 1.82 |
| 38.7 | 2.4 |
| 39.4 | 2.46 |

FIG. 9 depicts an XRPD pattern of Form A of compound 5.

Figure 10:
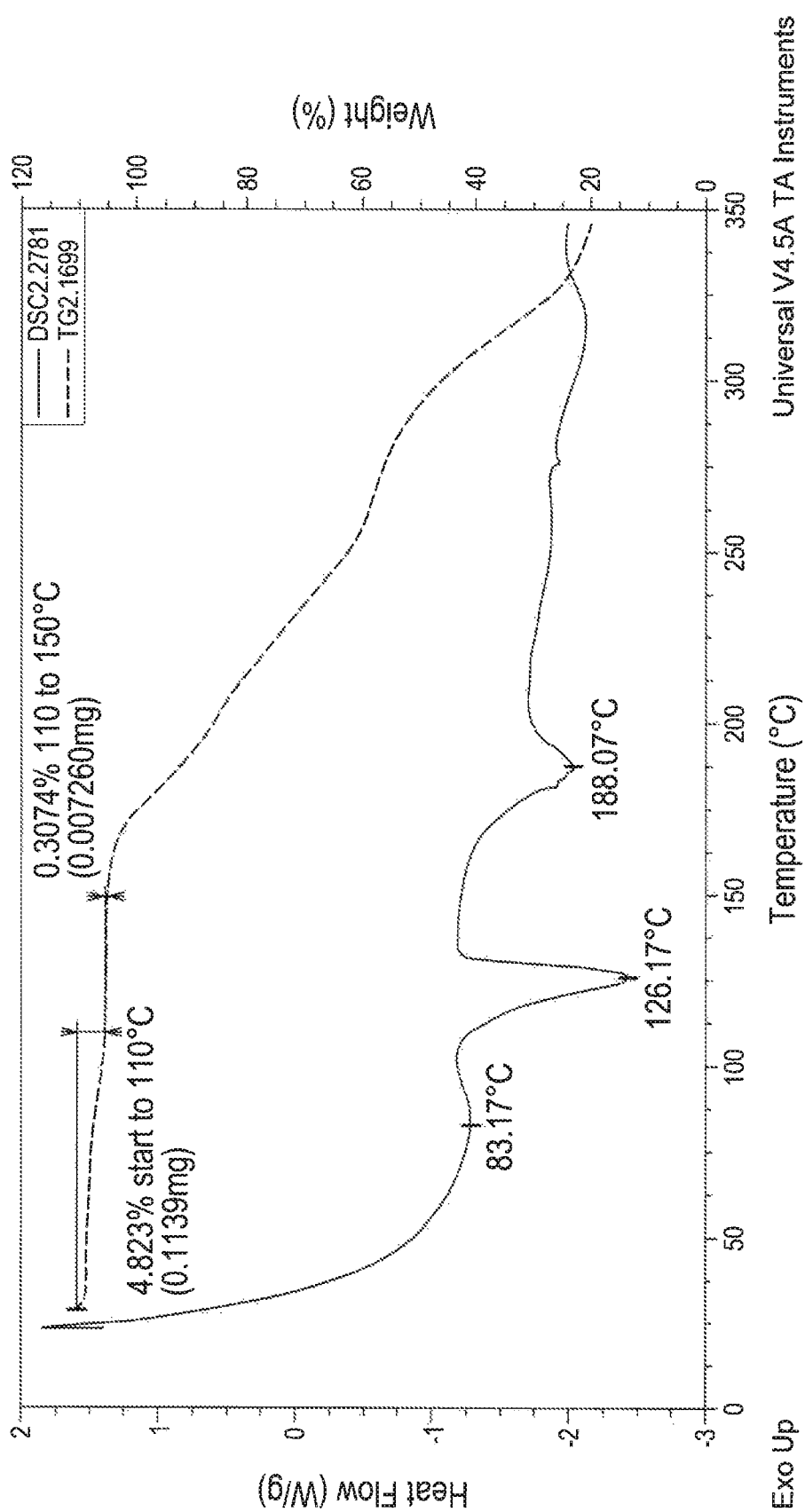
FIG. 10 depicts a TG/DSC trace of Compound 5, Form A.

FIG. 10 depicts a TG/DSC trace of Form A of compound 5.

Example 6-Preparation of Form A of Compound 6

Form A of Compound 6

Form A of compound 6 was prepared by slurrying compound A with isethionic acid in acetone for 7 days at RT. The molar ratio of compound A to isethionic acid was about 1:1. The resulting solid material was analyzed by XRPD, DSC, TG and NMR.

Table 6, supra, is reproduced below and sets forth the X-ray diffraction peaks observed for Form A of compound 6.

TABLE 6

XRPD Peak Positions for Form A of Compound 6

| Position [°2θ] | Intensity [%] |
|---|---|
| 5.8 | 99.63 |
| 7.0 | 12.91 |
| 7.2 | 16.44 |
| 7.8 | 10.03 |
| 9.8 | 40.29 |
| 10.7 | 6.83 |
| 11.6 | 16.99 |
| 12.1 | 17.66 |
| 12.7 | 35.75 |
| 12.8 | 11.99 |
| 14.0 | 15.11 |
| 14.3 | 65.63 |
| 15.2 | 100 |
| 15.6 | 32.34 |

TABLE 6-continued

XRPD Peak Positions for Form A of Compound 6

| Position [°2θ] | Intensity [%] |
|---|---|
| 17.6 | 48.58 |
| 18.3 | 11.38 |
| 18.7 | 4.78 |
| 19.1 | 38.89 |
| 19.7 | 40.82 |
| 19.9 | 51.88 |
| 20.6 | 22.08 |
| 21.2 | 68.69 |
| 22.1 | 88.96 |
| 22.6 | 42.71 |
| 23.0 | 7.9 |
| 23.3 | 26.47 |
| 24.3 | 12.66 |
| 24.9 | 82.85 |
| 25.4 | 57.98 |
| 26.9 | 39.57 |
| 28.0 | 12.39 |
| 28.7 | 16.02 |
| 28.9 | 3.38 |
| 29.2 | 17.48 |
| 29.6 | 3.46 |
| 29.8 | 3 |
| 30.6 | 12.17 |
| 32.4 | 4.75 |
| 32.7 | 8.41 |
| 33.9 | 6.03 |
| 34.5 | 3.21 |
| 35.7 | 4.74 |
| 36.8 | 3.69 |

FIG. 11 depicts an XRPD pattern of Form A of compound 6.

Figure 12:
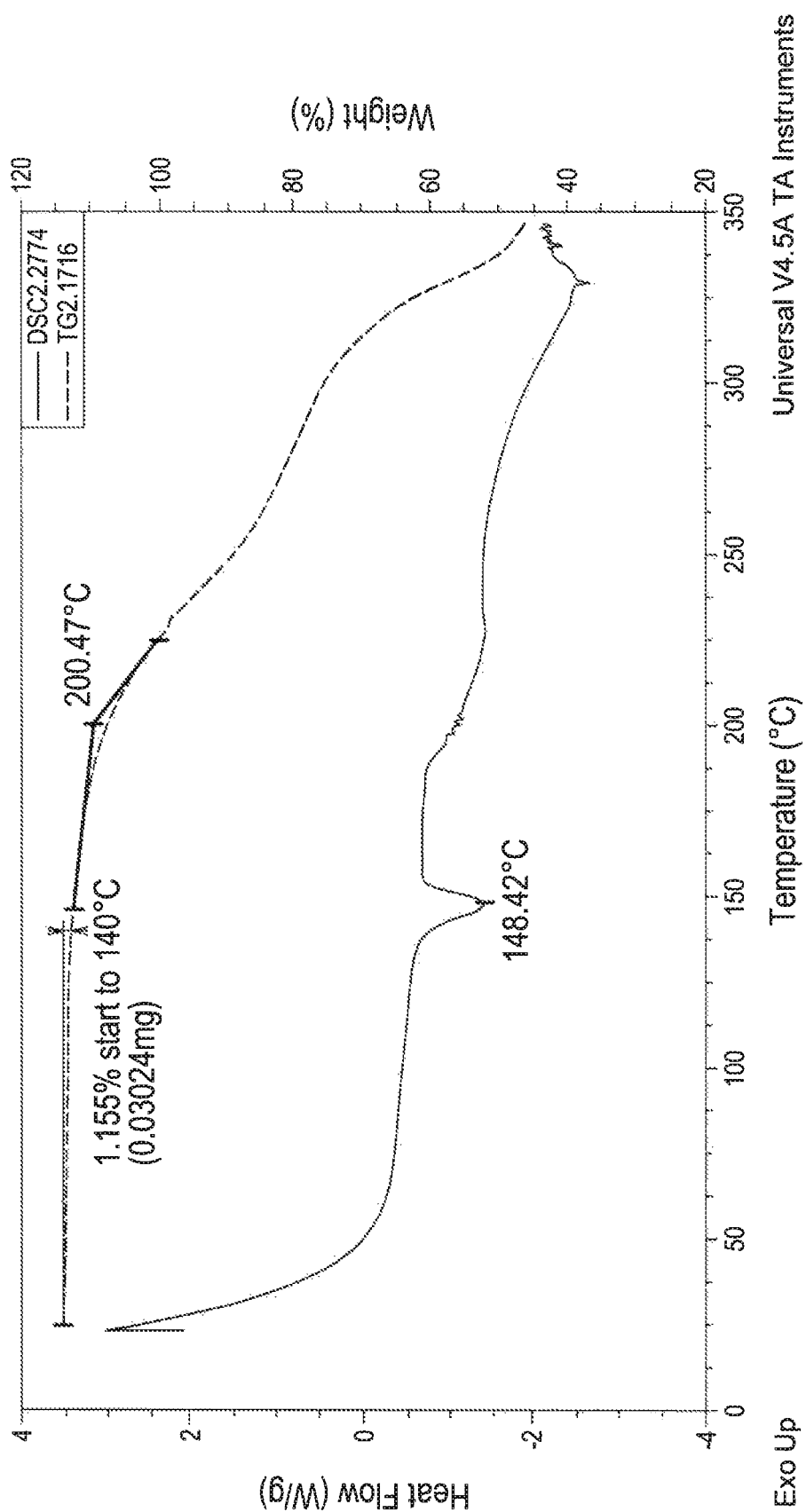
FIG. 12 depicts a TG/DSC trace of Compound 6, Form A.

FIG. 12 depicts a TG/DSC trace of Form A of compound 6.

Example 7-Preparation of Form A of Compound 7

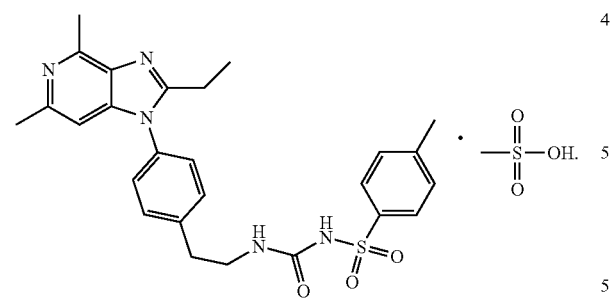

Form A of Compound 7

Form A of compound 7 was prepared by slurrying compound A with methanesulfonic acid in THF for 5 days at 40° C. The molar ratio of compound A to methanesulfonic acid was about 1:1. The resulting solid material was analyzed by XRPD, DSC, TG and NMR.

Table 7, supra, is reproduced below and sets forth the X-ray diffraction peaks observed for Form A of compound 7.

TABLE 7

XRPD Peak Positions for Form A of Compound 7

| Position [°2θ] | Intensity [%] |
|---|---|
| 7.0 | 33.31 |
| 7.8 | 7.24 |
| 10.1 | 8.16 |
| 10.7 | 36.62 |
| 14.0 | 37.89 |
| 14.5 | 5.87 |
| 15.6 | 42.54 |
| 16.4 | 15.77 |
| 16.7 | 1.17 |
| 17.4 | 17.97 |
| 17.6 | 1.16 |
| 17.8 | 11.14 |
| 18.6 | 22 |
| 19.1 | 100 |
| 19.6 | 14.84 |
| 19.7 | 11.11 |
| 20.3 | 4.16 |
| 20.6 | 8.33 |
| 20.8 | 1.07 |
| 21.1 | 1.85 |
| 21.5 | 10.49 |
| 221 | 20 |
| 22.5 | 73.06 |
| 22.8 | 21.05 |
| 23.1 | 10.01 |
| 23.5 | 14 |
| 23.7 | 16 |
| 25.0 | 4.63 |
| 26.0 | 5.61 |
| 26.1 | 16.41 |
| 26.7 | 15.55 |
| 27.1 | 8.71 |
| 27.5 | 3.04 |
| 28.0 | 11.91 |
| 28.4 | 7.99 |
| 29.5 | 8.34 |
| 30.7 | 5.69 |
| 31.3 | 2.68 |
| 31.9 | 3.32 |
| 32.0 | 2.89 |
| 32.5 | 3.53 |
| 32.9 | 4.83 |
| 33.7 | 0.87 |
| 36.6 | 7.2 |
| 37.2 | 2.62 |
| 37.6 | 4.83 |
| 39.1 | 1.38 |

FIG. 13 depicts an XRPD pattern of Form A of compound 7.

Figure 14:
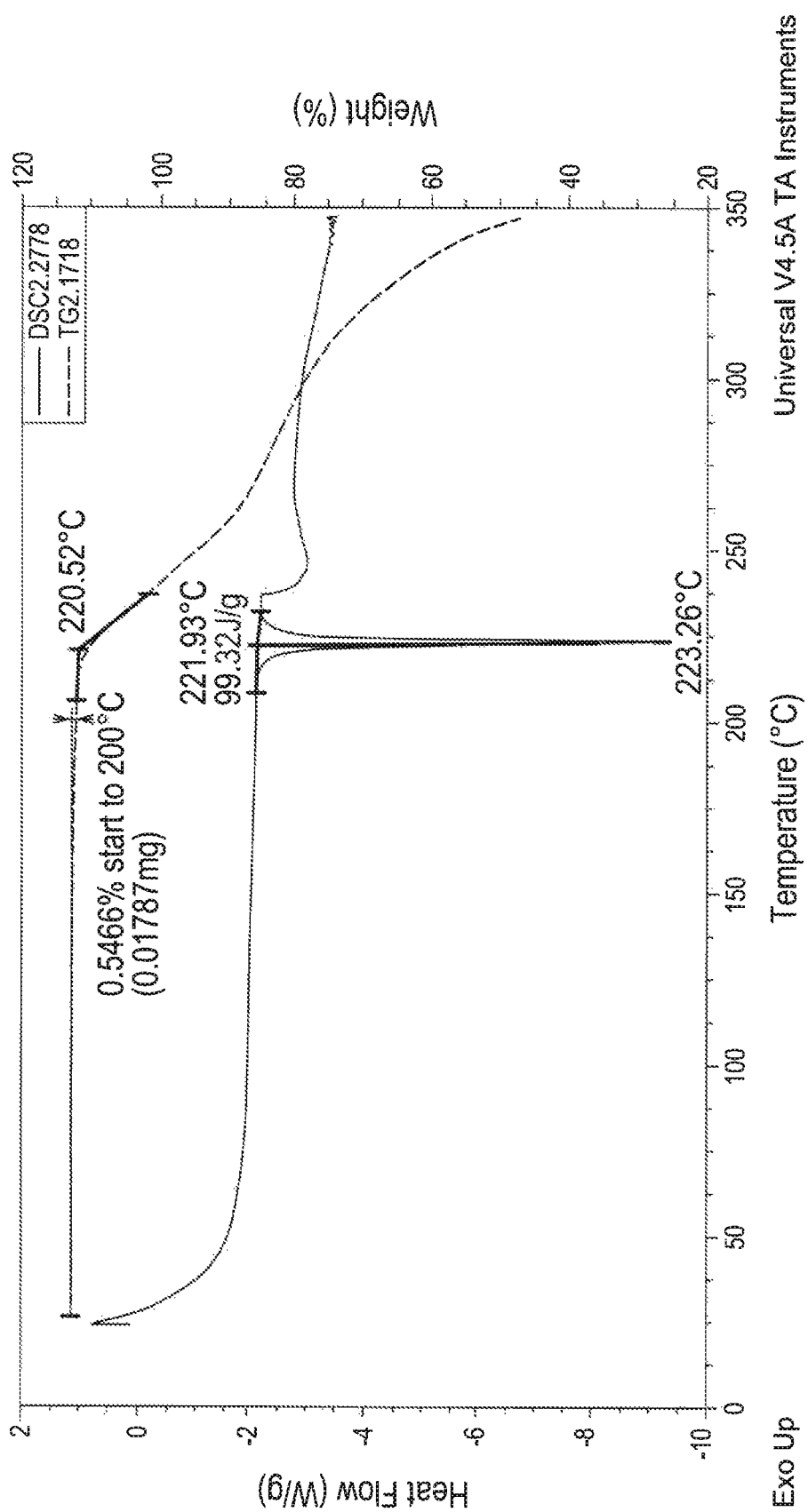
FIG. 14 depicts a TG/DSC trace of Compound 7, Form A.

FIG. 14 depicts a TG/DSC trace of Form A of compound 7.

Example 8-Preparation of Form A of Compound 8

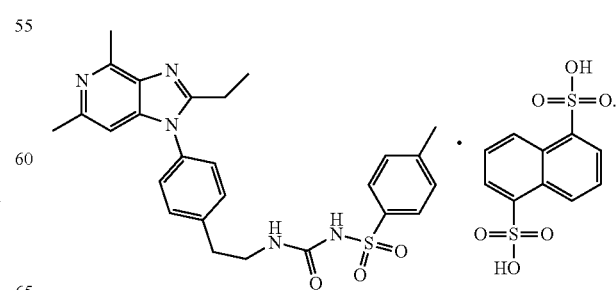

Form A of Compound 8

Form A of compound 8 was prepared by slurrying compound A with napthalene-1,5-disulfonic acid in THF for 5 days at 40° C. The molar ratio of compound A to napthalene-1,5-disulfonic acid was about 1:1. The resulting solid material was analyzed by XRPD, DSC, TG and NMR.

Table 8, supra, is reproduced below and sets forth the X-ray diffraction peaks observed for Form A of compound 8.

TABLE 8

XRPD Peak Positions for Form A of Compound 8

| Position [°2θ] | Intensity [%] |
| --- | --- |
| 6.3 | 5.71 |
| 6.8 | 52.76 |
| 7.5 | 6.57 |
| 9.9 | 4.1 |
| 10.7 | 29.64 |
| 11.0 | 47.27 |
| 12.1 | 9.42 |
| 12.8 | 16.63 |
| 13.5 | 93.6 |
| 14.0 | 87.33 |
| 16.1 | 15.56 |
| 17.4 | 2.9 |
| 17.7 | 9.64 |
| 18.4 | 38.49 |
| 18.8 | 4.14 |
| 19.1 | 2.75 |
| 20.0 | 16.92 |
| 20.4 | 45.39 |
| 20.9 | 7.25 |
| 21.7 | 100 |
| 22.6 | 12.99 |
| 22.9 | 2.82 |
| 23.6 | 19.17 |
| 24.2 | 45.45 |
| 25.1 | 32.36 |
| 26.6 | 34.47 |
| 27.5 | 12.55 |
| 28.1 | 4.61 |
| 29.2 | 9.81 |
| 29.9 | 27.75 |
| 30.4 | 13.37 |
| 33.8 | 3.17 |
| 34.8 | 3.29 |
| 36.8 | 17.43 |
| 38.7 | 2.36 |

FIG. 15 depicts an XRPD pattern of Form A of compound 8.

Figure 16:
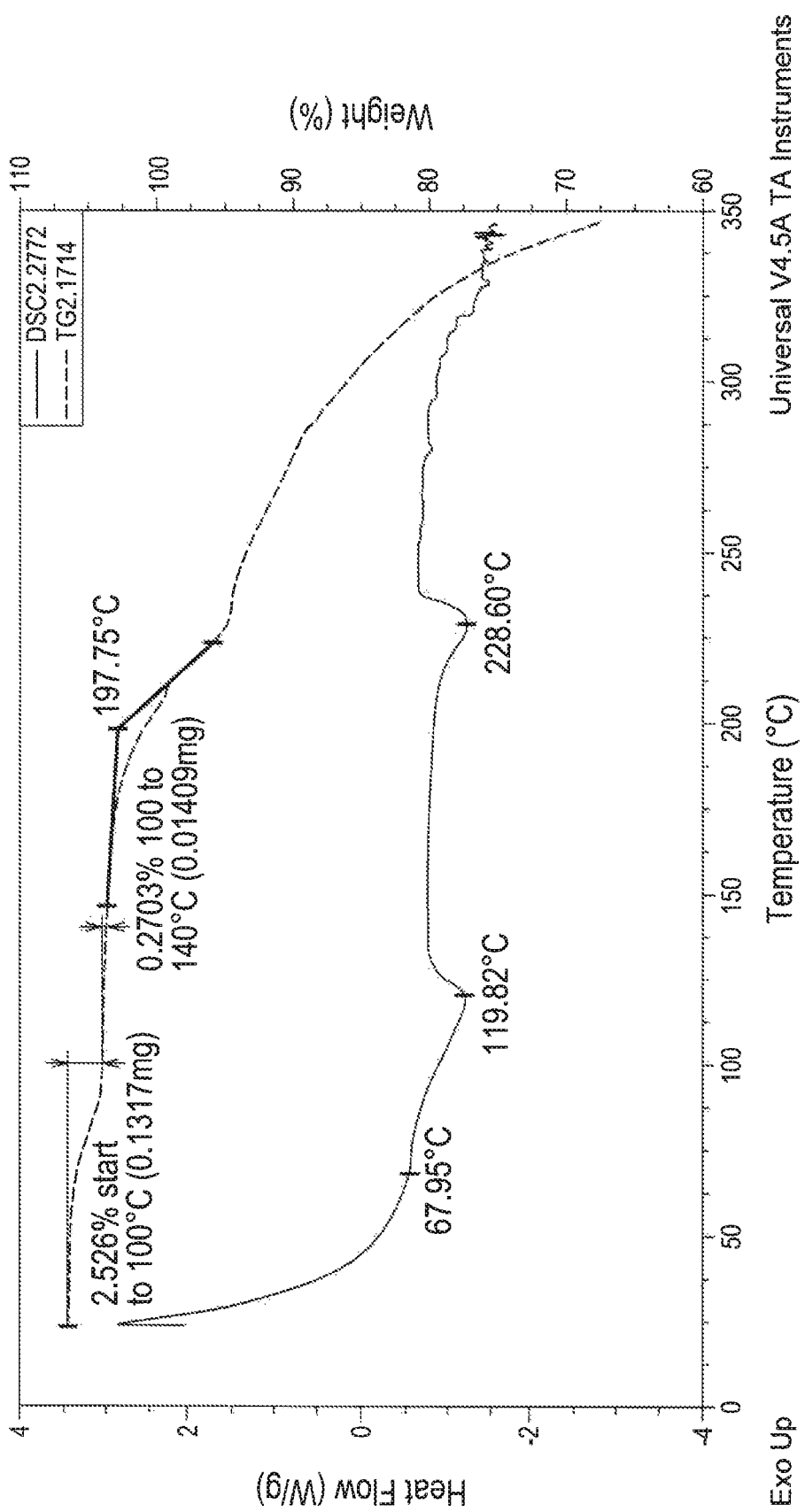
FIG. 16 depicts a TG/DSC trace of Compound 8, Form A.

FIG. 16 depicts a TG/DSC trace of Form A of compound 8.

Example 9-Preparation of Forms A and B of Compound 9

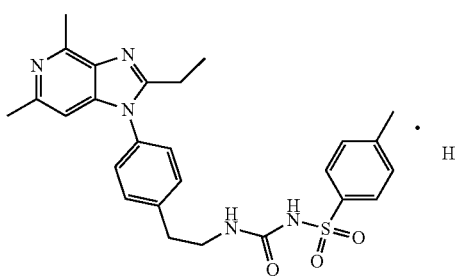

Form A of Compound 9

Form A of compound 9 was prepared by slurrying compound A with oxalic acid in acetone for 7 days at RT. The molar ratio of compound A to oxalic acid was about 1:1. The resulting solid material was analyzed by XRPD, DSC, TG and NMR.

Table 9, supra, is reproduced below and sets forth the X-ray diffraction peaks observed for Form A of compound 9.

TABLE 9

XRPD Peak Positions for Form A of Compound 9

| Position [°2θ] | Intensity [%] |
| --- | --- |
| 6.1 | 32.14 |
| 7.7 | 42.15 |
| 9.1 | 17.81 |
| 9.9 | 5.89 |
| 11.5 | 21.71 |
| 11.8 | 5.47 |
| 12.2 | 5.3 |
| 12.7 | 3.71 |
| 13.7 | 9.37 |
| 14.2 | 4.59 |
| 15.6 | 36.05 |
| 16.6 | 100 |
| 17.2 | 27.97 |
| 17.5 | 42.56 |
| 18.3 | 14.14 |
| 19.0 | 11.11 |
| 20.5 | 6.38 |
| 21.6 | 20.16 |
| 22.1 | 40.11 |
| 22.7 | 38.26 |
| 23.2 | 43.12 |
| 23.8 | 16.45 |
| 24.7 | 22.41 |
| 26.2 | 2.12 |
| 26.9 | 28.09 |
| 27.5 | 14.1 |
| 28.5 | 3.08 |
| 30.3 | 13.04 |
| 31.0 | 8.51 |
| 32.6 | 1.99 |

FIG. 17 depicts an XRPD pattern of Form A of compound 9.

Figure 18:
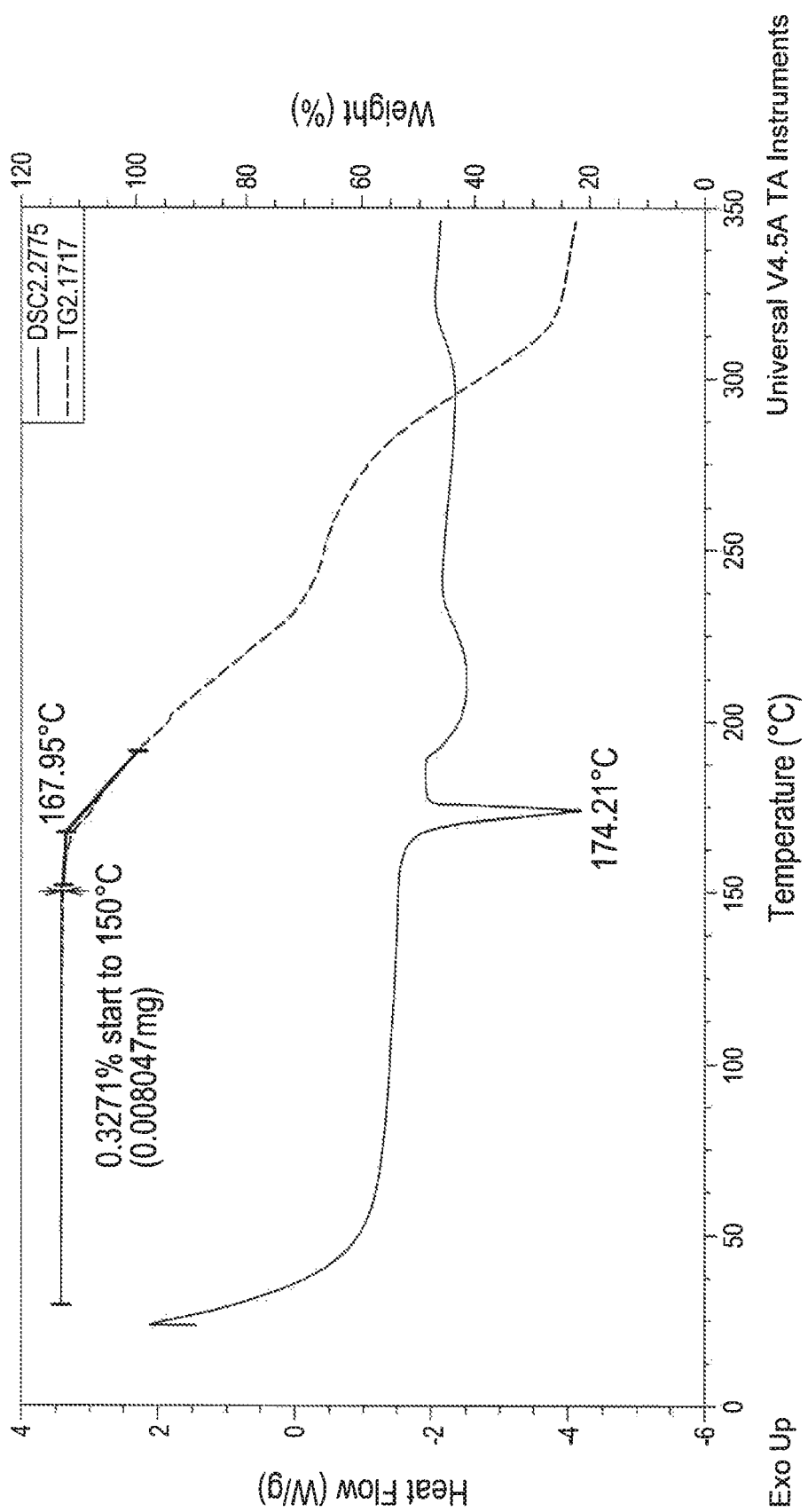
FIG. 18 depicts a TG/DSC trace of Compound 9, Form A.

FIG. 18 depicts a TG/DSC trace of Form A of compound 9.

Example 10-Preparation of Form A of Compound 10

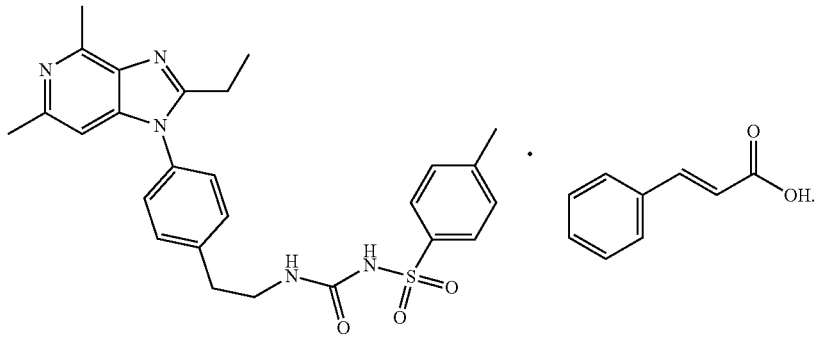

Form A of Compound 10

Form A of compound 10 was prepared by slurrying compound A with cinnamic acid in in ethanol at RT. The molar ratio of compound A to cinnamic acid was about 1:1. The resulting solid material was analyzed by XRPD, DSC, TG and NMR.

Table 10, supra, is reproduced below and sets forth the X-ray diffraction peaks observed for Form A of compound 10.

TABLE 10

XRPD Peak Positions for Form A of Compound 10

| Position [°2θ] | Intensity [%] |
|---|---|
| 4.8 | 33.13 |
| 5.7 | 3.96 |
| 6.7 | 4.03 |
| 7.9 | 9 |
| 9.6 | 78.7 |
| 11.5 | 29.66 |
| 12.6 | 11.29 |
| 12.8 | 27.51 |
| 13.5 | 18.67 |
| 13.6 | 28.47 |
| 14.3 | 46.33 |
| 15.1 | 87.8 |
| 15.7 | 100 |
| 15.9 | 16.89 |
| 17.0 | 8.46 |
| 17.5 | 9.36 |
| 18.3 | 12.81 |
| 19.2 | 18.88 |
| 20.3 | 18.64 |
| 20.7 | 9.31 |
| 21.2 | 64.74 |
| 21.6 | 8.8 |
| 22.5 | 15.25 |
| 23.0 | 9.48 |
| 23.9 | 6.18 |
| 24.9 | 15.92 |
| 25.4 | 24.53 |
| 25.8 | 51.55 |
| 26.1 | 57.05 |
| 26.6 | 5.58 |
| 27.1 | 22.2 |
| 27.3 | 36.9 |
| 27.7 | 4.35 |
| 28.2 | 4.7 |
| 28.9 | 12.06 |
| 29.5 | 6.85 |
| 30.5 | 3.04 |
| 30.8 | 5.92 |

TABLE 10-continued

XRPD Peak Positions for Form A of Compound 10

| Position [°2θ] | Intensity [%] |
|---|---|
| 32.6 | 3.4 |
| 32.8 | 2.74 |
| 34.0 | 1.03 |
| 34.4 | 6.57 |
| 34.9 | 3.11 |
| 36.4 | 5.37 |

FIG. 19 depicts an XRPD pattern of Form A of compound 10.

Figure 20:
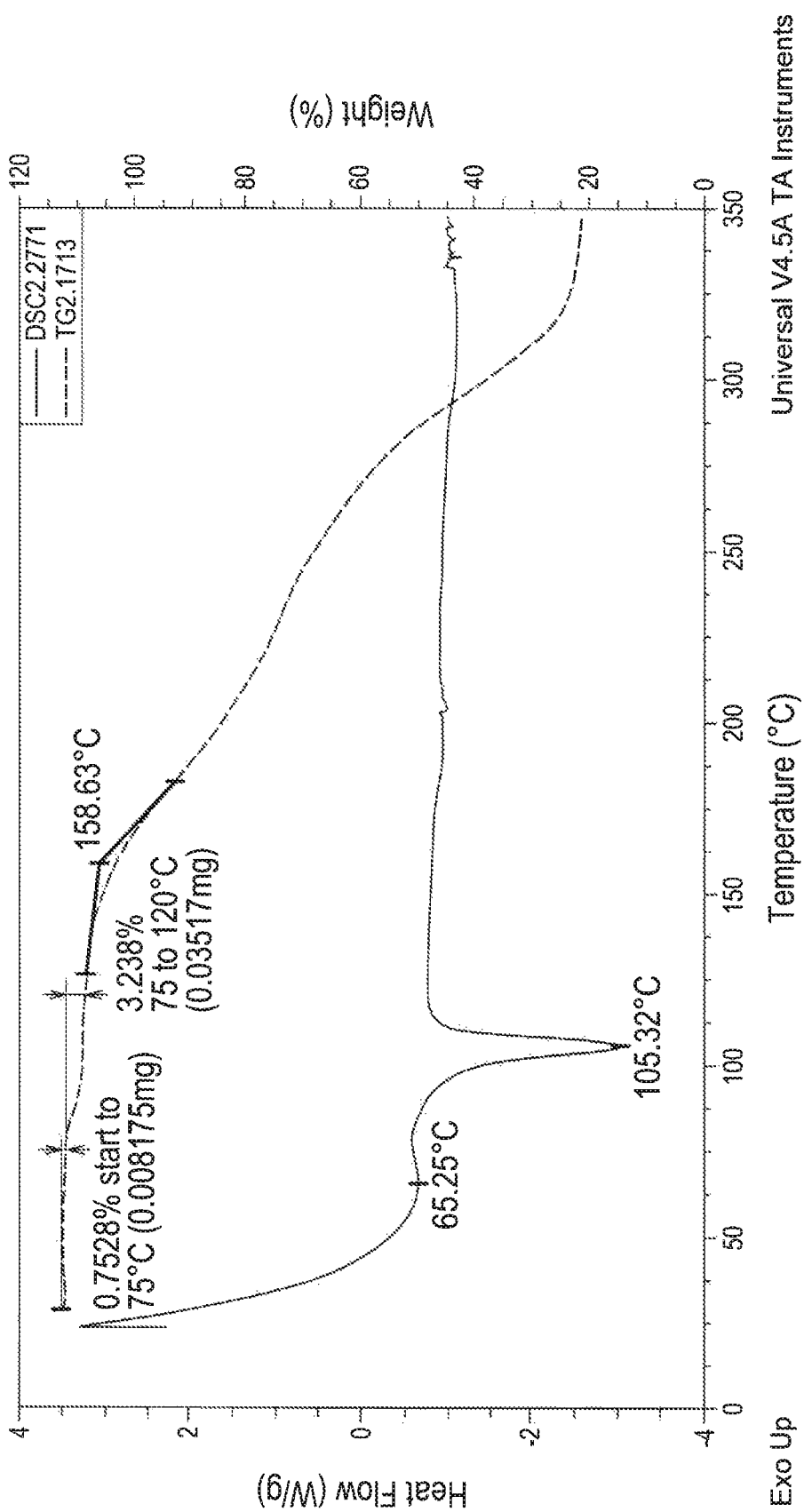
FIG. 20 depicts a TG/DSC trace of Compound 10, Form A.

FIG. 20 depicts a TG/DSC trace of Form A of compound 10.

Example 11-Preparation of Form A of Compound 11

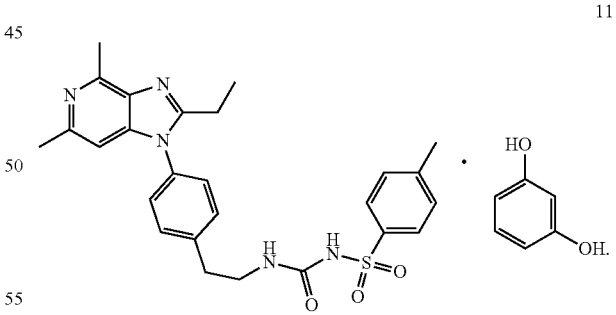

Form A of Compound 11

Form A of compound 11 was prepared by slurrying compound A with resorcinol in ethanol at RT. The molar ratio of compound A to resorcinol was about 1:1. The resulting solid material was analyzed by XRPD, DSC, TG and NMR.

Table 11, supra, is reproduced below and sets forth the X-ray diffraction peaks observed for Form A of compound 11.

TABLE 11

XRPD Peak Positions for Form A of Compound 11

| Position [°2θ] | Intensity [%] |
|---|---|
| 8.9 | 32.03 |
| 10.8 | 52.36 |
| 12.5 | 7.09 |
| 13.6 | 50.66 |
| 13.9 | 31.47 |
| 14.4 | 24.94 |
| 14.9 | 9.24 |
| 15.5 | 4.1 |
| 16.1 | 49.99 |
| 16.5 | 14.44 |
| 17.7 | 16.65 |
| 18.5 | 27.49 |
| 19.4 | 20.16 |
| 19.7 | 100 |
| 20.2 | 20.65 |
| 20.4 | 12.01 |
| 20.8 | 31.74 |
| 22.3 | 32.84 |
| 23.1 | 44.36 |
| 23.6 | 27.21 |
| 24.1 | 14.46 |
| 24.9 | 14.43 |
| 25.2 | 19.18 |
| 25.6 | 2.42 |
| 26.6 | 16.02 |
| 27.1 | 5.85 |
| 30.2 | 10.54 |
| 31.9 | 6.66 |

FIG. 21 depicts an XRPD pattern of Form A of compound 11.

Example 12. A Phase 1b/2 Study of Grapiprant, an EP4 Inhibitor, and Pembrolizumab, a PD-1 Checkpoint Inhibitor, in Patients with Advanced or Metastatic Post-PD-1/L1 Non-Small Cell Lung Cancer (NSCLC) Adenocarcinoma Overall Design: This study is a multi-center, open-label, single-arm, Phase1b/2 study to evaluate the safety and efficacy of grapiprant in combination with pembrolizumab in adult patients diagnosed with NSCLC who have been previously treated for a minimum of 12 weeks with any PD-1 or PD-L1 checkpoint inhibitor. Participant enrollment and continuous safety assessment will be dictated by an mTPI model. Decisions for dose escalation and de-escalation will be made by a safety review board (SRB) comprised of enrolling study investigators and the Sponsor. The starting grapiprant dose will be 300 mg twice a day (BID) unless lowered at the study initiation by the SRB. Dose escalation and confirmation will end after 14 participants have been treated at any of the selected doses found to be acceptable. Following the continuous safety assessment phase, additional participants up to a total trial size of 25 will be enrolled to assess efficacy. Participants, including those who achieve a complete response (CR), may receive treatment with grapiprant and pembrolizumab for up to 2 years or until they experience disease progression with clinical deterioration, unacceptable toxicity, or consent withdrawal, followed by 30- and 90-Day End of Treatment Follow-up visits after their last day of study treatment.

Participants will be treated with grapiprant and pembrolizumab on Cycle 1 Day 1.

PK samples will be taken as indicated on the Schedule of Events (SoE).

Scans for tumor assessment will be assessed for all participants every 8 weeks (+/−7 days) from treatment initiation for the first 3 cycles, and then every 12 weeks (+/−7 days) thereafter, and at the discretion of the investigator.

Participants will be instructed to maintain a normal diet during the Combination Treatment and will be encouraged to take grapiprant with food regularly as food is known to decrease common mild GI AEs in drugs of a similar class (COX-2 inhibitors). Morning food intake will be recorded in the medication administration diary on days when post-dose PK samples are drawn.

Mandatory tumor biopsies will be collected in a subset of up to 10 evaluable participants deemed safe for repeated biopsies before Cycle 1 Day 1 and between the end of Cycle 1 and end of Cycle 3, ideally from the same tumor. A third tumor biopsy will be collected in any participant in the biopsy subgroup who has a partial response on tumor assessment, within a month of RECIST v1.1 response documentation, if safe to access, and discussed with the Sponsor.

Main Inclusion Criteria:
1. Male and female adult patients (≥18 years of age on day of signing informed consent) with a histologically confirmed non-small cell lung cancer (NSCLC) adenocarcinoma.
2. Advanced (stage IIIb) disease that is not amenable to curative intent treatment with concurrent chemoradiation and metastatic (stage IV) patients. There is no limit to the number of prior treatment regimens.
3. Patients must have progressed clinically and/or radiographically per RECIST v1.1 after receiving a PD-1 or PD-L1 antagonist for a minimum of 12 weeks. Note: Immunotherapy may have been given with or without chemotherapy and may have been used in any line, however no more than one prior regimen of immunotherapy is allowed.
4. Have measurable disease per RECIST v1.1 as assessed by the local site investigator/radiology. Lesions situated in a previously irradiated area are considered measurable if progression has been demonstrated in such lesions.
5. For biopsy subgroup (10 participants), disease that can be safely accessed via bronchoscopic, thoracoscopic or percutaneous biopsy for multiple core biopsies (minimum of 3 passes per biopsy) and participant is willing to provide tissue from newly obtain biopsies on study.
6. Have an Eastern Cooperative Oncology Group (ECOG) performance status of 0 to 1.
7. Have adequate organ function as defined in Table A below.
8. Willing to use contraception for women who are not postmenopausal and all men.
9. Be willing and able to provide written informed consent for the trial.

TABLE A

Adequate Organ Function Laboratory Values

| System | Laboratory Value |
|---|---|
| Hematological | |
| ANC | ≥1500/μL |
| Platelets | ≥75,000/μL |
| Hemoglobin | ≥9.0 g/dL or ≥5.6 mmol/L[1] |
| Renal | |
| Creatinine OR | ≤1.5 × ULN OR |
| Measured or calculated[2] creatinine clearance in | ≥40 mL/min for participant with creatinine levels |

TABLE A-continued

Adequate Organ Function Laboratory Values

| System | Laboratory Value |
|---|---|
| mL/min (GFR can also be used in place of creatinine or CrCl) | >1.5 × institutional ULN |
| Hepatic | |
| Total bilirubin | ≤1.5 × ULN OR direct bilirubin ≤ULN for participants with total bilirubin levels >1.5 × ULN |
| AST (SGOT) and ALT (SGPT) | ≤2.5 × ULN (≤5 × ULN for participants with liver metastases) |
| Coagulation | |
| INR OR PT aPTT | ≤1.5 × ULN unless participant is receiving anticoagulant therapy as long as PT or aPTT is within therapeutic range of intended use of anticoagulants |

ALT (SGPT) = alanine aminotransferase (serum glutamic pyruvic transaminase);
ANC = absolute neutrophil count;
aPTT = activated partial thromboplastin time;
AST (SGOT) = aspartate aminotransferase (serum glutamic oxaloacetic transaminase);
CrCl = creatinine clearance;
GFR = glomerular filtration rate;
INR = international normalized ratio;
PT = prothrombin time;
ULN = upper limit of normal.
[1]Criteria must be met without erythropoietin dependency and without packed red blood cell (pRBC) transfusion within last 2 weeks.
[2]Creatinine clearance in ml/min should be estimated by Cockcroft-Gault formula.
Note:
This table includes eligibility-defining laboratory value requirements for treatment; laboratory value requirements should be adapted according to local regulations and guidelines for the administration of specific chemotherapies.

Main Exclusion Criteria:
1. Current use of NSAIDs (eg, ibuprophen, naproxen), COX-2 inhibitors (eg, celecoxib) within 3 days before treatment initiation or at any time during the study unless used for management of AE or otherwise authorized by the medical director. Aspirin products should be limited to prophylactic cardiovascular doses unless discussed with the Sponsor.
2. Any patient with a known epidermal growth factor receptor (EGFR), anaplastic lymphoma kinase (ALK), or ROS gene alteration.
3. Any patient with a known BRAF gene mutation.
4. Any patient without a history of smoking (≤100 cigarettes lifetime) should be discussed with the Sponsor before enrolling.
5. History of severe hypersensitivity reactions to a PD-1/L1 antibody.
6. Has received prior systemic anti-cancer therapy including investigational agents within 4 weeks prior to treatment. Note: Participants must have recovered from all AEs due to previous therapies to ≤Grade 1 or baseline. Participants with ≤Grade 2 neuropathy may be eligible after discussion with the Sponsor.
7. Has received prior radiotherapy within 2 weeks of start of study treatment. Participants must have recovered from all radiation-related toxicities, not require corticosteroids, and not have had radiation pneumonitis. A 1-week washout is permitted for palliative radiation (≤2 weeks of radiotherapy) to non-central nervous system (CNS) disease.
    Note: No other concurrent antineoplastic treatment is permitted on study except for allowed local radiation of lesions for palliation only (to be considered non-target lesions after treatment)
    Note: If participant received surgery, they must have recovered fully from the toxicity and/or complications from the intervention prior to starting study treatment.
8. Has received a live vaccine within 30 days prior to the first dose of study treatment.
9. Participants taking strong CYP3A4 or P-glycoprotein inhibitors or inducers are excluded from the study unless they can be transferred to other medications within ≥5 half-lives prior to dosing.
10. Is currently participating in or has participated in a study of an investigational agent or has used an investigational device within 4 weeks prior to the first dose of study treatment. Note: Participants who have entered the follow-up phase of an investigational study may participate as long as it has been 4 weeks after the last dose of the previous investigational agent.
11. Has a diagnosis of immunodeficiency or is receiving chronic systemic steroid therapy (in dosing exceeding 10 mg daily of prednisone equivalent) or any other form of immunosuppressive therapy within 7 days prior the first dose of study treatment.
12. Has a known additional potentially life-threatening malignancy that is progressing or has required active treatment within the past 3 years. Note: Participants with basal cell carcinoma of the skin, squamous cell carcinoma of the skin, or carcinoma in situ (eg, breast carcinoma, cervical cancer in situ) that have undergone potentially curative therapy are not excluded.
13. Has known active CNS metastases and/or carcinomatous meningitis (clinically stable and/or previously treated inactive CNS metastases allowed).
14. Has an active autoimmune disease that has required systemic treatment in past 2 years (ie, with use of disease modifying agents, corticosteroids or immunosuppressive drugs). Replacement therapy (eg, thyroxine, insulin, or physiologic corticosteroid replacement therapy for adrenal or pituitary insufficiency) is not considered a form of systemic treatment and is allowed. Autoimmune diseases include but are not limited to inflammatory bowel disease (IBD) such as Crohn's disease and ulcerative colitis.
15. Has a history of (non-infectious) pneumonitis that required steroids or has current pneumonitis.
16. Has an active infection requiring systemic therapy.
17. Recent (within the last 12 months) or current GI ulcer or colitis or non-immune colitis.
18. Has a known history of human immunodeficiency virus (HIV) infection.
19. Has a known history of Hepatitis B or known active Hepatitis C virus infection.
20. Clinically significant (ie, active) cardiovascular disease: cerebral vascular accident/stroke (<6 months prior to enrollment), myocardial infarction (<6 months prior to enrollment), unstable angina, congestive heart failure (≥New York Heart Association Classification Class II), or uncontrolled cardiac arrhythmia.
21. Has a history or current evidence of any condition, therapy, or laboratory abnormality that might confound the results of the study, interfere with the participant's participation for the full duration of the study, or is not in the best interest of the participant to participate, in the opinion of the treating investigator.
22. Has known psychiatric or substance abuse disorders that would interfere with cooperating with the requirements of the study.
23. A woman of childbearing potential (WOCBP) who has a positive pregnancy test prior to treatment.
24. Is breastfeeding or expecting to conceive or father children within the projected duration of the study.

Number of Participants:
   Approximately 30 patients from approximately 3 to 6 study centers in the United States will be screened to enroll 25 participants in this study. Enrollment is defined as the time of initiation of the first dose of study treatment.
   Participants who are withdrawn from treatment during the first cycle (ie, dose-limiting toxicity [DLT] period) for reasons other than AEs will be replaced Intervention Groups and Duration:
   A cycle of treatment will be defined as every 3 weeks (Q3W).
   Participants will receive the combination of grapiprant and pembrolizumab beginning on Cycle 1 Day 1.
   The dose of grapiprant will be 300 mg administered orally BID (daily dose taken at 8- to 12-hour intervals, preferably with food).
   The pembrolizumab dose will be 200 mg IV Q3W.
   Dose and schedule adjustments, corticosteroid administration, and monitoring plan are described in the protocol.
   Participants with a DLT within the first cycle will have their dose of both grapiprant and pembrolizumab held until amelioration of their toxicities and be reduced from their existing dose of grapiprant by either 50 mg BID or 100 mg BID unless discussed with the Sponsor.
   Participants who experience a first intolerable treatment-emergent adverse event (TEAE) after the first cycle will have their dose of grapiprant and pembrolizumab held until amelioration of their toxicities and be reduced from their existing grapiprant dose by 50 mg BID increments. Switching grapiprant administration to a 2 week on/1 week off schedule is also to be considered by the investigator depending on the nature of the TEAE.
   Any participant who requires a decrease in the grapiprant dose below 150 mg BID will have grapiprant treatment discontinued, but may continue to receive pembrolizumab if clinical benefit has been demonstrated.
   Participants with Grade 2 or greater dyspepsia for 5 or more days may, at the judgment of the investigator, institute ranitidine at 75 mg orally BID, to be taken 2 hours after the dose of grapiprant, until symptoms abate.
   Additional dose adjustment and monitoring plan is described in the protocol.
   Participants, including those who achieve a CR, may receive grapiprant and pembrolizumab until they experience disease progression with clinical deterioration, unacceptable toxicity, or consent withdrawal, followed by 30- and 90-Day End of Treatment Follow-up visits after their last day of study treatment.
   The duration of the study for each participant will include a Screening period for inclusion in the study of up to 28 days, courses of Combination Treatment cycles repeated every 21 days for a maximum of 35 cycles (up to 2 years), and End of Treatment Follow-up visits at 30 and 90 days following the last day of study treatment administration. The End of Treatment 90-Day Follow-up visit will be considered as the End of Study visit.
   Dose de-escalation for all participants will take place any time safety rules indicate (eg, if 4 participants or more participants out of the first 6 participants experiences a DLT). Participants already enrolled and receiving drug without severe AEs may be permitted to receive additional doses at the original dose level after discussion with the Sponsor.
   The expected enrollment period is 15 months. The study cut-off date is defined as the date when all the participants have either completed 16 weeks of treatment (ie, until the second tumor assessment) or discontinued the study treatment. The participants who continue to receive the study treatment after the study cut-off date will be followed and appropriate statistical analysis (listings or updated tables for safety, drug exposure and activity) will be performed when all the participants have discontinued the study treatment.

Statistical Considerations:
   Determination of the sample size: The combination side-effect profile is expected to be similar to pembrolizumab alone.
   The recommend sample size for the mTPI design is $n=k*(d+1)$ (Ji and Wang, J Clin Oncol. 2013; 31 (14): 1785-91). If 8 subjects are dosed per dose level (k=8) and there are 2 doses tested (d=2), then it is anticipated that 24 subjects will be required. If 1 dose is tested, then it is anticipated that n=16 subjects will be needed. Dose escalation and confirmation will end after 14 participants have been treated at any of the selected doses found to be acceptable. Following the continuous safety assessment phase, additional subjects up to a total trial size of 25 will be assessed to establish an estimate of efficacy. There is no formal hypothesis testing or adjustment for multiplicity.
   General statistical approach: Descriptive analysis of safety parameters will be performed on the whole treated population, defined as all participants exposed to at least one dose of grapiprant. Type, frequency, seriousness and relatedness of TEAEs will be analyzed according to Medical Dictionary for Regulatory Activities (MedDRA). Laboratory abnormalities will be analyzed according to National Cancer Institute Common Terminology Criteria for Adverse Events (NCI-CTCAE v5.0).
   Pharmacokinetic Analyses: PK parameters of grapiprant will be summarized using descriptive statistics by dose level and time since last dose. The plasma PK of grapiprant will be described for the Cmax and AUC PK parameters. Any additional PK analyses will be described in the statistical analysis plan (SAP).
   Population PK and Exposure-Response Analyses: Data from this study will be included with data collected from previous studies in a population PK analysis. The influence of covariates (eg, body weight, age, sex, race, and concomitant medications) on PK parameters will be investigated, if necessary and appropriate.
   Additional exploratory PK and/or exposure-response modeling may be applied to the data, as appropriate.
   Results of PK and/or any population PK or exposure-response analyses may be reported outside the clinical study report.
   Efficacy analysis: Anti-tumor efficacy data will be descriptively presented on the evaluable response population including participants who had a disease assessment at screening and at a minimum one other time point during the study treatment.
   The following estimate and confidence intervals (CIs) are meant to provide an overview of the precision of the ORR estimate under several scenarios.
   If 1/25 subjects respond, the mean (95% CI) is 0.04 (0.0020, 0.1761).
   If 2/25 subjects respond, the mean (95% CI) is 0.08 (0.0144, 0.2310).
   If 3/25 subjects respond, the mean (95% CI) is 0.12 (0.0335, 0.2817).
   If 4/25 subjects respond, the mean (95% CI) is 0.16 (0.0566, 0.3296).
   If 5/25 subjects respond, the mean (95% CI) is 0.20 (0.0823, 0.3754).

If 8/25 subjects respond, the mean (95% CI) is 0.32 (0.1703, 0.5036)

Example 13. A Phase 1b Study of Grapiprant, an EP4 Inhibitor, and Pembrolizumab, a PD-1 Checkpoint Inhibitor in Patients with Advanced or Progressive Microsatellite Stable (MSS) Colorectal Cancer (CRC)

Overall Design: The study is a multi-center, open-label, single-arm, Phase 1b, safety, and efficacy study of grapiprant in combination with pembrolizumab in adult patients with advanced or progressive MSS CRC. This is the first study combining grapiprant with a PD-1 antibody (pembrolizumab), therefore, participant enrollment and continuous safety assessment will be dictated by an mTPI model. The Combination Treatment period will consist of 35 cycles (up to 2 years). The study also includes a one-week Single Agent Run-in period for the purpose of assessing pharmacodynamics of grapiprant as a single agent, as well as in combination with pembrolizumab in the following Combination Treatment period. Participants enrolled into Cohort 1 will be treated with grapiprant during the Single Agent Run-in period and all participants enrolled into Cohort 1 and Cohort 2 will receive treatment with grapiprant and pembrolizumab during the Combination Treatment period. Approximately 30 patients are planned to be screened for this study to allow up to 15 participants for enrollment into Cohort 1 and up to 10 participants for enrollment into Cohort 2. Cohort 1 will enroll participants prior to enrollment of participants into Cohort 2. Following the continuous safety assessment phase, enrollment of additional participants, up to a total trial size of 25 participants, will be assessed to establish an estimate of efficacy.

Single Agent Run-in Period: Cohort 1
  Participants will be treated for 1 week with the pharmacologically active dose of grapiprant as a single agent. A starting dose of Grapiprant 300 mg will be administered orally twice a day (BID).
  Participants will be instructed to maintain a normal diet during the Single Agent Runin and will be encouraged to take grapiprant with food regularly as food is known to decrease common mild GI AEs in drugs of a similar class (COX-2 inhibitors).
  A mandatory pre-treatment tumor biopsy will be collected for participants who are deemed safe for repeated biopsies in Cohort 1 before the first dose of grapiprant on Day 1 and a mandatory post-treatment tumor biopsy will be obtained between Day 5 of the Single Agent Run-in period and pre-dose of pembrolizumab on Cycle 1 Day 1 of the Combination Treatment period, ideally from the same tumor.
  PK samples will be taken as indicated on the Schedule of Events (SoE).
Combination Treatment Period: Cohorts 1 and 2
  All participants in Cohorts 1 and 2 will be treated with a starting dose of grapiprant 300 mg administered orally BID unless a dose de-escalation occurs and a fixed dose of pembrolizumab administered 200 mg IV every 3 weeks (Q3W) beginning on Cycle 1 Day 1.
  PK samples will be taken as indicated on the SoE.
  For participants deemed safe for repeated biopsies in Cohort 2, a mandatory pretreatment tumor biopsy will be collected during screening prior to receiving the first dose of either agent on Cycle 1 Day 1 and a mandatory second tumor biopsy will be collected between the end of Cycle 1 and the end of Cycle 3, ideally from the same tumor. A third tumor biopsy will be collected for any participant who has a partial response (PR) on tumor assessment, within a month of Response Evaluation Criteria in Solid Tumors version 1.1 (RECIST v1.1) response documentation, unless a biopsy has already been obtained within a month of the response or otherwise discussed with the medical director.
  Scans for tumor assessment will be assessed for all participants (Cohorts 1 and 2) every 8 weeks (+/−7 days) from treatment initiation for the first 3 cycles, and then every 12 weeks (+/−7 days) thereafter, and at the discretion of the investigator.
  Participants will be instructed to maintain a normal diet during the Combination Treatment and will be encouraged to take grapiprant with food regularly as food is known to decrease common mild GI AEs in drugs of a similar class (COX-2 inhibitors). Morning food intake will be recorded in the medication administration diary on days when post-dose PK samples are drawn.

Main Inclusion Criteria:
  1. Male and female adult patients (≥18 years of age on day of signing informed consent) with a histologically confirmed advanced, metastatic, or progressive CRC that is MSS. Microsatellite stability is based on prior polymerase chain reaction (PCR), Next-Gen sequencing, or immunohistochemistry results per institutional standards.
  2. Patient has received at least two prior lines of therapy for advanced or metastatic CRC, at least one of which included fluorouracil. Adjuvant therapy will be counted as a line of therapy only if progression occurs within 6 months of its completion. There is no limit to the number of prior treatment regimens.
  3. Have measurable disease per RECIST v1.1 as assessed by the local site investigator/radiology. Lesions situated in a previously irradiated area are considered measurable if progression has been demonstrated in such lesions.
  4. Accessible tumor that can be safely accessed for multiple core biopsies and patient is willing to provide tissue from newly obtain biopsies before and during treatment.
  5. Have an Eastern Cooperative Oncology Group (ECOG) performance status of 0 to 1.
  6. Have adequate organ function as defined in Table A above.
  7. Be able to swallow and absorb oral tablets
  8. Willing to use contraception for women who are not postmenopausal and all men.
  9. Be willing and able to provide written informed consent for the trial.

Main Exclusion Criteria:
  1. Has received prior therapy with an anti-PD-1, anti-PD-L1, or anti-PD-L2 agent or with an agent directed to another stimulatory or co-inhibitory T-cell receptor (eg, CTLA-4, OX 40, CD137).
  2. Current use of NSAIDs (eg, ibuprophen, naproxen), COX-2 inhibitors (eg, celecoxib) within 3 days before treatment initiation or at any time during the study unless used for management of AE or otherwise authorized by the Sponsor. Aspirin products should be limited to prophylactic cardiovascular doses unless discussed with the Sponsor.
  3. History of severe hypersensitivity reactions to chimeric or humanized antibodies.
  4. Has received prior systemic anti-cancer therapy including investigational agents within 4 weeks prior to treatment, or 5 half-lives, whichever is shorter. Participants must have recovered from all AEs due to previous therapies to ≤Grade 1 or baseline. Participants with ≤Grade 2 neuropathy may be eligible after discussion with the Sponsor. If participant received major surgery, they must have fully recovered from the toxicity and/or complications from the intervention prior to starting study treatment.

5. Has received prior radiotherapy within 2 weeks of start of study treatment. Participants must have recovered from all radiation-related toxicities, not require corticosteroids, and not have had radiation pneumonitis. A 1-week washout is permitted for palliative radiation (≤2 weeks of radiotherapy) to non-central nervous system (CNS) disease. No other concurrent antineoplastic treatment is permitted on study except for allowed local radiation of lesions for palliation only (to be considered non-target lesions after treatment).
6. Has received a live vaccine within 30 days prior to the first dose of study drug.
7. Participants taking strong CYP3A4 or P-glycoprotein inhibitors or inducers are excluded from the study unless they can be transferred to other medications within ≥5 half-lives prior to dosing.
8. Is currently participating in or has participated in a study of an investigational agent or has used an investigational device within 4 weeks prior to the first dose of study treatment. Participants who have entered the follow-up phase of an investigational study may participate as long as it has been 4 weeks after the last dose of the previous investigational agent.
9. Has a diagnosis of immunodeficiency or is receiving chronic systemic steroid therapy (in dosing exceeding 10 mg daily of prednisone equivalent) or any other form of immunosuppressive therapy within 7 days prior the first dose of study drug.
10. Has a known additional potentially life-threatening malignancy that is progressing or has required active treatment within the past 3 years. Participants with basal cell carcinoma of the skin, squamous cell carcinoma of the skin, or carcinoma in situ (eg, breast carcinoma, cervical cancer in situ) that have undergone potentially curative therapy are not excluded.
11. Has known active CNS metastases and/or carcinomatous meningitis. Participants with previously treated brain metastases may participate provided they are radiologically stable, ie, without evidence of progression for at least 4 weeks by repeat imaging (note that the repeat imaging should be performed during study screening), and/or clinically stable and without requirement of steroid treatment for at least 14 days prior to first dose of study treatment.
12. Has an active autoimmune disease that has required systemic treatment in past 2 years (ie, with use of disease modifying agents, corticosteroids or immunosuppressive drugs). Replacement therapy (eg, thyroxine, insulin, or physiologic corticosteroid replacement therapy for adrenal or pituitary insufficiency) is not considered a form of systemic treatment and is allowed. Autoimmune diseases include but are not limited to inflammatory bowel disease (IBD) such as Crohn's disease and ulcerative colitis.
13. Has a history of (non-infectious) pneumonitis that required steroids or has current pneumonitis.
14. Has an active infection requiring systemic therapy.
15. Recent (within the last 12 months) or current GI ulcer or non-immune colitis.
16. Has a known history of human immunodeficiency virus (HIV) infection.
17. Has a known history of Hepatitis B or known active Hepatitis C virus infection.
18. Clinically significant (ie, active) cardiovascular disease: cerebral vascular accident/stroke (<6 months prior to enrollment), myocardial infarction (<6 months prior to enrollment), unstable angina, congestive heart failure (≥New York Heart Association Classification Class II), or uncontrolled cardiac arrhythmia.
19. Has a history or current evidence of any condition, therapy, or laboratory abnormality that might confound the results of the study, interfere with the participant's participation for the full duration of the study, or is not in the best interest of the participant to participate, in the opinion of the treating investigator.
20. Has known psychiatric or substance abuse disorders that would interfere with cooperating with the requirements of the study.
21. A woman of childbearing potential (WOCBP) who has a positive pregnancy test prior to treatment.
22. Is breastfeeding or expecting to conceive or father children within the projected duration of the study.

Number of Participants: Approximately 30 patients from approximately 3 to 5 study centers in the United States will be screened to enroll 25 participants (15 participants in Cohort 1 and 10 participants in Cohort 2) in this study. Enrollment is defined as the time of initiation of the first dose of study drug. Participants who are withdrawn from treatment during the Single-Agent Run-in (Cohort 1) or the first cycle of combination (ie, dose-limiting toxicity [DLT] period) for reasons other than AEs will be replaced.

Treatment Groups and Duration:
  A cycle of treatment will be defined as Q3W.
  The pembrolizumab dose will be 200 mg IV Q3W.
  Dose and schedule adjustments, corticosteroid administration, and monitoring plan are described in the protocol.
  The dose of grapiprant will be 300 mg administered orally BID (daily dose taken at 8- to 12-hour intervals, preferably with food).
  Participants with a DLT within the first cycle will have their dose held until amelioration of their toxicities and be reduced from their existing dose by 50 mg BID or 100 mg BID unless discussed with the Sponsor.
  Participants who experience a first intolerable treatment-emergent adverse event (TEAE) after the first cycle will have their dose held until amelioration of their toxicities and be reduced from their existing dose at 50 mg BID increments. Switching grapiprant administration to a 2 week on/1 week off schedule is also to be considered by the investigator depending on the nature of the TEAE.
  Any participant who requires a decrease in the grapiprant dose below 150 mg BID will have grapiprant treatment discontinued, but may continue to receive pembrolizumab if clinical benefit has been demonstrated.

Participants with Grade 2 or greater dyspepsia for 5 or more days may, at the judgment of the investigator, institute ranitidine at 75 mg orally BID, to be taken 2 hours after the dose of grapiprant, until abdominal discomfort abates.

Additional dose adjustment and monitoring plan is described in the protocol.

Participants, including those who achieve a complete response (CR), may receive treatment with grapiprant and pembrolizumab for up to 2 years or until they experience disease progression, unacceptable toxicity, or consent withdrawal, followed by 30- and 90-Day End of Treatment Follow-up visits after their last day of study drug.

The duration of the study for each participant will include a screening period for inclusion in the study of up to 28 days, a 7-day Single Agent Run-in (for Cohort 1 only), courses of Combination Treatment cycles repeated every 21 days, and End of Treatment Follow-up visits at 30 and 90 days following the last study drug administration for all participants. Participants may continue to receive the study drugs for a maximum of 35 cycles (up to 2 years).

Dose de-escalation for all participants will take place any time safety rules indicate (eg, if 3 or more participants out of the first 5 participants experiences a DLT). Participants already enrolled and receiving drug without severe AEs may be permitted to receive additional doses at the original dose level after discussion with the Sponsor.

The expected enrollment period is 10 months. The study cut-off date is defined as the date when all the participants have either completed 16 weeks of treatment (ie., until the second tumor assessment) or discontinued the study drug. The participants who continue to receive the study drug after the study cut-off date will be followed and appropriate statistical analysis (listings or updated tables for safety, drug exposure and activity) will be performed when all the participants have discontinued the study drug.

Statistical Considerations:

Determination of the sample size: The combination side-effect profile is expected to be similar to pembrolizumab alone.

The recommend sample size for the mTPI design is n=k*(d+1) (Ji and Wang, J Clin Oncol. 2013; 31 (14): 1785-91). If 8 subjects are dosed per dose level (k=8) and there are 2 doses tested (d-2), then it is anticipated that 24 subjects will be required. If 1 dose is tested, then it is anticipated that n=16 subjects will be needed. Following the continuous safety assessment phase, additional subjects up to a total trial size of 25 will be assessed to establish an estimate of efficacy. There is no formal hypothesis testing or adjustment for multiplicity.

General statistical approach: Descriptive analysis of safety parameters will be performed on the whole treated population, defined as all participants exposed to at least one dose of grapiprant. Specifically, both study cohorts will be pooled, and by-cohort analyses will not be performed. Type, frequency, seriousness and relatedness of TEAEs will be analyzed according to Medical Dictionary for Regulatory Activities (MedDRA). Laboratory abnormalities will be analyzed according to National Cancer Institute Common Terminology Criteria for Adverse Events (NCI-CTCAE) v5.0.

Pharmacokinetic Analyses: PK parameters of grapiprant will be summarized using descriptive statistics by dose level and time since last dose. The plasma PK of grapiprant will be described for the Cmax and AUC PK parameters. Any additional PK analyses will be described in the statistical analysis plan (SAP).

Population PK and Exposure-Response Analyses: Data from this study will be included with data collected from previous studies in a population PK analysis. The influence of covariates (eg, body weight, age, sex, race, and concomitant medications) on PK parameters will be investigated, if necessary and appropriate.

Additional exploratory PK and/or exposure-response modeling may be applied to the data, as appropriate.

Results of PK and/or any population PK or exposure-response analyses may be reported outside the clinical study report.

Efficacy analysis: Anti-tumor efficacy data will be descriptively presented on the evaluable response population including participants who had a disease assessment at screening and at a minimum one other time point during the study treatment.

An informal interim analysis will be conducted to enable future trial planning at the Sponsor's discretion and data will be examined on a continuous basis to allow for dose finding decisions.

Example 14. Anti-tumor Activity of Compound B in the CT-26 Colon Adenocarcinoma Mouse Model Compound B has the following formula, or a pharmaceutically acceptable salt thereof, and is an EP4 receptor selective antagonist (see, for example, U.S. Pat. No. 7,238,714).

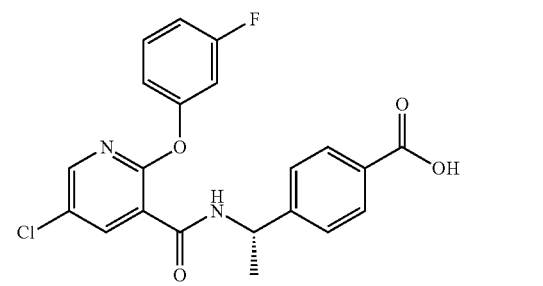

Compound B

The antitumor activity of Compound B as a single agent and combined with a mouse anti-PD-1 antibody was evaluated in the CT-26 mouse colon adenocarcinoma model grown in BALB/c mice. Mice were inoculated subcutaneously in the right flank with $5 \times 10^5$ tumor cells.

When tumors reached an average size of 71 mm$^3$ (6 days after tumor cell inoculation) dosing was initiated. The dosing regimens in the 8 separate cohorts comprising 10 mice each are as follows:

| Group | Treatment | Dose per administration | Dose volume per administration | Dosing Schedule/Days | Administration route |
|---|---|---|---|---|---|
| 1 | Vehicle(0.5%MC) | — | 10 ul/g | BID × 3 + weeks | p.o. |
|   | Rat IgG2(Isotype matched) | 10 mg/kg | 10 ul/g | Day 1,4, 8,11, 15 | i.p. |
| 2 | Anti-PD1 | 10 mg/kg | 10 ul/g | Day 1, 4, 8, 11, 15 | i.p. |
| 3 | Compound B | 15 mg/kg | 10 ul/g | QD × 3 + weeks | p.o. |
| 4 | Compound B | 15 mg/kg | 10 ul/g | BID × 3 + weeks | p.o. |
| 5 | Compound B | 15 mg/kg | 10 ul/g | QD × 3 + weeks | p.o. |
|   | Anti-PD1 | 10 mg/kg | 10 ul/g | Day 1, 4, 8, 11, 15 | i.p. |

| Group | Treatment | Dose per administration | Dose volume per administration | Dosing Schedule/Days | Administration route |
|---|---|---|---|---|---|
| 6 | Compound B | 15 mg/kg | 10 ul/g | BID × 3 + weeks | p.o. |
|   | Anti-PD1 | 10 mg/kg | 10 ul/g | Day 1,4, 8,11, 15 | i.p. |

Figure 22:
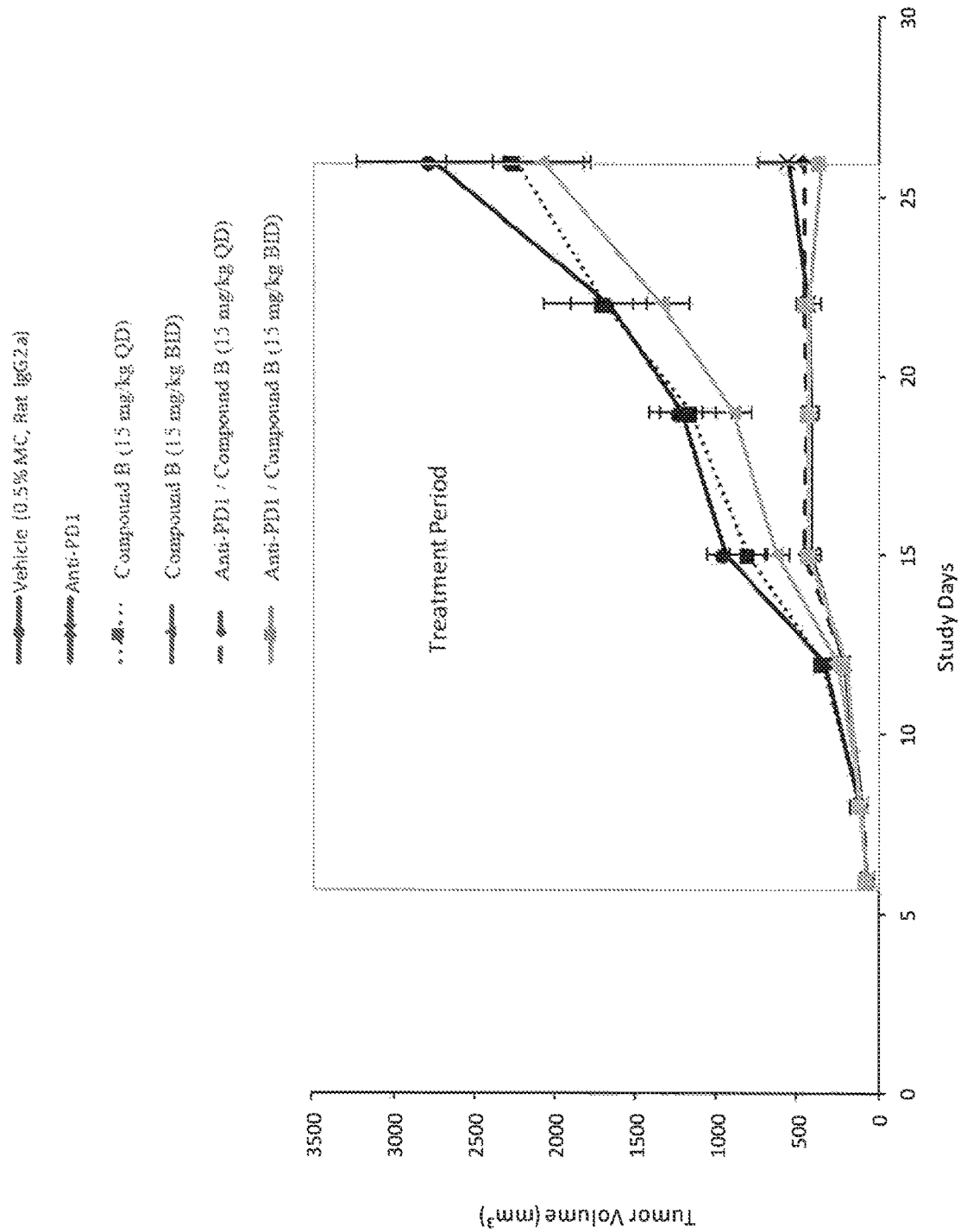
FIG. 22 depicts Growth Kinetics in BALB/C Mice Bearing CT-26 Tumors. BALB/C mice bearing CT-26 tumors were treated with vehicle (0.5% methylcellulose and IgG2a), anti-PD-1, or Compound B at 15 mg/kg QD and BID alone or in combination with anti-PD-1. Mean tumor volumes (mm³) and standard error of the mean (n=10/group) are shown.

During the period of dosing, the tumor growth kinetics in mice treated with Compound B dosed at 15 mg/kg once daily (QD) and BID were not notably different from the vehicle treated mice (FIG. 22). The tumor growth kinetics in mice treated with Compound B dosed at 15 mg/kg QD and BID combined with anti-PD-1 were also not notably different mice treated with single agent anti-PD-1 during the treatment period. Each dosing regimen was tolerated by the mice as indicated by an average increase in body weight in each cohort during the treatment period and after treatment was discontinued.

Figure 23:
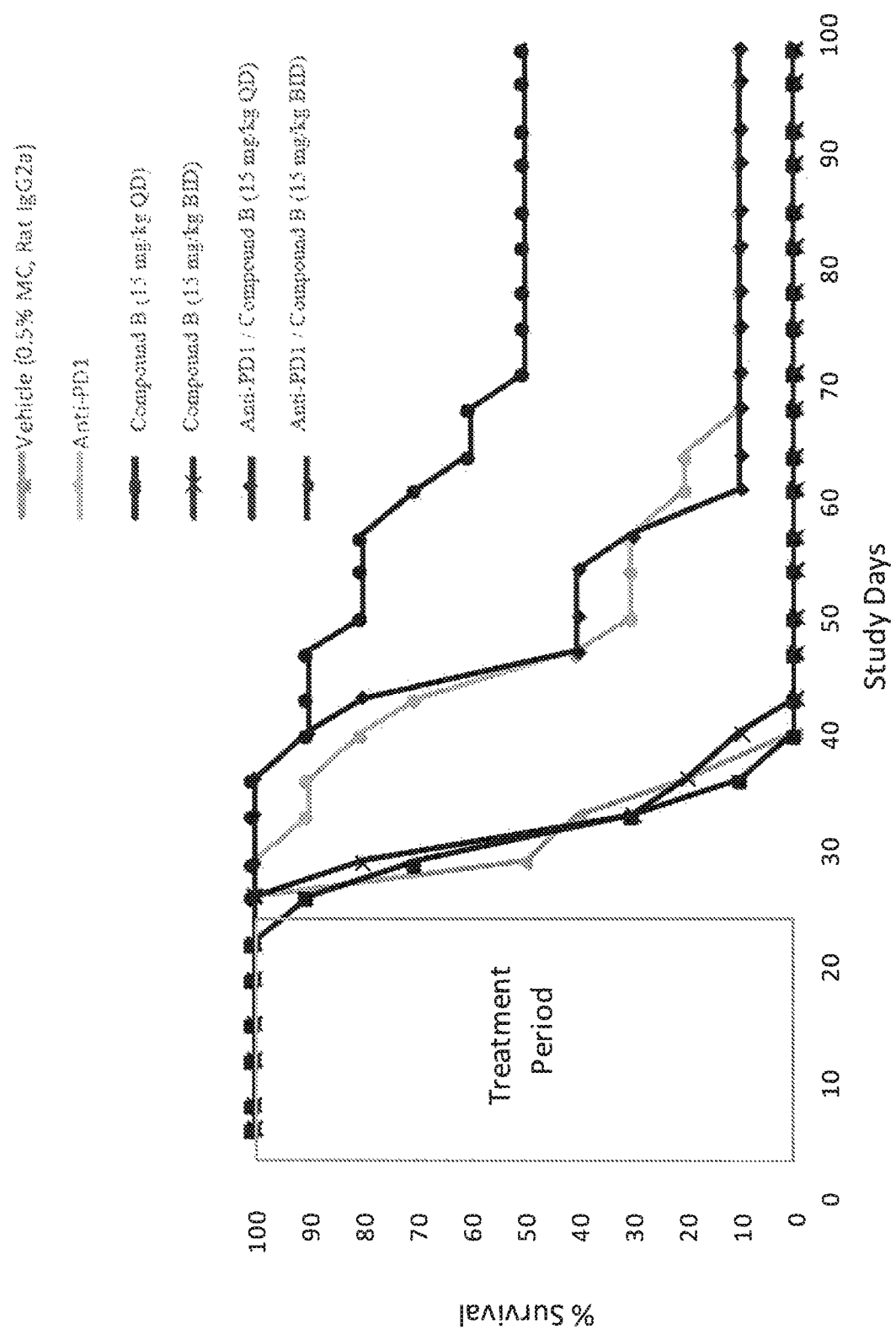
FIG. 23 depicts Kaplan-Meier Curve of Tumor Bearing Mice. Kaplan-Meier curve of tumor-bearing mice treated with vehicle (0.5% methylcellulose and IgG2a), anti-PD-1, or Compound B at 15 mg/kg QD and BID alone or in combination with anti-PD-1. Mice were monitored out 99 days after tumor inoculation, and animals were sacrificed when tumor sizes exceeded 3000 mm³.

After treatment was discontinued, mice treated with Compound B at 15 mg/kg BID in combination with anti-PD-1 demonstrated decreased growth kinetics relative to anti-PD-1 (FIG. 22) and improved survival (FIG. 23). After continuing to monitor the mice for 99 days after tumor inoculation, 5 out of 10 mice were still alive (4 tumor free) whereas only 1 out of 10 mice treated with anti-PD-1 as a single agent and 1 out of 10 mice in the Compound B was still alive and tumor free. These data suggest that Compound B when combined with anti-PD-1 leads to an improved long term antitumor response.

CT26 tumor cells were inoculated into 6 tumor-naive mice or complete responders of CT26 tumor-bearing mice previously treated with Compound B and anti-PD-1 alone or in combination. The data show that the mice with a complete response decreased the growth of CT26 relative to naive mice suggesting there was a vaccinal effect in the cured mice.

The antitumor activity of Compound B as a single agent and combined with a mouse anti-PD1 antibody was evaluated in the CT-26 mouse colon adenocarcinoma model grown in BALB/c mice in an additional experiment. Mice were inoculated subcutaneously in the right flank with 5×10$^5$ tumor cells. When tumors reached an average size of 91 mm$^3$ dosing was initiated. The dosing regimens in the 4 separate cohorts comprising 7 mice each are as follows:

| Group | Treatment | Dose per administration | Dose volume per administration | Dosing Schedule/Days | Administration route |
|---|---|---|---|---|---|
| 1 | Vehicle (0.5&MC) | — | 10 ul/g | BID × 17 days | po |
|   | PBS | — | 10 ul/g | BIW × 4 doses | ip |
| 2 | Compound B | 15 mg/kg | 10 ul/g | BID × 17 days | po |
|   | PBS | — | 10 ul/g | BIW × 4 doses | ip |
| 3 | Anti-PD1 | 10 mg/kg | 10 ul/g | BIW × 5 doses | ip |
|   | Vehicle | — | 10 ul/g | BID × 16 days | po |
| 4 | Compound B | 15 mg/kg | 10 ul/g | BID × 17 days | po |
|   | Anti-PD1 | 10 mg/kg | 10 ul/g | BIW × 5 doses | ip |

Figure 26:
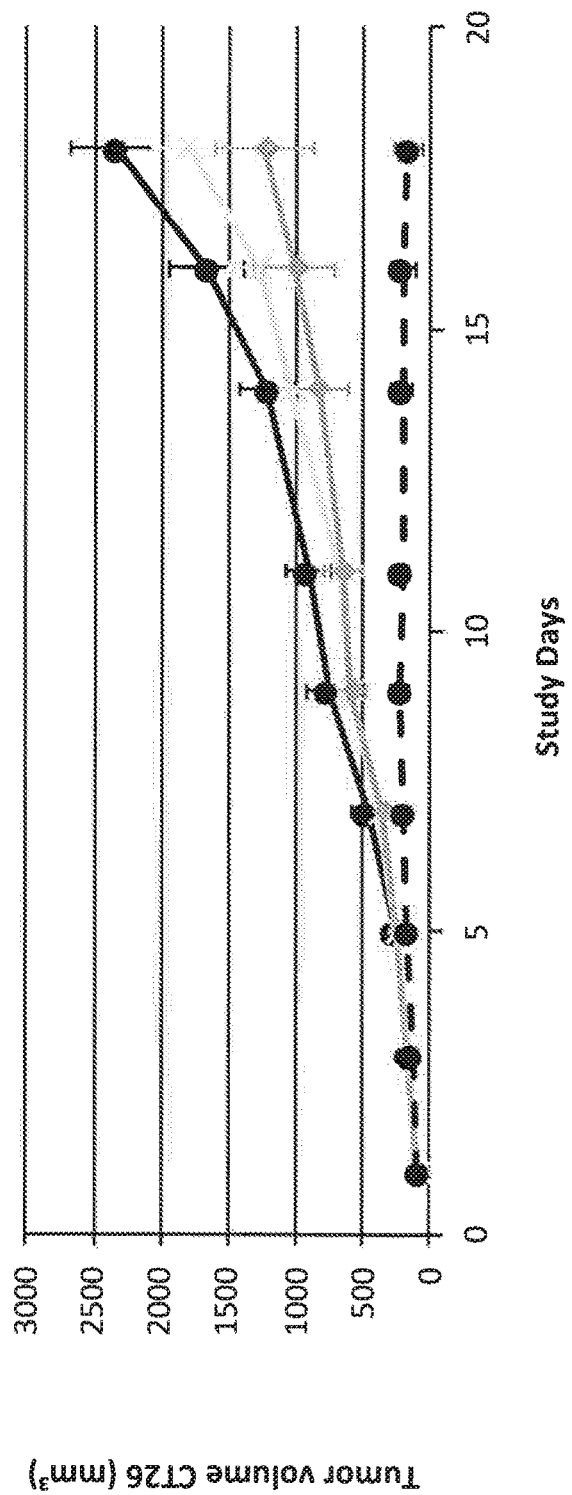
FIG. 26 depicts BALB/C mice bearing CT-26 tumors treated with vehicle (0.5% methylcellulose and PBS), anti-PD1, or Compound B at 15 mg/kg BID alone or in combination with anti-PD1. Mean tumor volumes (mm³) and standard error of the mean (n=7/group) are shown.

During the period of dosing, the tumor growth kinetics in mice treated with Compound B dosed at 15 mg/kg twice daily (BID) and anti-PD1 were less than that of the vehicle group (FIG. 26). The tumor growth kinetics in mice treated with Compound B dosed at 15 mg/kg BID combined with anti-PD1 were lower than mice treated with either single agent. Each dosing regimen was tolerated by the mice as indicated by an average increase in body weight in each cohort during the treatment period.

Example 15. Anti-tumor Activity of Compound B in the 4T1 Breast Cancer Mouse Model The antitumor activity of Compound B (as described in example 14 above) as a single agent and combined with a mouse anti-CTLA4 antibody was evaluated in the 4T1 mouse breast cancer model grown in BALB/c mice. Mice were inoculated subcutaneously in the right flank with 3×10$^5$ tumor cells. When tumors reached an average size of 100 mm$^3$ (7 days after tumor cell inoculation) dosing was initiated.

Figure 24:
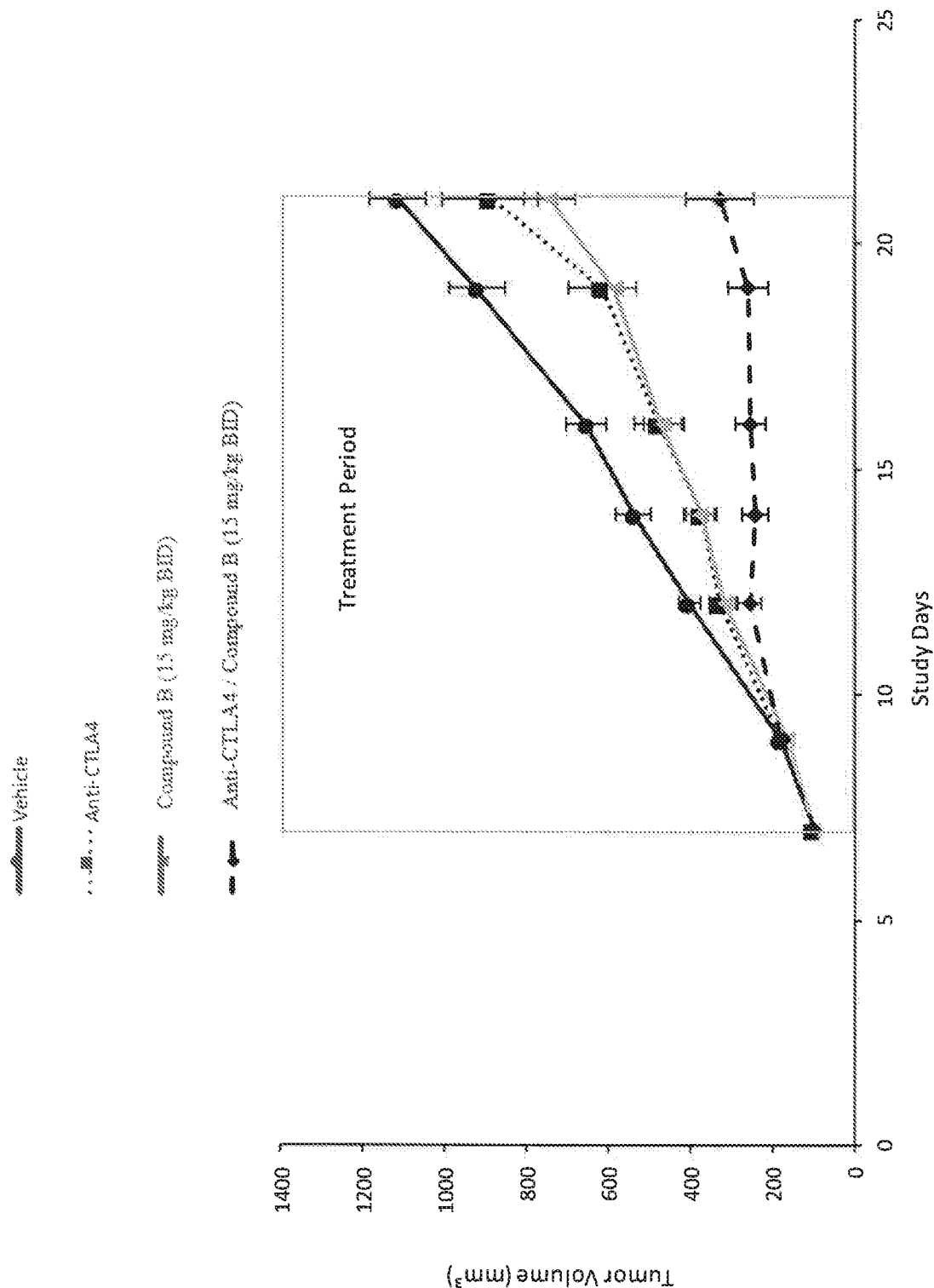
FIG. 24 depicts Tumor Growth Kinetics in BALB/C Mice Bearing 4T1 Tumors. BALB/C mice bearing 4T1 tumors were treated with vehicle, anti-CTLA4, or Compound B at 15 mg/kg BID alone or in combination with anti-CTLA41. Mean tumor volumes (mm³) and standard error of the mean (n=10/group) are shown.

During the period of dosing, the tumor growth kinetics in mice treated with Compound B dosed at 15 mg/kg BID and anti-CTLA4 were decreased relative to the vehicle treated mice (FIG. 24). Moreover, the tumor growth kinetics in mice treated with Compound B and anti-CTLA4 combined was decreased relative to either agent when dosed alone. Each dosing regimen was tolerated by the mice as indicated by an average increase in body weight in each cohort during the treatment period and after treatment was discontinued.

Figure 25:
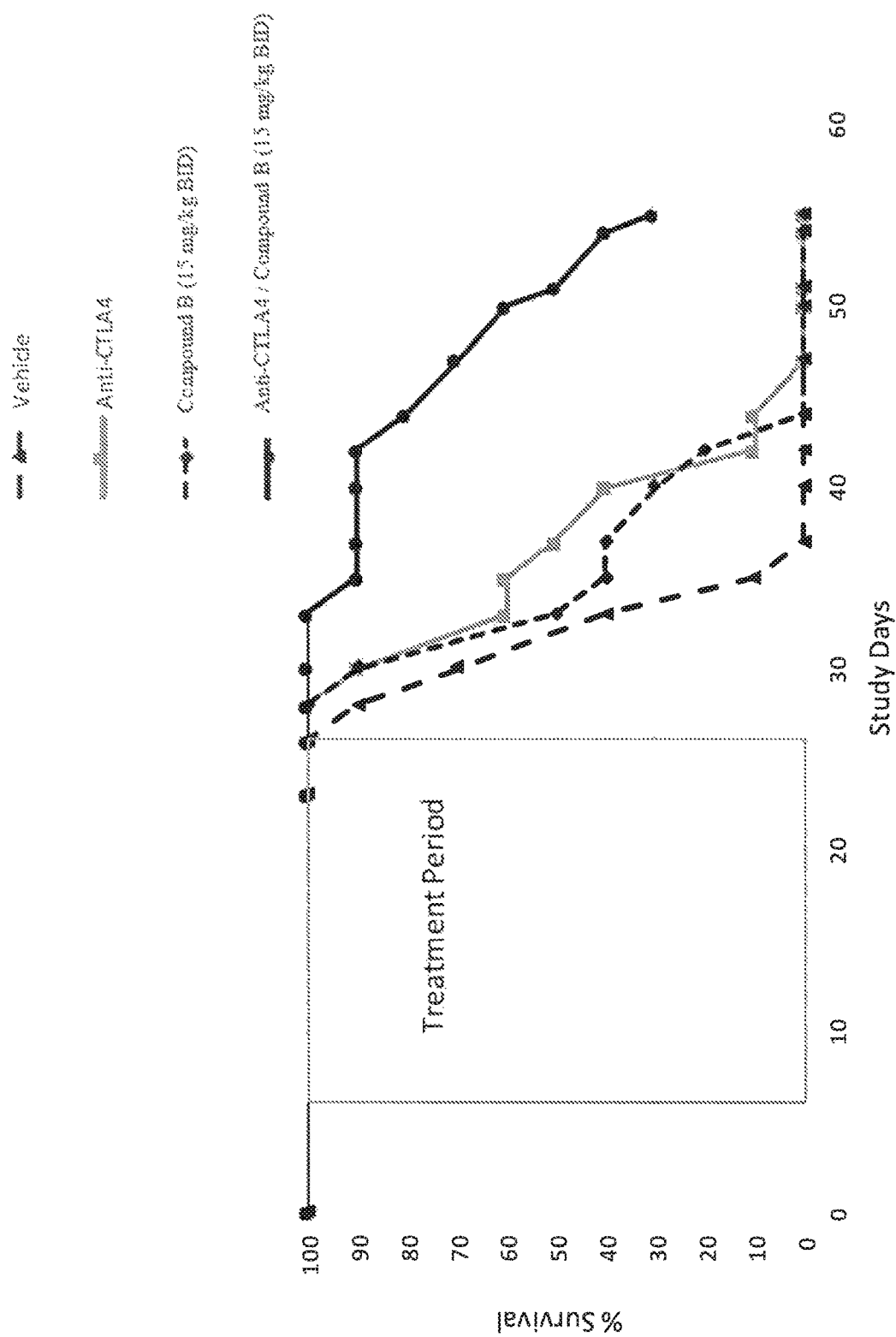
FIG. 25 depicts Kaplan-Meier Curve of Tumor-Bearing Mice Study. Kaplan-Meier curve of tumor-bearing mice treated with vehicle, anti-CTLA4, or Compound B at 15 mg/kg BID alone or in combination with anti-CTLA4. Mice were monitored for 41 days after tumor inoculation, and animals were sacrificed when tumor sizes exceeded 3000 mm³.

After treatment was discontinued, mice treated with Compound B at 15 mg/kg BID in combination with anti-CTLA4 demonstrated improved survival rate relative to either single agent alone (FIG. 25). For example, after continuing to monitor the mice for 47 days after tumor inoculation, 7 of 10 mice treated with the combination were still alive whereas none of mice treated with either single agent alone was alive 47 days after tumor inoculation. 3 of 10 mice treated with the combination were still alive at the end of the study 55 days after tumor inoculation. These data suggest that the Compound B and anti-CTLA4 combination leads to an improved antitumor response relative to either agent alone.

The antitumor activity of Compound B as a single agent and combined with a mouse anti-PD1 antibody was evaluated in the 4T1 mouse breast cancer model grown in BALB/c mice in an additional experiment. Mice were inoculated subcutaneously in the right flank with 3×10$^5$ tumor cells. When tumors reached an average size of 97 mm$^3$ dosing was initiated. The dosing regimens in the 4 separate cohorts comprising 7 mice each are as follows:

| Group | Treatment | Dose per administration | Dose volume per administration | Dosing Schedule/Days | Administration route |
|---|---|---|---|---|---|
| 1 | Vehicle (0.5&MC) | — | 10 ul/g | BID × 20 days | po |
|   | PBS | — | 10 ul/g | BIW × 5 doses | ip |
| 2 | Compound B | 15 mg/kg | 10 ul/g | BID × 20 days | po |
|   | PBS | — | 10 ul/g | BIW × 5 doses | ip |
| 3 | Anti-PD1 | 10 mg/kg | 10 ul/g | BIW × 6 doses | ip |
|   | Vehicle | — | 10 ul/g | BID × 19 days | po |
| 4 | Compound B | 15 mg/kg | 10 ul/g | BID × 20 days | po |
|   | Anti-PD1 | 10 mg/kg | 10 ul/g | BIW × 6 doses | ip |

Figure 27:
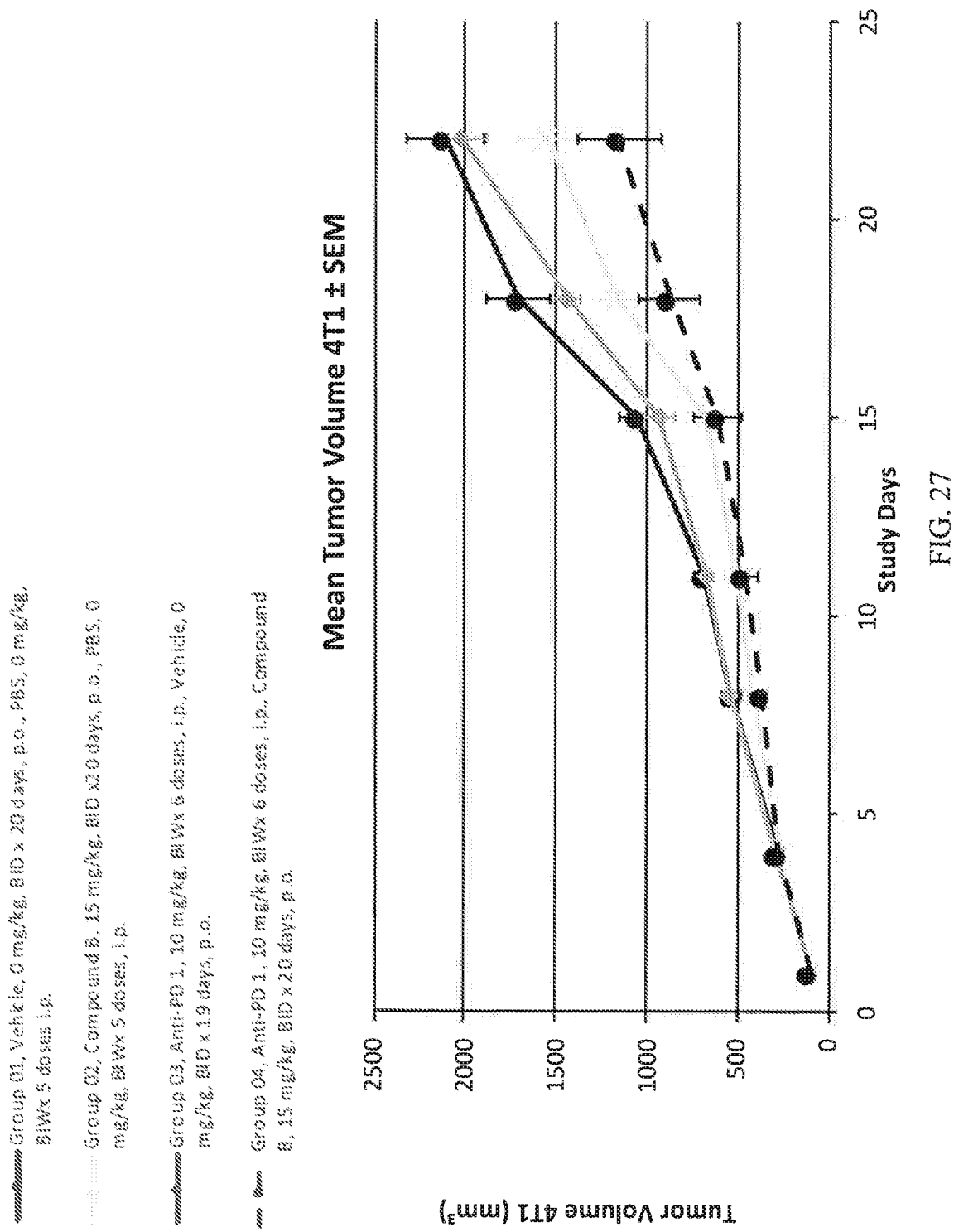
FIG. 27 depicts BALB/C mice bearing 4T1 tumors treated with vehicle (0.5% methylcellulose and PBS), anti-PD1, or Compound B at 15 mg/kg BID alone or in combination with anti-PD1. Mean tumor volumes (mm³) and standard error of the mean (n=7/group) are shown.

During the period of dosing, the tumor growth kinetics in mice treated with Compound B dosed at 15 mg/kg twice daily (BID) was less than that of the vehicle group and anti-PD1 when dosed alone (FIG. 27). The tumor growth kinetics in mice treated with Compound B dosed at 15 mg/kg BID combined with anti-PD1 were lower than mice treated with either single agent. Each dosing regimen was tolerated by the mice as indicated by an average increase in body weight in each cohort during the treatment period.

Example 16. Effect of Compound B on Immune Cell Composition in the CT-26 Colon Adenocarcinoma Mouse Model The immune cell composition of Compound B (as described in example 14 above) as a single agent and combined with a mouse anti-PD1 antibody was evaluated in the CT-26 mouse colon adenocarcinoma model grown in BALB/c mice. Mice were inoculated subcutaneously in the right flank with $5 \times 10^5$ tumor cells. When tumors reached an average size of 85 mm$^3$ dosing was initiated. The dosing regimens in the 4 separate cohorts comprising 10 mice each are listed as follows:

| Group | Treatment | Dose per administration | Dose volume per administration | Dosing Schedule/Days | Administration route | Number of mice |
|---|---|---|---|---|---|---|
| Group 1 | Vehicle (0.5&MC) | — | 10 ul/g | BID × 7 days | po | 10 |
|   | PBS | — | 5 ul/g | Q3D × 3 doses | ip |   |
| Group 2 | Compound B | 15 mg/kg | 10 ul/g | BID × 7 days | po | 10 |
|   | PBS | — | 5 ul/g | Q3D × 3 doses | ip |   |
| Group 3 | Anti-PD1 | 10 mg/kg | 5 ul/g | Q3D × 3 doses | ip | 10 |
|   | Vehicle | — | 10 ul/g | BID × 7 days | po |   |
| Group 4 | Compound B | 15 mg/kg | 10 ul/g | BID × 7 days | po | 10 |
|   | Anti-PD1 | 10 mg/kg | 5 ul/g | Q3D × 3 doses | ip |   |

After dosing animals for 7 days, tumors were resected and used to prepare single cell suspensions. Live cells representing tumor and immune cells were stained with cocktails of antibodies targeting multiple immune cell markers (anti-CD45, anti-CD3, anti-CD4, anti-CD8, anti-CD25, anti-FoxP3, anti-PD-1, anti-CD11c) conjugated to different fluorescent tags. The stained cells were fixed in 4% paraformaldehyde and quantified using a multi-color flow cytometer (Fortessa). The data was analyzed with FloJo software.

Figure 28:
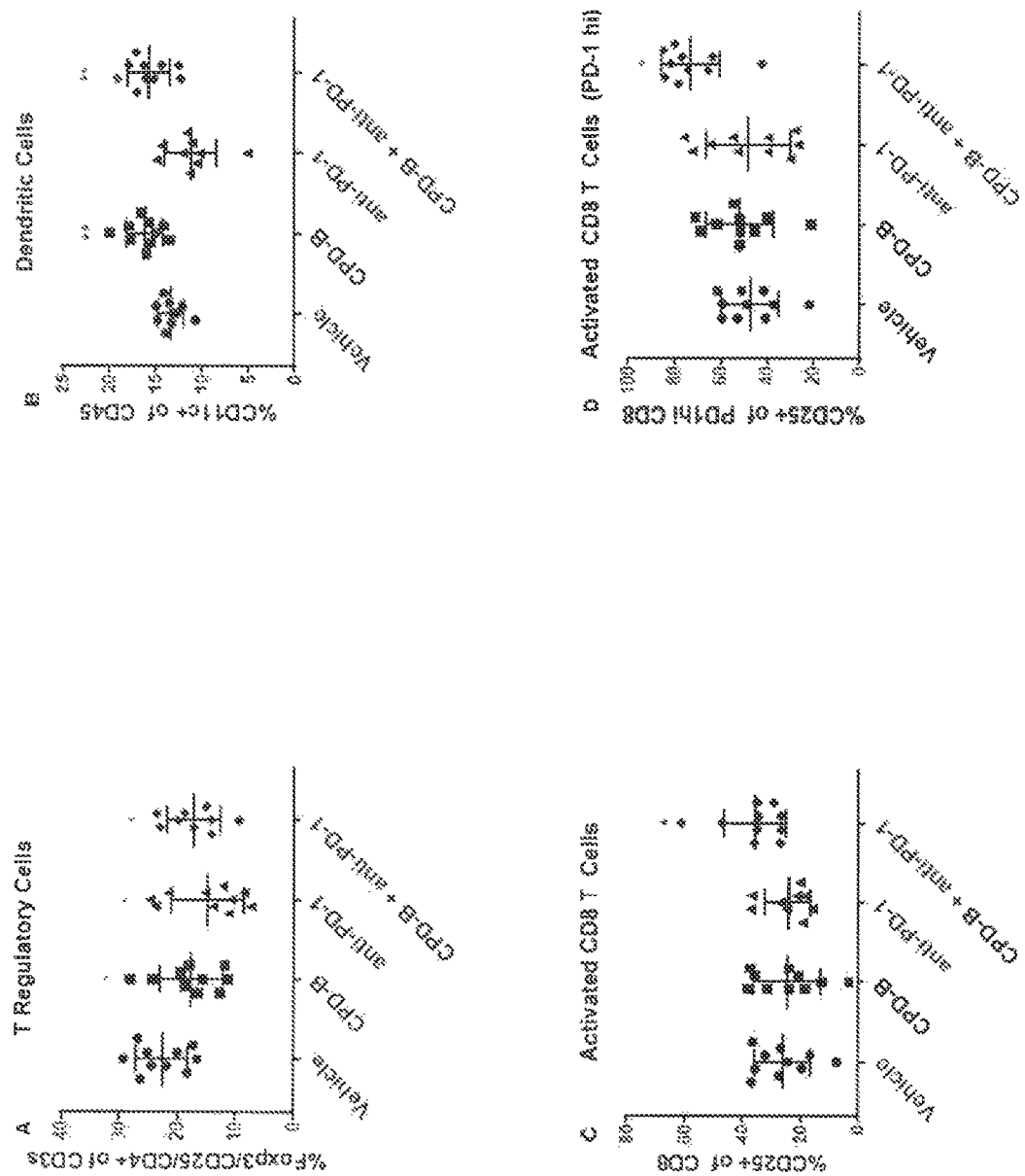
FIG. 28 depicts the immune cell composition of CT-26 tumors grown in BALB/c mice treated with vehicle (0.5% methylcellulose and PBS), anti-PD1, or Compound B (CPD-B) at 15 mg/kg BID alone or in combination with anti-PD1. The percentage of regulatory T cells (a), dendritic cells (b), activated T cells (c) and activated PD-1 high T cells (d) is shown. p values determined using a Student's T-test comparing vehicle to treated groups; *p<0.05, **p<0.01.

Compound B, anti-PD-1 and the combination of the 2 agents resulted in a significant decrease in regulatory T cells (CD45, CD4, FoxP3, CD25 positive) (FIG. 28a). Compound B dosed alone and with anti-PD-1 led to increased percentage of dendritic cells (CD45, CD11c positive), whereas anti-PD-1 alone did not (FIG. 28b). The combination of Compound B with anti-PD-1 also led to increased percentage of activated T cells (CD45, CD3, CD8) by evaluating the CD25 expression where as either agent dosed alone did not (FIG. 28c). The percentage of CD25 was higher in T cells with increased levels of PD-1 (FIG. 28d). Collectively, these findings demonstrate that Compound B alone and when combined with anti-PD-1 antibodies alters the immune cell composition of CT-26 tumors indicative of an increased proinflammatory phenotype.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound selected from the group consisting of:
(i) Compound 4:
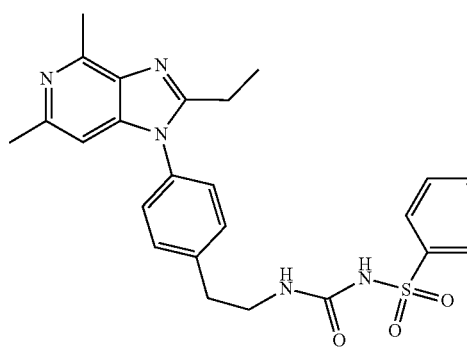
· HCl;
(ii) Compound 1:
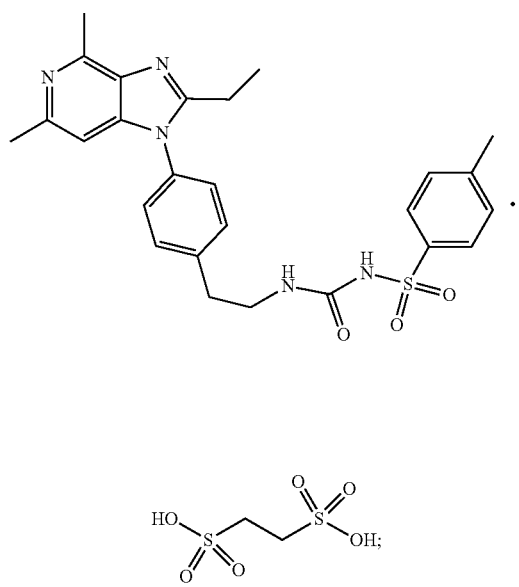
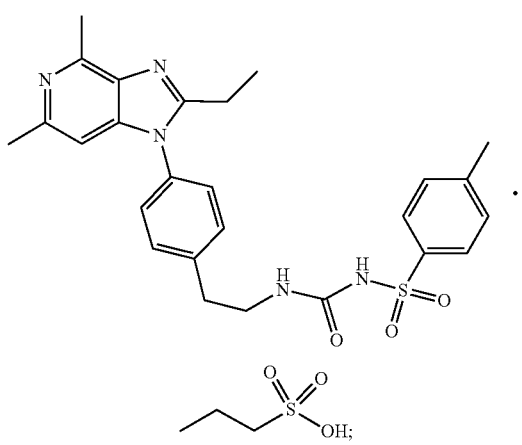
(iii) Compound 2:
(iv) Compound 3:
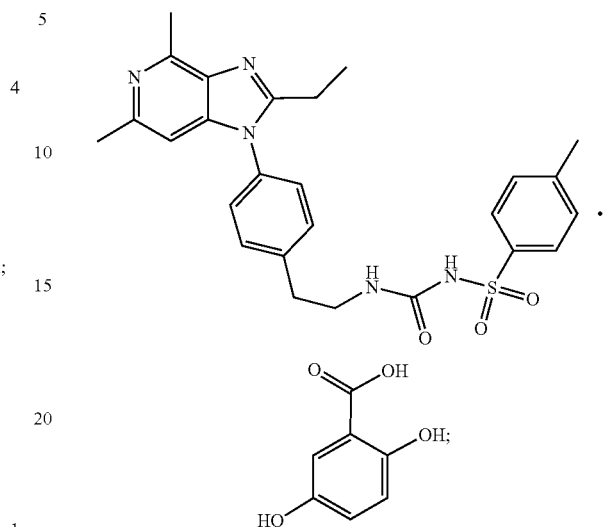
(v) Compound 5:
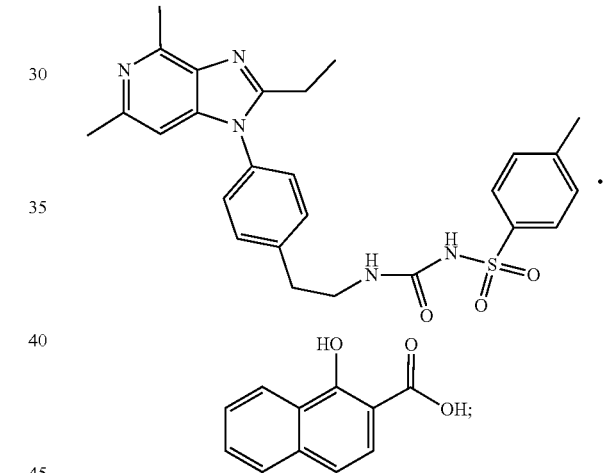
(vi) Compound 6
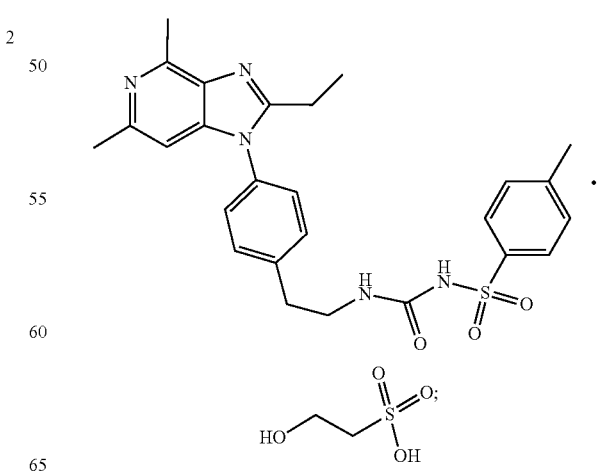

-continued (vii) Compound 7:

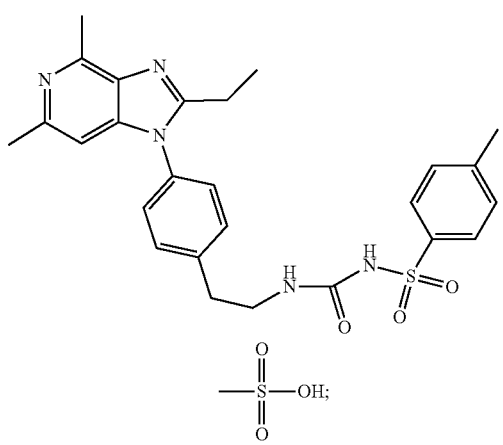

(viiii) Compound 8:

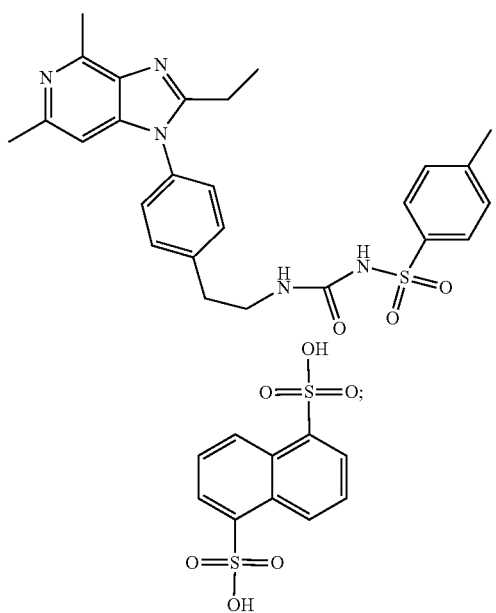

(ix) Compound 9:

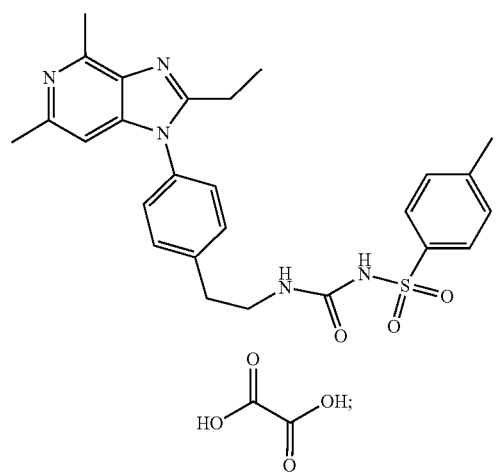

-continued (x) Compound 10:

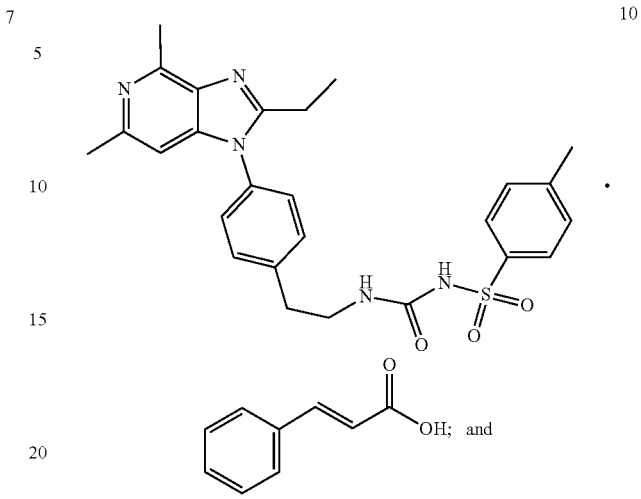

(xi) Compound 11:

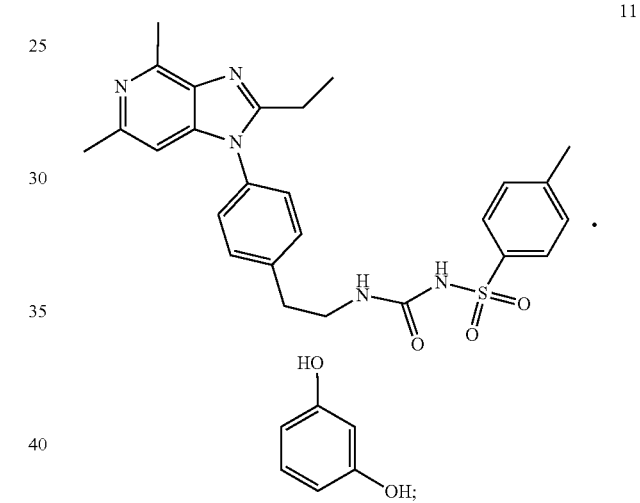

wherein the compound is crystalline.

2. The compound according to claim 1, wherein said compound is a crystalline solid substantially free of amorphous compound.

3. The compound according to claim 1, wherein said compound is substantially free of impurities.

4. A composition comprising the compound according to claim 1 and a pharmaceutically acceptable carrier or excipient.

5. A method of inhibiting or preventing prostaglandin EP4 receptor activity in a patient comprising administering to said patient the compound according to claim 1 or a composition thereof.

6. A method for treating a cancer in a patient comprising administering to the patient the compound according to claim 1 or a composition thereof, wherein the cancer is selected from the group consisting of basal cell carcinoma, adenocarcinoma, oral cancer, esophageal cancer, stomach cancer, intestinal cancer, colon cancer, gastric cancer, liver cancer, bladder cancer, pancreatic cancer, ovarian cancer, cervical cancer, lung cancer, breast cancer, skin cancer, prostate cancer, and renal cell carcinoma.

7. The method according to claim 6, wherein the method comprises administration of the compound, or a composition thereof, in combination with an additional therapeutic agent.

8. The compound according to claim 1, wherein:
(i) Compound 4 is a crystalline solid form having one or more peaks in its XRPD selected from those at about 14.9, about 16.8 and about 24.5 degrees 2-theta;
(ii) Compound 1 is a crystalline solid form having one or more peaks in its XRPD selected from those at about 13.0, about 15.2 and about 22.0 degrees 2-theta;
(iii) Compound 2 is a crystalline solid form having one or more peaks in its XRPD selected from those at about 10.6, about 19.4 and about 22.4 degrees 2-theta;
(iv) Compound 3 is a crystalline solid form having one or more peaks in its XRPD selected from those at about 8.2, about 9.5 and about 12.4 degrees 2-theta;
(v) Compound 5 is a crystalline solid form having one or more peaks in its XRPD selected from those at about 4.9, about 15.8 and about 25.2 degrees 2-theta;
(vi) Compound 6 is a crystalline solid form having one or more peaks in its XRPD selected from those at about 5.8, about 15.2 and about 22.1 degrees 2-theta;
(vii) Compound 7 is a crystalline solid form having one or more peaks in its XRPD selected from those at about 15.6, about 19.1 and about 22.5 degrees 2-theta;
(viii) Compound 8 is a crystalline solid form having one or more peaks in its XRPD selected from those at about 13.5, about 14.0 and about 21.7 degrees 2-theta;
(ix) Compound 9 is a crystalline solid form having one or more peaks in its XRPD selected from those at about 16.6, about 17.5 and about 23.2 degrees 2-theta;
(x) Compound 10 is a crystalline solid form having one or more peaks in its XRPD selected from those at about 3.6, about 9.4 and about 17.3 degrees 2-theta; and
(xi) Compound 11 is a crystalline solid form having one or more peaks in its XRPD selected from those at about 9.6, about 15.1 and about 15.7 degrees 2-theta.

9. The compound according to claim 1, wherein:
(i) Compound 4 is a crystalline solid form having at least two peaks in its XRPD selected from those at about 14.9, about 16.8 and about 24.5 degrees 2-theta;
(ii) Compound 1 is a crystalline solid form having at least two peaks in its XRPD selected from those at about 13.0, about 15.2 and about 22.0 degrees 2-theta;
(iii) Compound 2 is a crystalline solid form having at least two peaks in its XRPD selected from those at about 10.6, about 19.4 and about 22.4 degrees 2-theta;
(iv) Compound 3 is a crystalline solid form having at least two peaks in its XRPD selected from those at about 8.2, about 9.5 and about 12.4 degrees 2-theta;
(v) Compound 5 is a crystalline solid form having at least two peaks in its XRPD selected from those at about 4.9, about 15.8 and about 25.2 degrees 2-theta;
(vi) Compound 6 is a crystalline solid form having at least two peaks in its XRPD selected from those at about 5.8, about 15.2 and about 22.1 degrees 2-theta;
(vii) Compound 7 is a crystalline solid form having at least two peaks in its XRPD selected from those at about 15.6, about 19.1 and about 22.5 degrees 2-theta;
(viii) Compound 8 is a crystalline solid form having at least two peaks in its XRPD selected from those at about 13.5, about 14.0 and about 21.7 degrees 2-theta;
(ix) Compound 9 is a crystalline solid form having at least two peaks in its XRPD selected from those at about 16.6, about 17.5 and about 23.2 degrees 2-theta;
(x) Compound 10 is a crystalline solid form having at least two peaks in its XRPD selected from those at about 3.6, about 9.4 and about 17.3 degrees 2-theta; and
(xi) Compound 11 is a crystalline solid form having at least two peaks in its XRPD selected from those at about 9.6, about 15.1 and about 15.7 degrees 2-theta.

10. The compound according to claim 1, wherein:
(i) Compound 4 is of Form A;
(ii) Compound 1 is of Form A;
(iii) Compound 2 is of Form A;
(iv) Compound 3 is of Form A;
(v) Compound 5 is of Form A;
(vi) Compound 6 is of Form A;
(vii) Compound 7 is of Form A;
(viii) Compound 8 is of Form A;
(ix) Compound 9 is of Form A;
(x) Compound 10 is of Form A; and
(xi) Compound 11 is of Form A.

11. The compound according to claim 1, wherein:
(i) Compound 4 is a crystalline solid form having an XRPD substantially similar to that depicted in FIG. 7;
(ii) Compound 1 is a crystalline solid form having an XRPD substantially similar to that depicted in FIG. 1;
(iii) Compound 2 is a crystalline solid form having an XRPD substantially similar to that depicted in FIG. 3;
(iv) Compound 3 is a crystalline solid form having an XRPD substantially similar to that depicted in FIG. 5;
(v) Compound 5 is a crystalline solid form having an XRPD substantially similar to that depicted in FIG. 9;
(vi) Compound 6 is a crystalline solid form having an XRPD substantially similar to that depicted in FIG. 11;
(vii) Compound 7 is a crystalline solid form having an XRPD substantially similar to that depicted in FIG. 13;
(viii) Compound 8 is a crystalline solid form having an XRPD substantially similar to that depicted in FIG. 15;
(ix) Compound 9 is a crystalline solid form having an XRPD substantially similar to that depicted in FIG. 17;
(x) Compound 10 is a crystalline solid form having an XRPD substantially similar to that depicted in FIG. 19; and
(xi) Compound 11 is a crystalline solid form having an XRPD substantially similar to that depicted in FIG. 21.

12. The compound according to claim 1, wherein:
(i) Compound 4 is a crystalline solid form having all three peaks in its XRPD selected from those at about 14.9, about 16.8 and about 24.5 degrees 2-theta;
(ii) Compound 1 is a crystalline solid form having all three peaks in its XRPD selected from those at about 13.0, about 15.2 and about 22.0 degrees 2-theta;
(iii) Compound 2 is a crystalline solid form having all three peaks in its XRPD selected from those at about 10.6, about 19.4 and about 22.4 degrees 2-theta;
(iv) Compound 3 is a crystalline solid form having all three peaks in its XRPD selected from those at about 8.2, about 9.5 and about 12.4 degrees 2-theta;
(v) Compound 5 is a crystalline solid form having all three peaks in its XRPD selected from those at about 4.9, about 15.8 and about 25.2 degrees 2-theta;
(vi) Compound 6 is a crystalline solid form having all three peaks in its XRPD selected from those at about 5.8, about 15.2 and about 22.1 degrees 2-theta;
(vii) Compound 7 is a crystalline solid form having all three peaks in its XRPD selected from those at about 15.6, about 19.1 and about 22.5 degrees 2-theta;
(viii) Compound 8 is a crystalline solid form having all three peaks in its XRPD selected from those at about 13.5, about 14.0 and about 21.7 degrees 2-theta;

(ix) Compound 9 is a crystalline solid form having all three peaks in its XRPD selected from those at about 16.6, about 17.5 and about 23.2 degrees 2-theta;

(x) Compound 10 is a crystalline solid form having all three peaks in its XRPD selected from those at about 3.6, about 9.4 and about 17.3 degrees 2-theta; and (xi) Compound 11 is a crystalline solid form having all three peaks in its XRPD selected from those at about 9.6, about 15.1 and about 15.7 degrees 2-theta.

* * * * *